(12) United States Patent
Ellis, III

(10) Patent No.: US 7,606,854 B2
(45) Date of Patent: *Oct. 20, 2009

(54) INTERNAL HARDWARE FIREWALLS FOR MICROCHIPS

(76) Inventor: Frampton E. Ellis, III, 2895 S. Abingdon St., #B2, Arlington, VA (US) 22206-1331

( * ) Notice: Subject to any disclaimer, the term of this patent is extended or adjusted under 35 U.S.C. 154(b) by 1187 days.

This patent is subject to a terminal disclaimer.

(21) Appl. No.: 09/884,041

(22) Filed: Jun. 20, 2001

(65) Prior Publication Data

US 2002/0059392 A1 May 16, 2002

Related U.S. Application Data

(63) Continuation of application No. 09/315,026, filed on May 20, 1999, now Pat. No. 7,024,449, and a continuation-in-part of application No. 09/213,875, filed on Dec. 17, 1998, now Pat. No. 6,725,250, which is a continuation-in-part of application No. 08/980,058, filed on Nov. 26, 1997, now Pat. No. 6,732,141, and a continuation-in-part of application No. PCT/US98/27058, filed on Dec. 17, 1998, and a continuation-in-part of application No. 09/085,755, filed on May 27, 1998, and a continuation-in-part of application No. PCT/US97/21812, filed on Nov. 28, 1997.

(60) Provisional application No. 60/134,552, filed on May 17, 1999, provisional application No. 60/088,459, filed on Jun. 8, 1998, provisional application No. 60/087,587, filed on Jun. 1, 1998, provisional application No. 60/086,516, filed on May 22, 1998, provisional application No. 60/086,588, filed on May 22, 1998, provisional application No. 60/086,948, filed on May 27, 1998, provisional application No. 60/068,366, filed on Dec. 19, 1997, provisional application No. 60/066,415, filed on Nov. 24, 1997, provisional application No. 60/066,313, filed on Nov. 21, 1997, provisional application No. 60/033,871, filed on Dec. 20, 1996, provisional application No. 60/032,207, filed on Dec. 2, 1996, provisional application No. 60/031,855, filed on Nov. 29, 1996.

(51) Int. Cl.
*G06F 15/16* (2006.01)
*G06F 9/00* (2006.01)

(52) U.S. Cl. ............................ 709/201; 709/209; 726/11

(58) Field of Classification Search .................. 712/10, 712/11, 32, 34; 709/201, 202, 223–226, 709/229; 726/2, 3, 11
See application file for complete search history.

(56) References Cited

U.S. PATENT DOCUMENTS 4,245,306 A 1/1981 Besemer et al.

(Continued)

FOREIGN PATENT DOCUMENTS

DE 40 08 335 A1 9/1991

(Continued)

OTHER PUBLICATIONS

Slater, Michael, "The Microprocessor Today", IEEE Micro 1996, pp. 32-44.*

(Continued)

*Primary Examiner*—Krisna Lim
*Assistant Examiner*—Aaron Strange
(74) *Attorney, Agent, or Firm*—DLA Piper LLP US

(57) ABSTRACT

A personal computer, comprising a microchip, the microchip comprising at least four microprocessors, exclusive of any digital signal processors (DSPs); a non-volatile memory component; a power management component; a internal firewall with a hardware component, the internal firewall being configured to allow and/or deny access to portions of the microchip both to a user of the personal computer and to a user of the microchip from a network of computers during a shared use of the microchip, and the internal firewall being configured to deny access to portions of the microchip from the network; and a wireless network connection mechanism configured to connect the personal computer to the network, the network comprising the Internet.

151 Claims, 19 Drawing Sheets

U.S. PATENT DOCUMENTS

| | | |
|---|---|---|
| 4,278,837 A | 7/1981 | Best |
| 4,747,139 A | 5/1988 | Taaffe |
| 4,827,508 A | 5/1989 | Shear |
| 4,918,596 A | 4/1990 | Nakano |
| 4,969,092 A | 11/1990 | Shorter |
| 5,025,369 A | 6/1991 | Schwartz |
| 5,031,089 A | 7/1991 | Liu et al. |
| 5,103,393 A | 4/1992 | Harris et al. |
| 5,109,329 A | 4/1992 | Strelioff |
| 5,109,512 A | 4/1992 | Bahr et al. |
| 5,136,708 A | 8/1992 | Lapourte et al. |
| 5,155,808 A | 10/1992 | Shimizu |
| 5,237,507 A | 8/1993 | Chasek |
| 5,260,943 A | 11/1993 | Comroe et al. |
| 5,283,819 A | 2/1994 | Glick et al. |
| 5,291,494 A | 3/1994 | Bruckert et al. |
| 5,341,477 A | 8/1994 | Pitkin et al. |
| 5,349,682 A | 9/1994 | Rosenberry |
| 5,357,404 A | 10/1994 | Bright et al. |
| 5,357,632 A | 10/1994 | Pian et al. |
| 5,361,362 A | 11/1994 | Benkeser et al. |
| 5,381,534 A | 1/1995 | Shi |
| 5,388,211 A | 2/1995 | Hornbuckle ................. 717/11 |
| 5,392,400 A | 2/1995 | Berkowitz et al. |
| 5,410,651 A | 4/1995 | Sekizawa et al. |
| 5,426,741 A | 6/1995 | Butts, Jr. et al. |
| 5,428,783 A | 6/1995 | Lake |
| 5,457,797 A | 10/1995 | Butterworth et al. |
| 5,497,465 A | 3/1996 | Chin et al. |
| 5,515,511 A | 5/1996 | Nguyen et al. |
| 5,522,070 A | 5/1996 | Sumimoto |
| 5,535,408 A | 7/1996 | Hillis |
| 5,546,594 A | 8/1996 | Wazumi |
| 5,550,984 A | 8/1996 | Gelb |
| 5,568,375 A | 10/1996 | Rausch |
| 5,570,270 A | 10/1996 | Naedel et al. |
| 5,572,643 A | 11/1996 | Judson |
| 5,586,121 A | 12/1996 | Moura et al. |
| 5,587,928 A | 12/1996 | Jones et al. |
| 5,588,003 A | 12/1996 | Ohba et al. |
| 5,590,284 A | 12/1996 | Crosetto |
| 5,592,376 A | 1/1997 | Hodroff ........................ 705/14 |
| 5,594,491 A | 1/1997 | Hodge et al. |
| 5,600,597 A * | 2/1997 | Kean et al. ............. 365/189.08 |
| 5,606,615 A | 2/1997 | Lapointe et al. |
| 5,608,448 A | 3/1997 | Smoral et al. |
| 5,615,127 A | 3/1997 | Beatty et al. |
| 5,627,879 A | 5/1997 | Russell et al. |
| 5,666,484 A | 9/1997 | Orimo et al. |
| 5,678,028 A | 10/1997 | Bershteyn et al. |
| 5,680,548 A | 10/1997 | Trugman |
| 5,696,902 A | 12/1997 | Leclercq et al. |
| 5,701,507 A | 12/1997 | Bonneau, Jr. et al. |
| 5,710,884 A | 1/1998 | Dedrick |
| 5,734,913 A | 3/1998 | Iwamura et al. |
| 5,748,489 A | 5/1998 | Beatty et al. |
| 5,754,766 A | 5/1998 | Shaw et al. |
| 5,758,077 A | 5/1998 | Danahy et al. |
| 5,758,345 A | 5/1998 | Wang |
| 5,761,507 A | 6/1998 | Govett |
| 5,764,889 A | 6/1998 | Ault et al. |
| 5,774,337 A | 6/1998 | Lee et al. |
| 5,774,668 A | 6/1998 | Choquier et al. |
| 5,784,628 A | 7/1998 | Reneris |
| 5,790,431 A | 8/1998 | Ahrens, Jr. et al. |
| 5,793,968 A | 8/1998 | Gregerson et al. |
| 5,794,059 A | 8/1998 | Barker et al. |
| 5,809,190 A * | 9/1998 | Chen ........................ 385/43 |
| 5,815,665 A | 9/1998 | Teper et al. |
| 5,815,793 A | 9/1998 | Ferguson |
| 5,826,014 A | 10/1998 | Coley et al. |
| 5,828,833 A | 10/1998 | Belville et al. |
| 5,838,436 A | 11/1998 | Hotaling et al. |
| 5,838,542 A | 11/1998 | Nelson et al. |
| 5,844,594 A | 12/1998 | Ferguson |
| 5,845,074 A | 12/1998 | Kobata |
| 5,850,449 A | 12/1998 | Mcmanis |
| 5,861,817 A | 1/1999 | Palmer et al. |
| 5,862,357 A | 1/1999 | Hagersten et al. |
| 5,864,738 A | 1/1999 | Kessler et al. |
| 5,872,987 A | 2/1999 | Wade et al. |
| 5,881,284 A | 3/1999 | Kubo |
| 5,889,989 A | 3/1999 | Robertazzi et al. |
| 5,896,499 A | 4/1999 | McKelvey |
| 5,905,429 A | 5/1999 | Hornstein et al. |
| 5,909,052 A | 6/1999 | Ohta et al. |
| 5,909,681 A | 6/1999 | Passera et al. |
| 5,917,629 A | 6/1999 | Hortensius et al. |
| 5,930,511 A | 7/1999 | Hinsley |
| 5,943,421 A * | 8/1999 | Grabon ........................ 380/269 |
| 5,964,832 A | 10/1999 | Kisor |
| 5,978,829 A | 11/1999 | Chung et al. |
| 6,052,555 A | 4/2000 | Ferguson |
| 6,067,082 A | 5/2000 | Enmei |
| 6,073,209 A | 6/2000 | Bergsten |
| 6,098,091 A | 8/2000 | Kisor |
| 6,112,225 A | 8/2000 | Kraft et al. |
| 6,112,243 A | 8/2000 | Downs et al. |
| 6,115,698 A | 9/2000 | Tuck et al. ..................... 705/37 |
| 6,167,428 A | 12/2000 | Ellis |
| 6,208,634 B1 | 3/2001 | Boulos et al. |
| 6,219,627 B1 | 4/2001 | Bonneau et al. |
| 6,287,949 B1 | 9/2001 | Mori et al. |
| 6,440,775 B2 | 8/2002 | Khoury |
| 6,725,250 B1 | 4/2004 | Ellis |
| 6,732,141 B2 * | 5/2004 | Ellis ........................ 709/201 |
| 6,950,947 B1 | 9/2005 | Purtell et al. |
| 7,024,449 B1 | 4/2006 | Ellis |

FOREIGN PATENT DOCUMENTS

| | | |
|---|---|---|
| EP | 0 647 052 | 4/1995 |
| EP | 0 840216 A2 | 5/1998 |
| EP | 0 853 279 | 7/1998 |
| EP | 0-853-279 | 7/1998 |
| WO | WO 94/01964 | 1/1994 |
| WO | WO 95/01060 | 1/1995 |
| WO | WO 98/26366 | 6/1998 |
| WO | WO 99/04561 | 1/1999 |
| WO | WO 99/32972 | 7/1999 |

OTHER PUBLICATIONS

Steinert-Threlkeld; New Breed of Chip TI develops a super circuit; May 4, 1992; The Sun, Baltimore, Md.*

Dallas Morning News; "LSI holds big plans for tiny chips Versatility of 'system on a chip' creates niche in micrelectronics;" Mar. 4, 1996.*

Mokhoff; "System-on-a-chip comes to wireless arena;" Electronic Engineering Times; Feb. 12, 1996.*

Cindi; "'System on a Chip' stars at ISSCC;" Electronic News; Feb 12, 1996.*

Ang; "System-on-a-chip to define next-gernation set-top box; Electronic Engineering Times;" Dec. 15, 1995.*

Marc; "New family of microprocessor cores from LSI Logic extends customers' system-on-achip design capability;" Nov. 7, 1994.*

Wall Street Journal; "Technology Brief–Advanced Micro Devices Inc.: Company unveils Microchip for Hand-Held Computer;" Oct. 18, 1993.*

Ellis, U.S. Appl. No. 09/669,730, filed Sep. 26, 2000.
Ellis, U.S. Appl. No. 09/571,558, filed May 16, 2000.
Ellis, U.S. Appl. No. 09/320,660, filed May 27, 1999.
Ellis, U.S. Appl. No. 09/315,026, filed May 20, 1999.
Ellis, U.S. Appl. No. 09/085,755, filed May 27, 1998.
Ellis, U.S. Appl. No. 08/980,058, filed Nov. 26, 1997.
Ellis, U.S. Appl. No. 09/213,875, filed Dec. 17, 1998.

"Ein-Chip-Firewall," Elektroniknet Top News, XP-002164257.

"Means for Implementing Optical Interconnections for Parallel Processors," IBM Technical Disclosure Bulletin, Apr. 1991, vol. 33, No. 11, pp. 56-58, XP 000110310.

Alexandrov et al., "SuperWeb: Research Issues in Java-Based Global Computing," Concurrency, vol. 9, No. 6, Jun. 1997, pp. 535-553.

Baratloo et al., "Charlotte: Metacomputing on the Web," 9th International Conference on Parallel and Distributed Computing Systems (PDCS), 1996, pp. 1-8.

Bevinakoppa et al., "Digital Image Compression on a Network of Transputers," Proc. of $5^{th}$ Australian Transputer & OCCAM User Group Conference, IOS Press, Amsterdam, pp. 25-32.

Blumofe, R. et al., "Scheduling Large-Scale Parallel Computations on Networks of Workstations,"Proc. Of the $3^{rd}$ IEEE Int'l Symp on High Performance Distributed Computing, pp. 96-105, Aug. 1994.

Brecht et al., "ParaWeb: Towards World-Wide Supercomputing," Proceedings of the Seventh AcM SIGOPS European Workshop, Sep. 1996, 8 pages.

Brisbin, "Shopping for Internet access," MacUser, Dec. 1994, v.10, p. 133(2).

Brown et al., Special Edition Using Netscape ™, 2 Second Edition, Que Corporation, 1995, Ch. 1-2.

Capello et al., "Market-Based Massively Parallel Internet Computing," Proceedings Third Working Conference on Massively Parallel Programming Models, 1998, pp. 118-129.

Celenk, M. et al., "Parallel Task Execution in LANs and Performance Analysis," Proc. Of the 1995 IEEE $14^{th}$ Annual Int'l Phoenix Conf. On Computers and Communications, pp. 423-429, Mar. 1995.

Chen, C. et al., "The DBC: Processing Scientific Data Over the Internet," Proc. Of the $16^{th}$ Int'l. Conf. On Distributed Computing Systems, pp. 673-679, May 1996.

Clark, H. et al., "DAWGS-A Distributed Computer Server Utilizing Idle Workstations," Proc.Of the $5^{th}$ Distributed Memory Computing Conf., IEEE, pp. 732-741, Apr. 1990.

Fogg, C., "Survey of software and hardware VLC architectures," SPIE, vol. 2186, Image and Video Compression (1994), pp. 29-37.

Fox et al., "Towards Web/Java based High Performance Distributed Computing—an Evolving Virtual Machine," www.npac.syr.edu/projects/webspace/doc/hpdc5/paper, Jun. 10, 1996, 11 pages.

Fox et al., "Towards Web/Java based High Performance Distributed Computing—an Evolving Virtual Machine," as presented at $5^{th}$ IEEE International Symposium on High Performance Distributed Computing, Aug. 6-9, 1996, 86 pages.

Fox, E., "Advances in Interactive Digital Multimedia Systems," Computer, Oct. 1991, pp. 9-21.

Gemmell et al., "Multimedia Storage Servers: a Tutorial," Computer, May 1995, pp. 40-49.

Geoffrey C. Fox and Wojtek Furmanski, Petaops and Exaops: Supercomputing on the Web, "IEEE Internet Computing,"vol. 1, No. 2 Mar.-Apr. 1997, pp. 38-46.

Gibbs, "Bandwidth, Unlimited," Scientific American, Jan. 1997, p. 41.

Gilder, "Angst and Awe on the Internet by George Gilder," Forbes ASAP, Dec. 4, 1995.

Gilder, "The Bandwidth Tidal Wave," Forbes ASAP, Dec. 5, 1994.

Hare et al., "Master the Complexities of Network Security," Internet Firewalls and Network Security, Second Edition, pp. 325-350 and 516.

Hayes, "Computing Science: Collective Wisdom," American Scientist, Mar.-Apr. 1998, pp. 1-8.

Kim, B., "ATM Network: Goals and Challenges," Communications of the ACM, Feb. 1995, vol. 38, No. 2, pp. 39-44, 109.

Kivanc Dincer and Geoffrey C. Fox, Building a World-Wide Virtual Machine Based on Web and HPCC Technologies, "Student Technical Papers," http://www.supercomp.org/sc96/proceedings/SC96PROC/DINCER/INDEX.HTM pp. 1-18.

Kremien, O., "Buying and Selling Computational Power Over the Network," Proc. Of the $4^{th}$ Int'l. Conf. On Computer Communications and Networks, IEEE, pp. 616-619, Sep. 1995.

Lindley, C., "JPEG-Like Image Compression, Part 2," Dr. Dobb's Journal, Aug. 1995, pp. 62-66, 102-105.

Lindley, C., "JPEG-Like Image Compression, Part 1," Dr. Dobb's Journal, Jul. 1995, pp. 50-58, 101-102.

Litzkow et al., "Condor-A Hunter of Idle Workstations," Proc. Of the $8^{th}$ Int'l. Conf. On Distributed Computing Systems, IEEE, pp. 104-111, Jun. 1998.

M. Hobbs and A. Goscinski, A Remote Porcess Creation and Execution Facility Supporting Parallel Execution on Distributed Systems, "IEEE 1996," pp. 92-99.

Markoff, "A New Standard to Govern PC's with Multiple Chips, Work Stations Mimicking Supercomputers," The New York Times, Oct. 28, 1997.

McHenry et al., "An FPGA-Based Coprocessor for ATM Firewalls," Field-Programmable Custom Computing Machines 1997, Apr. 16-18, 1997, pp. 30-39, XP-002157218.

Morris, J., et al., "Fault Tolerant Networks of Workstations," Proc. Of the $3^{rd}$ Int'l. Conf. On High Performance Computing, IEEE, pp. 271-276, Dec. 1996.

N/A, "Aliens on your desktop," The Economist, Apr. 18, 1998, p. 78.

N/A, "Cyber View World Wide Widgets," Scientific American, May 1997, p. 48.

N/A, "Special Report—Wonder Chips," Business Week, July 4, 1994.

N/A, "Supercomputers Divide and Conquer," The Economist, Dec. 14, 1996.

Nass, R., "Hardware-software combo could simplify MPEG real-time video compression," Electronic Design, May 3, 1993, p. 36.

Nowatzyk et al., "Are Crossbars Really Dead? The Case for Optical Multiprocessor Interconnect Systems,"Proceedings of the Annual Symposium on Computer Archtecture, ACM, vol. 22, Jun. 1995, pp. 106-115, XP 000687800.

Ozer, "Digital Video: Shot by Shot," PC Magazine, Apr. 11, 1995, pp. 104-107, 110.

Ozer, J., "Why MPEG is Hot," PC Magazine, Apr. 11, 1995, pp. 130-131.

Plotkin, "The Digital Compression Facility-A Solution to Today's Compression Needs," 1994 IEEE, pp. 445-449.

Qiao et al., "Time-Division Optical Communications in Multiprocessor Arrays," ACM, 1991, pp. 644-653, XP 000337522.

Rincon et al., "The Changing Landscape of System-on-a-Chip Design," MicroNews, Third Quarter 1999, www.chips.ibm.com/micronews/vol5_no3/rincon.html, pp. 1-10, vol. 5, No. 3.

Sachs, M. et al., "LAN and I/O Convergence: A Survey of the Issues," Computer, Dec. 1994, pp. 24-32.

Sakano, M. et al., "A Three-Dimensional Mesh Multiprocessor System Using Board-to-Board Free-Space Optical Interconnects: COSINE-III," IEEE, 1993, pp. 278-283, XP 000463415.

Schroeder, E., "New offerings buoy MPEG as video standard," Desktop Computing, PC Week, May 8, 1995, pp. 1&29.

Shen et al., "A Parallel Implementation of an MPEG1 Encoder: Faster than Real-Time!", Proc. Of SPIE Conf. On Digital Video Compression, San Jose, CA, Feb. 1995.

Shiuan, J. et al., "Client-Server Based Ray-Tracer Using ASTRA: An Asynchronous RPC Mechanism," Computer Communications, vol. 19, No. 5, pp. 445-455, May 1996.

Steven M. Bellovin and William R. Cheswick, Network Firewalls, "IEEE Communications Magazine 1994," pp. 50-57.

Sullivan et al., "A New Major SETI Project Based on Project Serendip Data and 100,000 Personal Computers." http://setiathome.ss/.berkeley.edu/woody_paper.htm/.

Szabo, B., et al., "Design considerations for JPEG Video and Synchronized Audio in a Unix Workstation Environment," USENIX-Summer '91, pp. 353-368.

Taisuke Boku, Hiroshi Nakamura, Kisaburo Nakazawa, and Yoichi Iwasaki, The Architecture of Massively Parallel Processor CP-PACS, "IEEE 1997,"pp. 31-40.

Tandiary et al., "Batrun: Utilizing Idle Workstations for Large-Scale Computing," Summer 1996, pp. 41-48.

Theimer et al., "Finding Idle Machines in a Workstation-Based Distributed System," IEEE Trans. On Software Engineering, vol. 15, No. 11, pp. 1444-1458, Nov. 1989.

Vetter, R., "ATM Concepts, Architectures, and Protocols," Communications of the ACM, Feb. 1995; vol. 38, No. 2, pp. 30-38, 109.

Vetter, R., et al., "Issues and Challenges in ATM Networks," Communications of the ACM, Feb. 1995; vol. 38, No. 2, pp. 28-29.

Waldspurger et al., "Spawn: A Distributed Computational Economy," IEEE Transactions on Software Engineering, vol. 18, No. 2, Feb. 1992, pp. 103-117, XP-002124500.

Weiyi et al., "Java-to-Go—Itinerative Computing Using Java," Sep. 10, 1996 http://ptolemy.eecs.berkeley.edu/dgm/javatools/java-to-go/.

Yoon-Hwa Choi and Yu-Seok Kim, A Diagnostic Network for Massively Parallel Processing Systems, "IEEE 1994," pp. 348-353.

Yoshida, J., "MPEG-2 encoders make show of force at NAB," Electronic Engineering Times, Apr. 10, 1995.

Yu, Y. et al., "Software Implementation of MPEG-II Video Encoding Using Socket Programming in LAN," SPIE vol. 2187, pp. 229-240, 1994.

Fields, Scott, "Hunting for Wasted Computing Power—New Software for Computing Networks Puts Idle PC's to Work," 1993 University of Wisconsin- Madison. Internet: http://www.cs.wise.edu/condor/doc/WiseIdea.html.

None, "PC vision: Intel unveils plans to bring PCs to vehicles", EDGE: Work Group Computing Report, EDGE Publishing, p. 1-2, (Oct. 28, 1996).

Li, Yao, "Free-space Optical Bus-based WDMA Interconnects for Parallel Computation," LEOS '92 Conference Proceedings, Lasers and Electron-Optics Society Annual Meeting, p. 588-589, (Nov. 16-19, 1992).

Dickinson et al., "An Integrated Free Space Optical Bus," 1989 IEEE International Conference on Computer Design VLSI In Computers and Processors, p. 62-65, (Oct. 2-4, 1989).

Natarajan et al, "Bi-Directional Optical Backplane Bus for General Purpose Multi-Processor," Journal of Lightwave Technology, vol. 13 (No. 6), p. 1031-1040, (Jun. 6, 1995).

Zhao et al, "General Purpose Bidirectional Optical Backplane: High Performance Bus for Multiprocessor Systems," Massively Parallel Processing Using Optical Interconnections, 2nd International Conference, p. 188-195, (Oct. 23-24, 1995).

Wu et al., "Microprocessor Control Signal Transmission through Optical Fiber," Conference Record of 1992 IEEE Industry Applications Society Annual Meeting, p. 1747-1750, (Oct. 4-9, 1992).

Waltz et al., "Make 'em pay: Billing Net Usage", MacWeek, vol. 6 (No. 27), p. 24 (2) (Dialog full text), (Jul. 27, 1992).

"The Economics of Network Billing: Network Billing and Monitoring Systems can Improve Efficiency and Cut Costs", IBM System User, vol. 14 (No. 11), p. 53 (1) (Dialog Fulltext), (Nov., 1993).

"Let Your Computer Make Money While You Sleep", Newsbytes, p. 1 (Dialog Fulltext), (August 16, 1996).

Regenold et al., "A Single-Chip Multiprocessor DSP Solution for Communication Applications", ASIC Conference and Exhibit 1994, pp. 437-440.

Geppert, L. Solid State Trend/Development, IEEE Spectrum, v. 33, iss. 1, 1996, pp. 51-55.

The American Heritage College Dictionary 4th Ed.—definition of "firewall".

White, "Covert Distributed Processing with Computer Viruses", Advances in Cryptology, Crypto 89, Springer LNCS, v. 435, pp. 616-619.

Wilkinson, et al., "Parallel Programming", Prentice Hall, 1998.

Foster et al., "The Grid: Blueprint for a New Computing Infrastructure", Morgan Kaufman Publishers, Inc., 1998.

Hwang et al., "Scalable Parallel Computing", WCB McGraw-Hill, 1998.

Patterson et al., "Computer Architecture: A Quantitative Approach" (2nd Edition), Morgan Kaufmann Publishers, Inc., 1996.

Culler et al., "Parallel Computer Architecture", Morgan Kaufmann Publishers, Inc. 1998.

Hennessy et al., "Computer Organization and Design", Morgan Kauffmann Publishers, Inc., 1998.

Steinert-Threlkeld; "New Breed of Chip TI develops a super circuit"; The Sun Baltimore; May 4, 1992.

Office Action issued in copending related U.S. Appl. No. 10/802,049, dated Sep. 17, 2007.

Office Action issued in related U.S. Appl. No. 09/935,779 mailed Feb. 19, 2008.

David Pescovitz, "Power of the PC", Scientific American, pp. 27-28 (Apr. 2000).

Stephen H. Wildstrom, "The Problem with Firewalls", Business Week, pp. 25 (Mar. 20, 2000).

J. McH., "Build Your Own Supercomputer", Forbes, pp. 228 (Nov. 15, 1999).

Office Action issued in related copending U.S. Appl. No. 09/085,755, mailed Dec. 12, 2007.

Final Office Action issued in U.S. Appl. No. 10/802,049 mailed Jul. 3, 2008.

Notice of Allowance issued in U.S. Appl. No. 09/935,779 mailed Jul. 18, 2008.

Notice of Allowance issued in U.S. Appl. No. 09/085,755 mailed Jun. 25, 2008.

Wilkinson, Barry et al., "Parallel Programming: Techniques and Applications Using Networked Workstations and Parallel Computers", Chapter 4, Prentice-Hall, Inc., 1999.

Baker, Lou et. al., "Parallel Programming", Chapter 4, McGraw Hill Companies, Inc., 1996.

Office Action issued in U.S. Appl. No. 10/663,911, mailed Sep. 26, 2008.

A. Kayssi et al., "FPGA-based Internet Protocol Firewall Chip", Electronics, Circuits and Systems, 2000. ICES 2000. The 7th IEEE International Conference on vol. 1, pp. 316-319, Dec. 17- 20, 2000.

Notice of Allowance issued in U.S.Appl. No. 09/935,779, mailed Jan. 21, 2009.

English language abstract of EP 0 647 052, published Apr. 5, 1995.

Newton's Telecom Dictionary, "Mobile IP", p. 459, Mar. 1998.

Holographic Quantum Computer, http://www.unitelnw.com/holo1/index (May 1999).

Jonathan Fahey, "Screen Grab", FORBES, pp. 52-53, Mar. 5, 2001.

Ronald Gover et al., "TV Guy", Business Week, pp. 66-76, Mar. 12, 2001.

"Distributed Computing", Red Herring, No. 87, pp. 166-202, Dec. 18, 2000.

Om Malik, "Distributed Computing Redefines Computer Networks, Underpinning Innovation, Company Formation, and Investments", Red Herring, No. 86, pp. 95-96 and 105, Dec. 4, 2000.

Alan Zeichick, "P2P Nework Expalined", Red Herring, No. 86, pp. 204 and 206, Dec. 4, 2000 .

"Napster is Clouding Grove's Crystal Ball"; FORTUNE, pp. 271-272, May 29, 2000.

Notice of Allowance issued in U.S. Appl. No. 09/085,755 mailed Apr. 8, 2009.

None, "PC vision: Intel unveils plans to bring PCs to vehicles", EDGE: Work Group Computing Report, EDGE Publishing, p. 1-2, (Oct. 28, 1996).

Li, Yao, "Free-spcae Optical Bus-based WDMA Interconncets for Parallel Computation," LEOS '92 Conference Proceedings, Lasers and Electron-Optics Society Annual Meeting, p. 588-589, (Nov. 16-19, 1992).

Dickinson et al., "An Integrated Free Space Optical Bus," 1989 IEEE International Conference on Computer Design VLSI In Computers and Processors, p. 62-65. (Oct. 2-4, 1989).

Natarajan et al., "Bi-Directional Optical Backplane Bus for general Multi-Processor," Journal of Lightwave Technology, vol. 13, (No. 6), p. 1031-1040, (Jun. 6, 1995).

Zhao et al., "General Purpose Bidirectional Optical Backplane: High Performance Bus for Multiprocessor Systems," Massively Parallel Processing Using Optical Interconnections, 2nd International Conference, p. 188-195, (Oct. 23-24, 1995).

Wu et al., "Microprocessor Control Signal Transmission through Optical Fiber," Conference Record of 1992 IEEE Industry Applications Society Annual Meeting, p. 1747-1750, (Oct. 4-9, 1992).

* cited by examiner

INTERNAL HARDWARE FIREWALLS FOR MICROCHIPS

This application is a continuation of U.S. patent application Ser. No. 09/315,026, filed May 20, 1999, now U.S. Pat. No. 7,024,449, which receives the benefit of priority from provisional applications 60/134,552, filed May 17, 1999, 60/086,516, filed May 22, 1998, 60/086,588 filed May 22, 1998, 60/086,948, filed May 27, 1998, 60/087,587, filed Jun. 1, 1998, and 60/088,459, filed Jun. 8, 1998. U.S. patent application Ser. No. 09/315,026 is a continuation-in-part of U.S. patent application Ser. No. 09/213,875, filed Dec. 17, 1998, now U.S. Pat. No. 6,725,250, which receives the benefit of priority of provisional application 60/068,366, filed Dec. 19, 1997, and which is a continuation-in-part of U.S. patent application Ser. No. 08/980,058, filed Nov. 26, 1997, now U.S. Pat. No. 6,732,141, which receives the benefit of priority of provisional application 60/066,415, filed Nov. 24, 1997, provisional application 60/066,313, filed Nov. 21, 1997, provisional application 60/033,871, filed Dec. 20, 1996, provisional application 60/032,207 filed Dec. 2, 1996, and provisional application 60/031,855, filed Nov. 29, 1996. U.S. patent application Ser. No. 09/315,026 is also a continuation-in-part of PCT application PCT/US98/27058, filed Dec. 17, 1998 and designating the United States. PCT/US98/27058 receives the benefit of provisional application 60/068,366, filed Dec. 19, 1997. U.S. patent application Ser. No. 09/315,026 is also a continuation-in part of PCT application PCT/US97/21812, filed Nov. 28, 1997 and designating the United States. PCT/US97/21812 receives the benefit of priority of provisional application 60/066,415, filed Nov. 24, 1997, provisional application 60/066,313, filed Nov. 21, 1997, provisional application 60/033,871, filed Dec. 20, 1996, provisional application 60/032,207 filed Dec. 2, 1996, and provisional application 60/031,855, filed Nov. 29, 1996. PCT/US97/21812 is a continuation-in-part of U.S. patent application Ser. No. 08/980,058, whose priority is discussed above. U.S. patent application Ser. No. 09/315,026 is also a continuation-in-part of U.S. patent application Ser. No. 09/085,755, filed May 21, 1998. U.S. patent application Ser. No. 09/085,755, filed May 27, 1998, receives the benefit of priority of provisional application 60/066,313, filed Nov. 21, 1997, provisional application 60/066,415, filed Nov. 24, 1997, provisional application 60/068,366, filed Dec. 19, 1997, provisional application 60/086,516, filed May 22, 1998, provisional application 60/086,588, filed May 22, 1998, and provisional application 60/086,948, filed May 27, 1998.

BACKGROUND OF THE INVENTION

This invention generally relates to one or more computer networks having computers like personal computers or network computers such as servers with microprocessors preferably linked by broadband transmission means and having hardware, software, firmware, and other means such that at least two parallel processing operations occur that involve at least two sets of computers in the network or in networks connected together, a form of metacomputing. More particularly, this invention relates to one or more large networks composed of smaller networks and large numbers of computers connected, like the Internet, wherein more than one separate parallel or massively parallel processing operation involving more than one different set of computers occurs simultaneously. Even more particularly, this invention relates to one or more such networks wherein more than one (or a very large number of) parallel or massively parallel microprocessing processing operations occur separately or in an interrelated fashion; and wherein ongoing network processing linkages are established between virtually any microprocessors of separate computers connected to the network.

Still more particularly, this invention relates generally to a network structure or architecture that enables the shared used of network microprocessors for parallel processing, including massive parallel processing, and other shared processing such as multitasking, wherein personal computer owners provide microprocessor processing power to a network, preferably for parallel or massively parallel processing or multitasking, in exchange for network linkage to other personal and other computers supplied by network providers such as Internet Service Providers (ISP's), including linkage to other microprocessors for parallel or other processing such as multitasking. The financial basis of the shared use between owners and providers being be whatever terms to which the parties agree, subject to governing laws, regulations, or rules, including payment from either party to the other based on periodic measurement of net use or provision of processing power like a deregulated electrical power grid or preferably involving no payment, with the network system (software, hardware, etc) providing an essentially equivalent usage of computing resources by both users and providers (since any network computer operated by either entity is potentially both a user and provider of computing resources alternately (or even simultaneously, assuming multitasking), with potentially an override option by a user (exercised on the basis, for example, of user profile or user's credit line or through relatively instant payment).

Finally, this invention relates to a network system architecture including hardware and software that provides use of the Internet or its future equivalents or successors (and most other networks) without cost to most users of personal computers or most other computers, while also providing those users (and all other users, including of supercomputers) with computer processing performance that at least doubles every 18 months through metacomputing means. This metacomputing performance increase provided by the new MetaInternet (or Metanet for short) is in addition to all other performance increases, such as those already anticipated by Moore's Law.

By way of background, the computer industry has been governed over the last 30 years by Moore's Law, which holds that the circuitry of computer chips has been shrunk substantially each year, yielding a new generation of chips every 18 months with twice as many transistors, so that microprocessor computing power is effectively doubled every year and a half.

The long term trend in computer chip miniaturization is projected to continue unabated over the next few decades. For example, slightly more than a decade ago a 16 kilobit DRAM memory chip (storing 16,000 data bits) was typical; the standard in 1996 was the 16 megabit chip (16,000,000 data bits), which was introduced in 1993; and industry projections are for 16 gigabit memory chips (16,000,000,000 data bits) to be introduced in 2008 and 64 gigabit chips in 2011, with 16 terabit chips (16,000,000,000,000 data bits) conceivable by the mid-to-late 2020's. This is a thousand-fold increase regularly every fifteen years. Hard drive speed and capacity are also growing at a spectacular rate, even higher than that of semiconductor microchips in recent years.

Similarly regular and enormous improvements are anticipated to continue in microprocessor computing speeds, whether measured in simple clock speed or MIPS (millions of instructions for second) or numbers of transistors per chip. For example, performance has improved by four or five times every three years since Intel launched its X86 family of microprocessors used in the currently dominant "Wintel" standard personal computers. The initial Intel Pentium Pro microprocessor was introduced in 1995 and is a thousand times faster than the first IBM standard PC microprocessor, the Intel 8088, which was introduced in 1979. By 1996 the fastest of microprocessors, like Digital Equipment Corp.'s Alpha chip, is faster than the processor in the original Cray Y-MP supercomputer, as is even the Nintendo 64 video game system.

Both microprocessors and software (and firmware and other components) are also evolving from 8 bit and 16 bit systems into 32 bit systems that are becoming the standard today, with some 64 bit systems like the DEC Alpha already introduced and more coming, such as Intel's Merced microprocessor in 2000, with future increases to 128 bit likely some later.

A second major development trend in the past decade or so has been the rise of parallel processing, a computer architecture utilizing more than one CPU microprocessor (often many more, even thousands of relatively simple microprocessors, for massively parallel processing) linked together into a single computer with new operating systems having modifications that allow such an approach. The field of supercomputing has been taken over by this approach, including designs utilizing many identical standard personal computer microprocessors.

Hardware, firmware, software and other components specific to parallel processing are in a relatively early stage of development compared to that for single processor computing, and therefore much further design and development is expected in the future to better maximize the computing capacity made possible by parallel processing. Continued improvement is anticipated in system hardware, software, and architecture for parallel processing so that reliance is reduced on the multiple microprocessors having to share a common central memory, thereby allowing more independent operation of those microprocessors, each with their own discrete memory, like current personal computers, workstations and most other computer systems architecture; for unconstrained operation, each individual microprocessor must have rapid access to sufficient memory.

Several models of personal computers are now available with more than one microprocessor. It seems inevitable that in the future personal computers, broadly defined to include versions not currently in use, will also employ parallel computing utilizing multiple microprocessors or massively parallel computing with very large numbers of microprocessors. Future designs, such Intel's Merced chip, are expected to have a significant number of parallel processors on a single microprocessor chip.

A form of parallel processing called superscalar processing is also being employed within microprocessor design itself. The current generation of microprocessors such at the Intel Pentium have more than one data path within the microprocessor in which data is processed, with two to three paths being typical now and as many as eight in 1998 in IBM's new Power 3 microprocessor chip.

The third major development trend is the increasing size of bandwidth, which is a measure of communications power or transmission speed (in terms of units of data per second) between computers connected by a network. Before now, the local area networks and telephone lines typically linking computers including personal computers have operated at speeds much lower than the processing speeds of a personal computer. For example, a typical 1997 Intel Pentium operates at 100 MIPS (millions of instructions per second), whereas the most common current Ethernet connecting PC's is roughly 10 times slower at 10 megabits per second (Mbps), although some Ethernet connections are now 100 Mbps) and telephone lines are very much slower, the highest typical speed in 1998 being about 56 kilobits (reached only during downloads, however).

Now, however, the situation is expected to change dramatically, with bandwidth or transmission speed being anticipated to expand from 5 to 100 times as fast as the rise of microprocessor speeds, due to the use of coaxial cable, wireless, and especially fiber optic cable, instead of old telephone twisted pair lines. Telecommunication providers are now making available fiber connections supporting bandwidth of 40 gigabits and higher.

Technical improvements are expected in the near term which will make it possible to carry over 2 gigahertz (billions of cycles per second) on each of 700 wavelength streams, adding up to more than 1,400 gigahertz on every single fiber thread. Experts currently estimate that the bandwidth of optical fiber has been utilized one million times less fully than the bandwidth of coaxial or twisted pair copper lines. Within a decade, 10,000 wavelength streams per fiber are expected and 20-80 wavelengths on a single fiber is already commercially available. And the use of thin mirrored hollow wires or tubes called omniguides should provide very substantial additional increases.

Other network connection developments such as asynchronous transfer mode (ATM) and digital signal processors, which are improving their price/performance tenfold every two years, are also supporting the rapid increase in bandwidth. The increase in bandwidth reduces the need for switching and switching speed will be greatly enhanced when practical optical switches are introduced in the fairly near future, potentially reducing costs substantially.

The result of this huge bandwidth increase is extraordinary: already it is technically possible to connect virtually any computer to a network with a bandwidth that equals or exceeds the computer's own internal system bus speed, even as that bus speed itself is increasing significantly. The principal constraint is the infrastructure, consisting mostly of connecting the "last mile" to personal computers with optical fiber or other broad bandwidth connection, still needs to be built. The system bus of a computer is its internal network connecting many or most of its internal components such as microprocessor, random access memory (RAM), hard-drive, modem, floppy drive, and CD-ROM; for recent personal computers it has been only about 40 megabits per second, but is up to 133 megabits per second on Intel's Pentium PCI bus in 1995. IBM's 1998 Power3 microprocessor chip has a system bus of 1.6 gigabits per second and is now up to a gigabit per second on Intel's Pentium PCI bus.

Despite these tremendous improvements anticipated in the future, the unfortunate present reality is that a typical personal computer (PC) is already so fast that its microprocessor is essentially idle during most of the time the PC is in actual use and that operating time itself is but a small fraction of those days the PC is even in any use at all. The reality is that nearly all PC's are essentially idle during roughly all of their useful life. A realistic estimate is that its microprocessor is in an idle state 99.9% of the time (disregarding current unnecessary microprocessor busywork like executing screen saver programs, which have been made essentially obsolete by power-saving CRT monitor technology, which is now standard in the PC industry).

Given the fact that the reliability of PC's is so exceptionally high now, with the mean time to failure of all components typically several hundred thousand hours or more, the huge idle time of PC's represents a total loss; given the high capital and operating costs of PC's, the economic loss is very high. PC idle time does not in effect store a PC, saving it for future use, since the principle limiting factor to continued use of today's PC's is obsolescence, not equipment failure from use.

Moreover, there is growing concern that Moore's Law, which as noted above holds that the constant miniaturization of circuits results in a doubling of computing power every 18 months, cannot continue to hold true much longer. Indeed, Moore's Law may now be nearing its limits for silicon-based devices, perhaps by as early as 2004, and no new technologies have yet emerged that currently seem with reasonable certainty to have the potential for development to a practical level by then, although many recent advances have the potential to maintain Moore's Law.

SUMMARY OF THE INVENTION

However, the confluence of all three of the established major trends summarized above—supercomputer-like personal computers, the spread of parallel processing using personal computer microprocessors (particularly massively parallel processing), and the enormous increase in network communications bandwidth—has made possible a surprising solution to the hugely excessive idleness problem of personal computers (and to the problematic possible end of Moore's Law), with very high potential economic savings once the basic infrastructure connecting personal computers with optical fiber is in place in the relatively near future.

The solution is use those mostly idle PC's (or their equivalents or successors) to build a parallel or massively parallel processing computer utilizing a very large network like the Internet or, more specifically, like the World Wide Web (WWW), or their equivalents or eventual successors like the MetaInternet (and including Internet II and the Next Generation Internet, which are under development now and which will utilize much broader bandwidth and will coexist with the Internet, the structure of which is in ever constant hardware and software upgrade and including the SuperInternet based on essentially all optical fiber transmission) with extremely broad bandwidth connections and virtually unlimited data transmission speed.

The prime characteristic of the Internet is of course the very large number of computers of all sorts already linked to it, with the future potential for effectively universal connection; it is a network of networks of computers that provides nearly unrestricted access (other than cost) worldwide. The soon-to-be widely available very broad bandwidth of network communications is used to link personal computers externally in a manner at least equivalent, and probably much faster, to the faster internal system buses of the personal computers, so that no external processing constraint will be imposed on linked personal computers by data input or output, or throughput; the speed of the microprocessor itself is the only processing constraint of the system.

This makes efficient external parallel processing possible, including massively parallel processing, in a manner paralleling more conventional internal parallel processing, call superscalar processing.

In one preferred embodiment, the World Wide Web (or its equivalents or successors) is transformed into a huge virtual massively parallel processing computer or computers, with potential through its established hyperlinks connections to operate in a manner at least somewhat like a neural network or neural networks, since the speed of transmission in the broadband linkages is so great that any linkage between two microprocessors is virtually equivalent to direct, physically close connections between those microprocessors.

With further development, digital signal processor-type microprocessors and/or analogue microprocessors may be particularly advantageous for this approach, either alone or in conjunction with conventional microprocessors and/or those new microprocessors described in this application. Networks with WWW-type hyperlinks incorporating digital signal processor-type microprocessor (or successors or equivalents) could operate separately from networks of conventional microprocessors (or successors or equivalents) or with one or more connections between such differing networks or with relatively complete integration between such differing networks. Simultaneous operation across the same network connection structure should be possible, employing non-interfering transmission links.

Such extremely broad bandwidth networks of computers enable every PC within the network to be fully utilized or nearly so. Because of the extraordinary extent to which existing PC's are currently idle, at optimal performance this new system potentially results in a thousand-fold increase in computer power available to each and every PC user (and any other user); and, on demand, almost any desired level of increased power, limited mostly by the increased cost, which however is relatively far less than possible from any other conceivable computer network configuration. This revolutionary increase is on top of the extremely rapid, but evolutionary increases already occurring in the computer/network industry discussed above.

The metacomputing hardware and software means of the MetaInternet provides performance increases that is likely to at least double every eighteen months based on the doubling of personal computers shared in a typical parallel processing operation by a standard PC user, starting first with at least 2 PC's, then about 4, about 8, about 16, about 32, about 64, about 128, about 256, and about 512, for example. After about fifteen years, for example, it is anticipated that each standard PC user will likely be able to use about 1024 personal computers for parallel processing or any other shared computing use, while generally using the Internet or its successors like the MetaInternet for free. At the other end of the performance spectrum, supercomputers experience a similar performance increase generally, but ultimately the performance increase is limited primarily by cost of adding temporary network linkages to available PC's, so there is definite potential for a quantum leap in supercomputer performance.

Network computer systems as described above offer almost limitless flexibility due to the abundant supply of heretofore idle connected microprocessors. This advantage allows "tightly coupled" computing problems (which normally are difficult to process in parallel) to be solved without knowing in advance (as is now necessary in relatively massively parallel processing) how many processors are available, what they are and their connection characteristics. A minimum number of equivalent processors (with equivalent other specs) are easily found nearby in a massive network like the Internet and assigned within the network from those multitudes available nearby. Moreover, the number of microprocessors used are almost completely flexible, depending on the complexity of the problem, and limited only by cost. The existing problem of time delay is solved largely by the widespread introduction of broad bandwidth connections between computers processing in parallel.

The state of the known art relating to this application is summarized in *The Grid: Blueprint for a New Computing Infrastructure*, edited by Ian Foster and Carl Kesselman, and published by Morgan Kaufman Publishers, Inc. in July 1998. Additional information may be obtained from the World Wide Web at "http://www.mkp.com/grids".

DETAILED DESCRIPTION OF THE PREFERRED EMBODIMENTS

Figure 1:
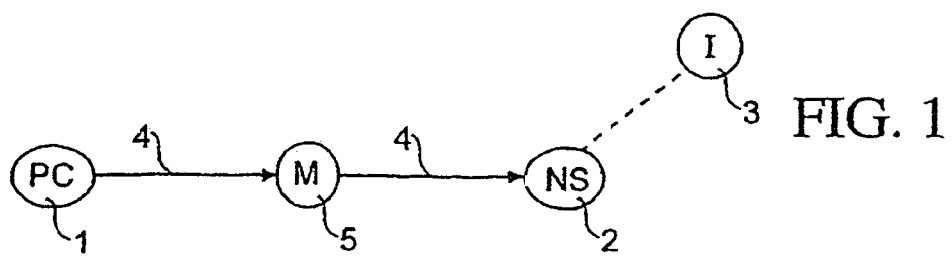
FIG. 1 is a simplified diagram of a section of a computer network, such as the Internet, showing an embodiment of a meter means which measures flow of computing during a shared operation such as parallel processing between a typical PC user and a network provider.

The new network computer utilizes PC's as providers of computing power to the network, not just users of network services. These connections between network and personal computer are enabled by a new form of computer/network financial structure that is rooted on the fact that economic resources being provided the network by PC owners (or leaser) are similar in value to those being provided by the network provider providing connectivity.

Unlike existing one way functional relationships between network providers such as internet service providers (often currently utilizing telecommunications networks for connectivity) and PC users, wherein the network provider provides access to a network like the Internet for a fee (much like cable TV services), this new relationship recognizes that the PC user is also providing the network access to the user's PC for parallel computing use, which has a similar value. The PC thus both provides and uses services on the network, alternatively or potentially even virtually simultaneously, in a multitasking mode.

This new network operates with a structural relationship that is roughly like that which presently exists between an electrical power utility and a small independent power generator connected to a deregulated utility's electrical power grid, wherein electrical power can flow in either direction between utility and independent generator depending on the operating decisions of both parties and at any particular point in time each party is in either a debt or credit position relative to the other based on the net direction of that flow for a given period, and is billed accordingly. In the increasingly deregulated electrical power industry, electrical power (both its creation and transmission) is becoming a commodity bought and sold in a competitive marketplace that crosses traditional borders. With the structural relationship proposed here for the new network, parallel free market structures can develop over time in a new computer power industry dominated by networks of personal computers in all their forms providing shared processing in a grid scaling almost seamlessly from local to national (and international) like an open market electrical power grid.

For this new network and its structural relationships, a network provider or Internet service provider (ISP) is defined in the broadest possible way as any entity (corporation or other business, government, not-for-profit, cooperative, consortium, committee, association, community, or other organization or individual) that provides personal computer users (very broadly defined below) with initial and continuing connection hardware and/or software and/or firmware and/or other components and/or services to any network, such as the Internet and WWW or Internet II or Next Generation Internet or their present or future equivalents, coexistors or successors, like the herein proposed MetaInternet, including any of the current types of Internet access providers (ISP's) including telecommunication companies, television cable or broadcast companies, electrical power utilities or other related companies, satellite communications companies, or their present or future equivalents, coexistors or successors.

The connection means used in the networks of the network providers, including between personal computers or equivalents or successors, is preferably very broad bandwidth, including electromagnetic connections such as optical connection, including fiber optic cable or wireless for example, but not excluding any other electromagnetic or other means, including television coaxial cable and telephone twisted pair, as well as associated gateways, bridges, routers, and switches with all associated hardware and/or software and/or firmware and/or other components and their present or future equivalents or successors. The computers used by the providers include any current or future computers, including such current examples as mainframes, minicomputers, servers, and personal computers, and associated their associated hardware and/or software and/or firmware and/or other components, and their present or future equivalents or successors.

Other levels of network control beyond the network provider also exist to control any aspect of the network structure and function, any one of which levels may or may not control and interact directly with the PC user. For example, at least one level of network control like the World Wide Web Consortium (W3C) or Internet Society (ISOC) or other ad hoc industry consortia establish and ensure compliance with any prescribed network standards and/or protocols and/or industry standard agreements for any hardware and/or software and/or firmware and/or other component connected to the network. Under the consensus control of these consortia/societies, other levels of network control can deal with administration and operation of the network. These other levels of network control can potentially be constituted by any network entity, including those defined immediately above for network providers.

The principal defining characteristic of the network herein described being communication connections (including hardware and/or software and/or firmware and/or other component) of any form, including electromagnetic (such as light and radio or microwaves) and electrochemical (and not excluding biochemical or biological), between PC users and their computers, with connection (either directly or indirectly) to the largest number of users and their computers possible being highly advantageous, such as networks like the Internet (and Internet II and the Next Generation Internet) and WWW and equivalents and successors, like the MetaInternet. Multiple levels of such networks will likely coexist with different technical capabilities, like Internet and Internet II, but would certainly have interconnection and therefore would certainly communicate freely between levels, for such standard network functions as electronic mail, for example.

And a personal computer (PC) user is defined in the broadest possible way as any individual or other entity routinely using a personal computer, which is defined as any computer, digital or analog or neural or quantum, particularly including personal use microprocessor-based personal computers having one or more microprocessors (each including one or more parallel processors) in their general current form (hardware and/or software and/or firmware and/or any other component) and their present and future equivalents or successors, such as application-specific (or several application) computers, network computers, handheld personal digital assistants, personal communicators such as telephones and pagers, wearable computers, digital signal processors, neural-based computers (including PC's), entertainment devices such as televisions and associated cable digital set-top control boxes, video tape recorders, video games, videocams, compact or digital video disk (CD or DVD) player/recorders, radios and cameras, other household electronic devices, business electronic devices such as printers, copiers, fax machines, automobile or other transportation equipment devices, robots, and other current or successor devices incorporating one or more microprocessors (or functional or structural equivalents), especially those owned (or leased directly or indirectly) and used directly by individuals, utilizing one or more microprocessors, made of inorganic compounds such as silicon and/or other inorganic or organic compounds. While not personal computers (due generally to high cost), current and future forms of mainframe computers, minicomputers, workstations, and even supercomputers are also be included with PCs in a parallel processing network, since they can be used functionally in the same general way in the network as a PC. Such personal computers as defined above have owners or Teasers, which may or may not be the same as the computer users. Continuous connection of computers to the network, such as the Internet, WWW, or equivalents or successors, is preferred, but clearly not required, since connection can also be made at the initiation of a shared processing operation.

Parallel processing is defined as one form of shared processing involving two or more microprocessors used in solving the same computational problem or other task. Massively parallel microprocessor processing involves large numbers of microprocessors. In today's technology, massive parallel processing is probably to be considered to be about 64 microprocessors (referred to in this context as nodes) and over 7,000 nodes have been successfully tested in an Intel supercomputer design using PC microprocessors (Pentium Pros).

It is anticipated that continued software improvements will make possible effective use of a much larger number of nodes, very possibly limited only by the number of microprocessors available for use on a given network, even an extraordinarily large one like the Internet or its equivalents and/or successors, like the MetaInternet.

Broadband wavelength or broad bandwidth network transmission is defined here to mean a transmission speed (usually measured in bits per second) that is at least high enough (or roughly at least equivalent to the internal clock speed of the microprocessor or microprocessors times the number of microprocessor channels equaling instructions per second or operations per second or calculations per second) so that the processing input and output of the microprocessor is substantially unrestricted, particularly including at peak processing levels, by the bandwidth of the network connections between microprocessors that are performing some form of parallel processing, particularly including massive parallel processing. Since this definition is dependent on microprocessor speed, it increases as microprocessor speeds increase. A rough example might be a 1996 era 100 MIPS (millions instructions per second) microprocessor, for which a broad bandwidth connection is greater than 100 megabytes per second (MBps); this is a rough approximation.

However, a preferred connection means referenced above is a light wave or optical connection such as fiber optic cable, which in 1996 already provided multiple gigabit bandwidth on single fiber thread and is rapidly improving significantly on a continuing basis, so the currently preferred general use of optical fiber connections between PCs virtually assures broad bandwidth for data transmission that is far greater than microprocessor speed to provide data to be transmitted. In addition, new wired optical connections in the form of thin, mirrored hollow wires or tubes called omniguides offer even much greater bandwidth than optical fiber and without need of amplification when transmitting over distances, unlike optical fiber. The connection means to provide broad bandwidth transmission is either wired or wireless, with wireless generally preferred for mobile personal computers (or equivalents or successors) and as otherwise indicated below. Wireless connection bandwidth is also increasing rapidly and is considered to offer essentially the same benefit as fiber optic cable: data transmission speed that far exceeds data processing speed.

The financial basis of the shared use between owners/leasers and providers is whatever terms to which the parties agree, subject to governing laws, regulations, or rules, including payment from either party to the other based on periodic measurement of net use or provision of processing power, in a manner like an deregulated or open market electrical power grid.

In one embodiment, as shown in FIG. 1, in order for this network structure to function effectively, there is a meter device 5 (comprised of hardware and/or software and/or firmware and/or other component) to measure the flow of computing power between PC 1 user and network 2 provider, which might provide connection to the Internet and/or World Wide Web and/or Internet II and/or any present or future equivalent or successor 3, like the MetaInternet. In one embodiment, the PC user should be measured by some net rating of the processing power being made available to the network, such as net score on one or more standard tests measuring speed or other performance characteristics of the overall system speed, such as PC Magazine's benchmark test program, ZD Winstone (potentially including hardware and/or software and/or firmware and/or other component testing) or specific individual scores for particularly important components like the microprocessor (such as MIPS or millions of instructions per second) that may be of application-specific importance, and by the elapsed time such resources were used by the network. In the simplest case, for example, such a meter need measure only the time the PC was made available to the network for processing 4, which can be used to compare with time the PC used the network (which is already normally measured by the provider, as discussed below) to arrive at a net cost; potential locations of such a meter include at a network computer such as a server, at the PC, and at some point on the connection between the two. Throughput of data in any standard terms is another potential measure.

Figure 2:
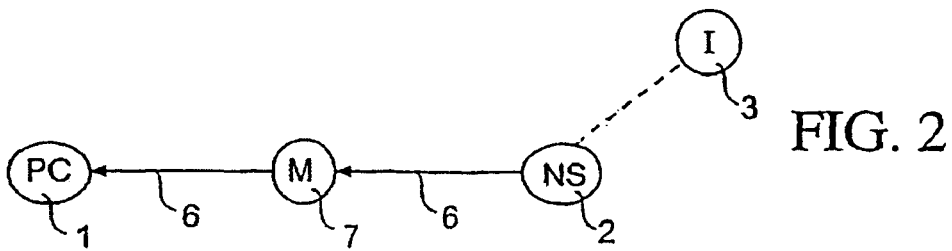
FIG. 2 is a simplified diagram of a section of a computer network, such as the Internet, showing an embodiment of another meter means which measures the flow of network resources, including shared processing, being provided to a typical PC user and a network provider.

In another embodiment, as shown in FIG. 2, there also is a meter device 7 (comprised of hardware and/or software and/or firmware and/or other component) that measures the amount of network resources 6 that are being used by each individual PC 1 user and their associated cost. This includes, for example, time spent doing conventional downloading of data from sites in the network or broadcast from the network 6. Such metering devices currently exist to support billing by the hour of service or type of service is common in the public industry, by providers such as America Online, Compuserve, and Prodigy. The capability of such existing devices is enhanced to include a measure of parallel processing resources that are allocated by the Internet Service Provider or equivalent to an individual PC user from other PC users 6, also measuring simply in time. The net difference in time 4 between the results of meter 5 and meter 7 for a given period provides a reasonable billing basis.

Figure 3:
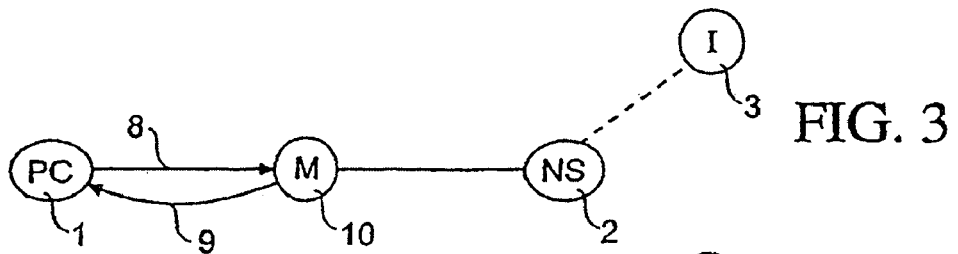
FIG. 3 is a simplified diagram of a section of a computer network, such as the Internet, showing an embodiment of another meter means which, prior to execution, estimates the level of network resources, and their cost, of a shared processing operation requested by a typical PC user from a network provider.

Alternately, as shown in FIG. 3, a meter 10 also estimates to the individual PC user prospectively the amount of network resources needed to fulfill a processing request from the PC user to the network (provider or other level of network control) and associated projected cost, provide a means of approving the estimate by executing the request, and a real-time readout of the cost as it occurs (alternatively, this meter might be done only to alert 9 the PC user that a given processing request 8 falls outside normal, previously accepted parameters, such as level of cost). To take the example of an unusually deep search request, a priority or time limit and depth of search should optimally be criteria or limiting parameters that the user can determine or set with the device.

Preferably, the network involves no payment between users and providers, with the network system (software, hardware, etc) providing an essentially equivalent usage of computing resources by both users and providers (since any network computer operated by either entity can potentially be both a user and provider of computing resources (even simultaneously, assuming multitasking), with potentially an override option by a user (exercised on the basis, for example, of user profile or user's credit line or through relatively instant payment).

Figure 4A:
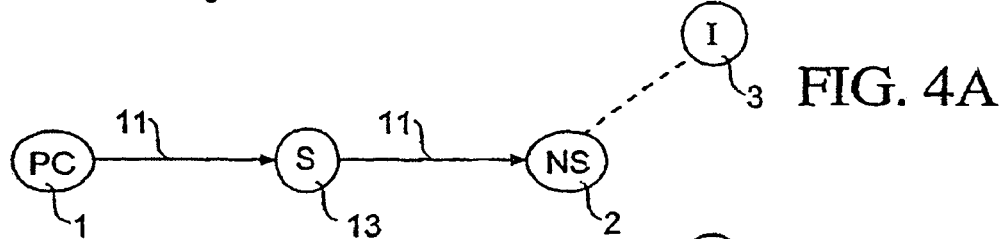
FIGS. 4A-4C are simplified diagrams of a section of a computer network, such as the Internet, showing in a sequence of steps an embodiment of a selection means whereby a shared processing request by a PC is matched with a standard preset number of other PC's to execute shared operation.
Figure 4B:
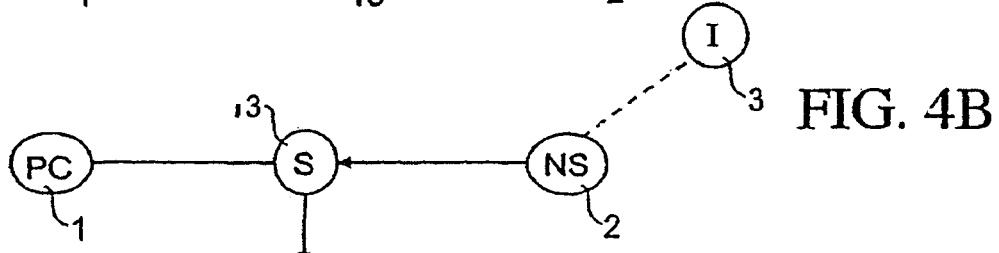
Figure 4C:
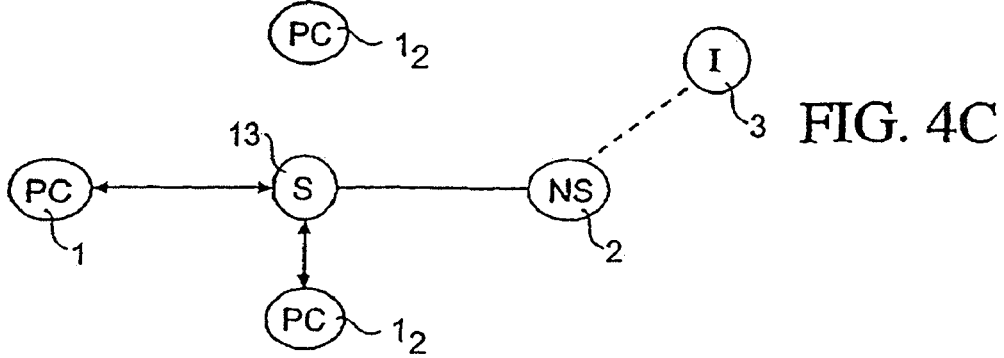

Preferably, as shown in FIGS. 4A-4C, the priority and extent of use of PC and other users can be controlled on a default-to-standard-of-class-usage basis by the network (provider or other) and overridden by the user decision on a basis prescribed by the specific network provider (or by another level of network control). One example of a default basis is to expend up to a PC's or other user's total credit balance with the provider described above and the network provider then to provide further prescribed service on an debt basis up to some set limit for the user; different users might have different limits based on resources and/or credit history.

A specific category of PC user based, for example, on specific microprocessor hardware owned or leased, might have access to a set maximum number of parallel PC's or microprocessors, with smaller or basic users generally having less access and vice versa. Specific categories of users might also have different priorities for the execution of their processing by the network. A very wide range of specific structural forms between user and provider are possible, both conventional and new, based on unique features of the new network computer system of shared processing resources.

For example, in the simplest case, in an initial system embodiment, as shown in FIG. 4A, a standard PC 1 user request 11 for a use involving parallel processing might be defaulted by system software 13, as shown in FIG. 4B, to the use of only one other essentially identical PC $1_2$ microprocessor for parallel processing or multitasking, as shown in FIG. 4C; larger standard numbers of PC microprocessors, such as about three PC's at the next level, as shown in later FIG. 10G (which could also illustrate a PC 1 user exercising an override option to use a level of services above the default standard of one PC microprocessor, presumably at extra cost), for a total of about four, then about 8, about 16, about 32, about 64 and so on, or virtually any number in between, is made available as the network system is upgraded in simple phases over time, as well as the addition of sophisticated override options. As the phase-in process continues, many more PC microprocessors can be made available to the standard PC user (virtually any number), preferably starting at about 128, then about 256, then about 512, then about 1024 and so on over time, as the network and all of its components are gradually upgraded to handle the increasing numbers. System scalability at even the standard user level is essentially unlimited over time.

Preferably, for most standard PC users (including present and future equivalents and successors), connection to the Internet (or present or future equivalents or successors like the MetaInternet) can be at no cost to PC users, since in exchange for such Internet access the PC users can generally make their PC, when idle, available to the network for shared processing. Preferably, then, competition between Internet Service Providers (including present and future equivalents and successors) for PC user customers can be over such factors as the convenience and quality of the access service provided and of shared processing provided at no addition cost to standard PC users, or on such factors as the level of shared processing in terms, for example of number of slave PC's assigned on a standard basis to a master PC. The ISP's can also compete for parallel processing operations, from inside or outside the ISP Networks, to conduct over their networks.

Figure 5A:
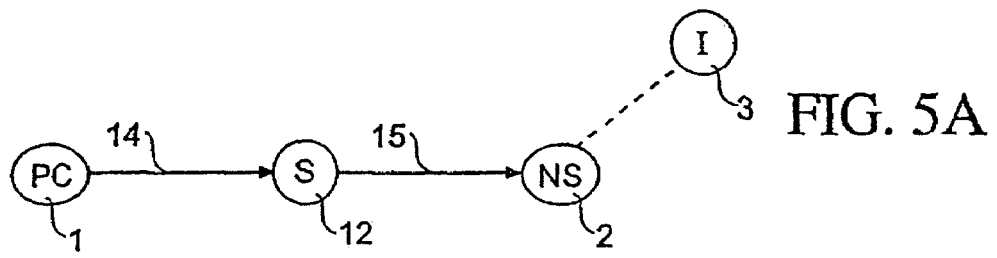
FIG. 5 is a simplified diagram of a section of a computer network, such as the Internet, showing an embodiment of a control means whereby the PC, when idled by its user, is made available to the network for shared processing operations.
Figure 5B:
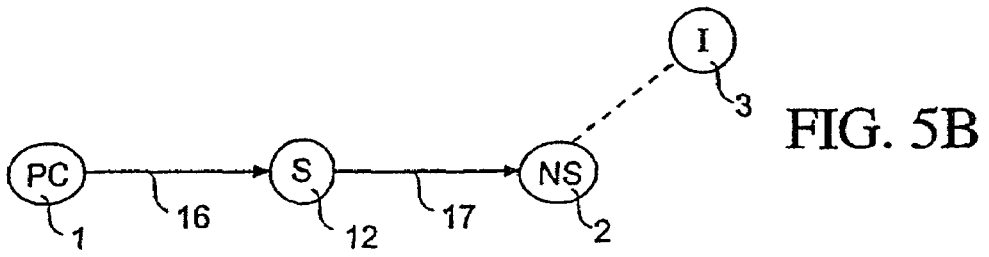

In addition, as shown in FIGS. 5A-5B, in another embodiment there is a (hardware and/or software and/or firmware and/or other) controlling device to control access to the user's PC by the network. In its simplest form, such as a manually activated electromechanical switch, the PC user could set this controller device to make the PC available to the network when not in use by the PC user. Alternatively, the PC user could set the controller device to make the PC available to the network whenever in an idle state, however momentary, by making use of multitasking hardware and/or software and/or firmware and/or other component (broadcast or "pushy" applications from the Internet or other network could still run in the desktop background).

Or, more simply, as shown in FIG. 5A, whenever the state that all user applications are closed and the PC 1 is available to the network 14 (perhaps after a time delay set by the user, like that conventionally used on screensaver software) is detected by a software controller device 12 installed in the PC, the device 12 signals 15 the network computer such as a server 2 that the PC available to the network, which could then control the PC 1 for parallel processing or multitasking by another PC. Such shared processing can continue until the device 12 detects the an application being opened 16 in the first PC (or at first use of keyboard, for quicker response, in a multitasking environment), when the device 12 signals 17 the network computer such as a server 2 that the PC is no longer available to the network, as shown in FIG. 5B, so the network can then terminate its use of the first PC.

Figure 6:
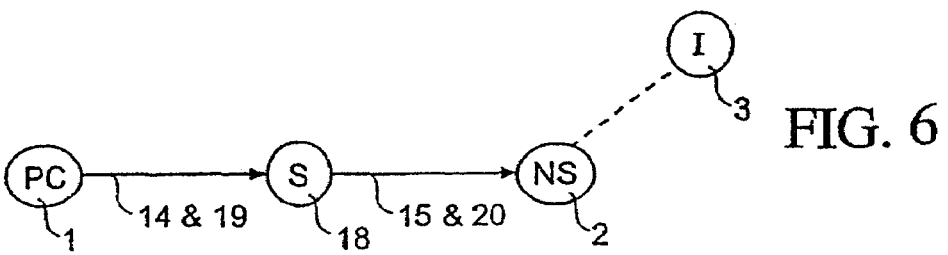
FIG. 6 is a simplified diagram of a section of a computer network, such as the Internet, showing an embodiment of a signal means whereby the PC, when idled by its user, signals its availability to the network for shared processing operations.

In a preferred embodiment, as shown in FIG. 6, there is a (hardware and/or software and/or firmware and/or other component) signaling device 18 for the PC 1 to indicate or signal 15 to the network the user PC's availability 14 for network use (and whether full use or multitasking only) as well as its specific (hardware/software/firmware/other components) configuration 20 (from a status 19 provided by the PC) in sufficient detail for the network or network computer such as a server 2 to utilize its capability effectively. In one embodiment, the transponder device is resident in the user PC and broadcast its idle state or other status (upon change or periodically, for example) or respond to a query signal from a network device.

Figure 7:
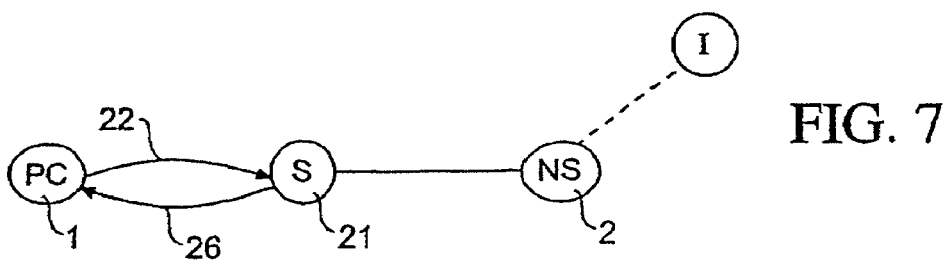
FIG. 7 is a simplified diagram of a section of a computer network, such as the Internet, showing an embodiment of a receiver and/or interrogator means whereby the network receives and/or queries the availability for shared processing status of a PC within the network.

Also, in another embodiment, as shown in FIG. 7, there is a (hardware/software and/or firmware and/or other component) transponder device 21 resident in a part of the network (such as network computer, switch, router, or another PC, for examples) that receives 22 the PC device status broadcast and/or queries 26 the PC for its status, as shown in FIG. 7.

Figure 8:
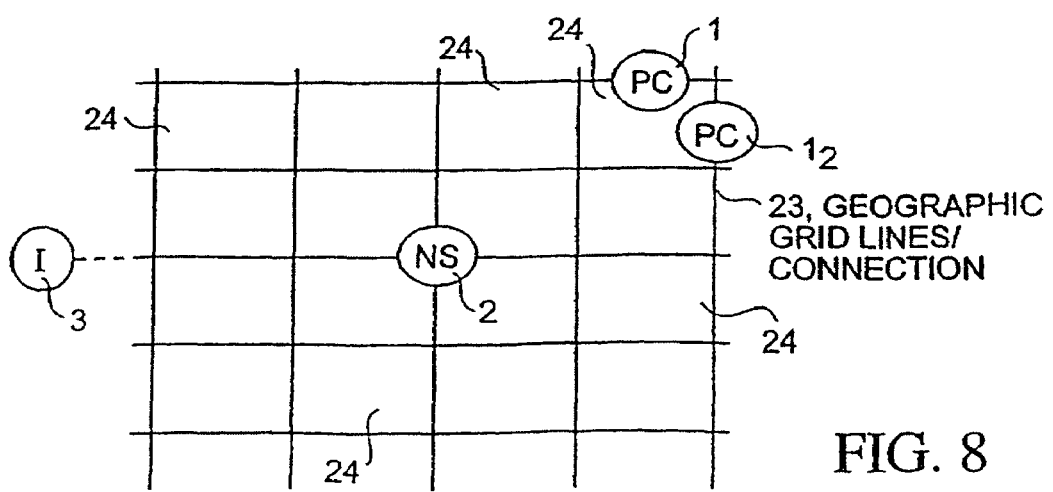
FIG. 8 is a simplified diagram of a section of a computer network, such as the Internet, showing an embodiment of a selection and/or utilization means whereby the network locates available PC's in the network that are located closest to each other for shared processing.

In one embodiment, as shown in FIG. 8, the network also has resident in a part of its hardware and/or software (and/or firmware and/or other components) a capacity such as to allow it to most effectively select and utilize the available user PC's to perform parallel processing initiated by PC users or the network providers or others. To do so, the network should have the (hardware and/or software and/or firmware and/or other component) capability of locating each PC accurately at the PC's position on the geographic grid lines/connection means 23 so that parallel processing occurs between PC's (PC 1 and PC $1_2$) as close together as possible, which should not be difficult for PC's at fixed sites with a geographic location, customarily grouped together into cells 24, as shown in FIG. 8, but which requires an active system for any wireless microprocessor to measure its distance from its network relay site, as discussed below in FIG. 14.

Figure 9:
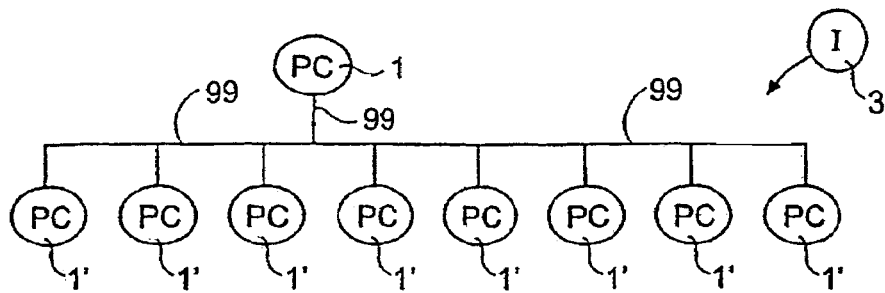
FIG. 9 is a simplified diagram of a section of a computer network, such as the Internet, showing an embodiment of a system architecture for conducting a request imitated by a PC for a search using parallel processing means that utilizes a number of networked PC's.

One of the primary capabilities of the Internet (or Internet II or successor, like the MetaInternet) or WWW network computer is to facilitate searches by the PC user or other user. As shown in FIG. 9, searches are particularly suitable to multiple processing, since, for example, a typical search is to find a specific Internet or WWW site with specific information. Such site searches can be broken up geographically, with a different PC processor 1' allocated by the network communicating through a wired means 99 as shown (or wireless connections) to search each area, the overall area being divided into eight separate parts, as shown, which are preferably about equal, so that the total search would be about ⅛ as long as if one processor did it alone (assuming the PC 1 microprocessor provides control only and not parallel processing, which may be preferable in some case).

As a typical example, a single PC user might need 1,000 minutes of search time to find what is requested, whereas the network computer, using multiple PC processors, might be able to complete the search in 100 minutes using 10 processors, or 10 minutes using 100 processors or 1 minute using 1,000 processors (or even 1 second using 60,000 processors); assuming performance transparency, which should be achievable, at least over time. The network's external parallel processing is optimally completely scalable, with virtually no theoretical limit.

The above examples also illustrates a tremendous potential benefit of network parallel processing. The same amount of network resources, 60,000 processor seconds, was expended in each of the equivalent examples. But by using relatively large multiples of processors, the network can provide the user with relatively immediate response with no difference in cost (or relatively little difference)—a major benefit. In effect, each PC user linked to the network providing external parallel processing becomes, in effect, a virtual supercomputer! As discussed below, supercomputers can experience a similar quantum leap in performance by employing a thousand-fold (or more) increase in microprocessors above current levels.

Such power will likely be required for any effective searches in the World Wide Web (WWW). WWW is currently growing at a rate such that it is doubling every year, so that searching for information within the WWW will become geometrically more difficult in future years, particularly a decade hence, and it is already a very significant difficulty to find WWW sites of relevance to any given search and then to review and analyze the contents of the site.

So the capability to search with massive parallel processing will be required to be effective and can dramatically enhance the capabilities of scientific, technological and medical researchers.

Such enhanced capabilities for searching (and analysis) can also fundamentally alter the relationship of buyers and sellers of any items and/or services. For the buyer, massive parallel network processing can make it possible to find the best price, worldwide, for any product or the most highly rated product or service (for performance, reliability, etc.) within a category or the best combination of price/performance or the highest rated product for a given price point and so on.

The best price for the product can include best price for shipping within specific delivery time parameters acceptable to the buyer.

For the seller, such parallel processing can drastically enhance the search, worldwide, for customers potentially interested in a given product or service, providing very specific targets for advertisement. Sellers, even producers, can know their customers directly and interact with them directly for feedback on specific products and services to better assess customer satisfaction and survey for new product development.

Similarly, the vastly increased capability provided by the system's shared parallel processing can produce major improvements in complex simulations like modeling worldwide and local weather systems over time, as well as design and testing of any structure or product, from airliners and skyscrapers, to new drugs and to the use of much more sophisticated artificial intelligence (AI) in medical treatment and in sorting through and organizing the PC users voluminous input of electronic data from "push" technologies. Improvements in games also result, especially in terms of realistic simulation and realtime interactivity.

As is clear from the examples, the Internet or WWW network computer system like the MetaInternet can potentially put into the hands of the PC user an extraordinary new level of computer power vastly greater than the most powerful supercomputer existing today. The world's total of microchips is already about 350 billion, of which about 15 billion are microprocessors of some kind (most are fairly simple "appliance" type running wrist watches, televisions, cameras, cars, telephones, etc). Assuming growth at its current rates, in a decade the Internet/Internet II/WWW could easily have a billion individual PC users, each providing a average total of at least 10 highly sophisticated microprocessors (assuming PC's with at least 4 microprocessors (or more, such as 16 microprocessors or 32, for example) and associated other handheld, home entertainment, and business devices with microprocessors or digital processing capability, like a digital signal processor or successor devices). That results in a global computer a decade from now made of at least 10 billion microprocessors, interconnected by electromagnetic wave means at speeds approaching the speed of light.

In addition, if as is preferred the exceptionally numerous special purpose "appliance" microprocessors noted above, especially those that operate now intermittently like personal computers, are designed as is preferred to the same basic consensus industry standard as parallel microprocessors for PC's (or equivalents or successors) or for PC "systems on a chip" discussed later in FIGS. 10A-H (so that all PCs function homogeneously or are homogeneous in the parallel processing Internet, as preferred), and if such PCs are also connected by any broad bandwidth means including fiber optic cable or equivalent wireless, then the number of parallel processors potentially available can increase roughly about 10 times, for a net potential "standard" computing performance of up to 10,000 times current performance within fifteen years, exclusive of Moore's Law routine increases. Moreover, in a environment where all current intermittently operating microprocessors followed the same basic design standards as preferred so that all were homogeneous parallel processors, then although the cost per microprocessor increases somewhat, especially initially, the net cost of computing for all users falls drastically due to the general performance increase due to the use of otherwise idle "appliance" microprocessors. Therefore, the overall system cost reduction compels a transformation of virtually all such microprocessors, which are currently specialty devices known as application-specific integrated circuits (ASICs), into general microprocessors (like PC's), with software and firmware providing most of their distinguishing functionality. As noted above, homogeneity of parallel (and multi-tasking) processing design standards for microprocessors and network, including local and Internet, is preferred, but heterogeneity is also a well established parallel processing alternative providing significant benefits compared to non-parallel processing.

To put this in context, a typical supercomputer today utilizing the latest PC microprocessors has less than a hundred. Using network linkage to all external parallel processing, a peak maximum of perhaps 1 billion microprocessors can be made available for a network supercomputer user, providing it with the power 10,000,000 times greater than is available using current conventional internal parallel processing supercomputers (assuming the same microprocessor technology). Because of it's virtually limitless scalability mentioned above, resources made available by the network to the supercomputer user or PC user can be capable of varying significantly during any computing function, so that peak computing loads can be met with effectively whatever level of resources are necessary.

In summary, regarding monitoring the net provision of power between PC and network, FIGS. 1-9 show embodiments of a system for a network of computers, including personal computers, comprising: means for network services including browsing functions, as well as shared computer processing such as parallel processing, to be provided to the personal computers within the network; at least two personal computers; means for at least one of the personal computers, when idled by a personal user, to be made available temporarily to provide the shared computer processing services to the network; and means for monitoring on a net basis the provision of the services to each the personal computer or to the personal computer user. In addition, FIGS. 1-9 show embodiments including where the system is scalar in that the system imposes no limit to the number of the personal computers, including at least 1024 personal computers; the system is scalar in that the system imposes no limit to the number of personal computers participating in a single shared computer processing operation, including at least 256 personal computers; the network is connected to the Internet and its equivalents and successors, so that the personal computers include at least a million personal computers; the network is connected to the World Wide Web and its successors; the network includes at least one network server that participates in the shared computer processing; the monitoring means includes a meter device to measure the flow of computing power between the personal computers and the network; the monitoring means includes a means by which the personal user of the personal computer is provided with a prospective estimate of cost for the network to execute an operation requested by the personal user prior to execution of the operation by the network; the system has a control means by which to permit and to deny access to the personal computers by the network for shared computer processing; access to the personal computers by the network is limited to those times when the personal computers are idle; and the personal computers having at least one microprocessor and communicating with the network through a connection means having a speed of data transmission that is at least greater than a peak data processing speed of the microprocessor.

Also, relative to maintaining a standard cost, FIGS. 1-9 show embodiments of a system for a network of computers, including personal computers, comprising: means for network services including browsing functions, as well as shared computer processing such as parallel processing, to be provided to the personal computers within the network; at least two personal computers; means for at least one of the personal computers, when idled by a personal user, to be made available temporarily to provide the shared computer processing services to the network; and means for maintaining a standard cost basis for the provision of the services to each personal computer or to the personal computer user. In addition, FIGS. 1-9 show embodiments including where the system is scalar in that the system imposes no limit to the number of personal computers, including at least 1,024 personal computers; the system is scalar in that the system imposes no limit to the number of the personal computers participating in a single shared computer processing operation, including at least 256 personal computers; the network is connected to the Internet and its equivalents and successors, so that the personal computers include at least a million personal computers; the standard cost is fixed; the fixed standard cost is zero; the means for maintaining a standard cost basis includes the use of making available a standard number of personal computers for shared processing by personal computers; the network is connected to the World Wide Web and its successors; the personal user can override the means for maintaining a standard cost basis so that the personal user can obtain additional network services; the system has a control means by which to permit and to deny access to the personal computers by the network for shared computer processing; the personal computers having at least one microprocessor and communicating with the network through a connection means having a speed of data transmission that is at least greater than a peak data processing speed of the microprocessor.

Browsing functions generally include functions like those standard functions provided by current Internet browsers, such as Microsoft Explorer 3.0 or 4.0 and Netscape Navigator 3.0 or 4.0, including at least access to searching World Wide Web or Internet sites, exchanging E-Mail worldwide, and worldwide conferencing; an intranet network uses the same browser software, but might not include access to the Internet or WWW. Shared processing includes parallel processing and multitasking processing involving more than two personal computers, as defined above. The network system is entirely scalar, with any number of PC microprocessors potentially possible.

As shown in FIGS. 10A-10F, to deal with operational and security issues, it may be beneficial for individual users to have one microprocessor or equivalent device that is designated, permanently or temporarily, to be a master 30 controlling device (comprised of hardware and/or software and/of firmware and/or other component) that remains unaccessible (preferably using a hardware and/or software and/or firmware and/or other component firewall 50) directly by the network but which controls the functions of the other, slave microprocessors 40 when the network is not utilizing them.

Figure 10A:
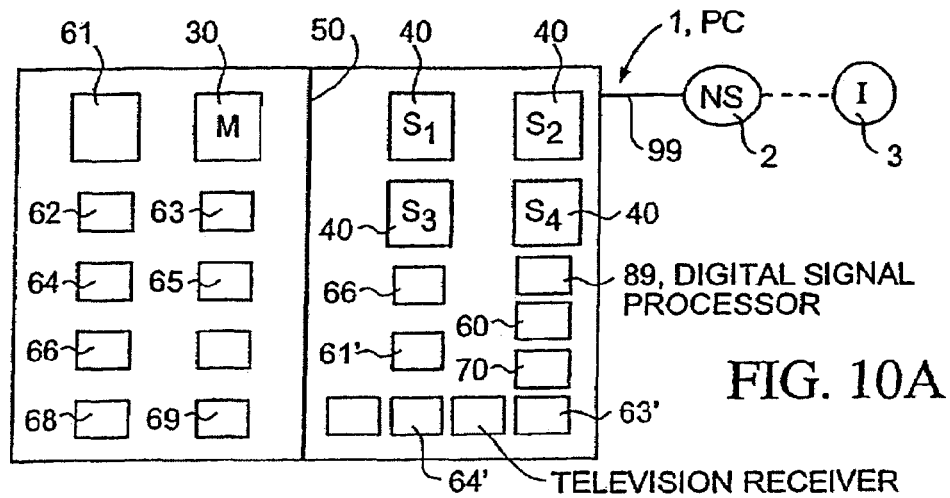
FIGS. 10A-10I are simplified diagrams of a section of a computer network, such as the Internet, showing an embodiment of a system architecture utilizing a firewall to separate that part of a networked PC (including a system reduced in size to a microchip) that is accessible to the network for shared processing from a part that is kept accessible only to the PC user; also showing the alternating role that preferably each PC in the network plays as either a master or slave in a shared processing operation involving one or more slave PC's in the network; and showing a home or business network system, which can be configured as an Intranet; in addition, showing PC and PC microchips controlled by a controller (including remote) with limited or no processing capability; and showing PC and PC microchips in which a firewall 50 is can be reconfigured by a PC user.

For example, as shown in FIGS. 10A, a typical PC 1 might have four or five microprocessors (even on a single microprocessor chip), with one master 30 and three or four slaves 40, depending on whether the master 30 is a controller exclusively (through different design of any component part), requiring four slave microprocessors 40 preferably; or the master microprocessor 30 has the same or equivalent microprocessing capability as a slave 40 and multiprocesses in parallel with the slave microprocessors 40, thereby requiring only three slave microprocessors 40, preferably. The number of PC slave microprocessors 40 can be increased to virtually any other number, such as at least about eight, about 16, about 32, about 64, about 128, about 256, about 512, about 1024, and so on (these multiples are preferred as conventional in the art, but not clearly required; the PC master microprocessors 30 can also be increased. Also included is the preferred firewall 50 between master 30 and slave 40 microprocessors. As shown in preceding FIGS. 1-9, the PC 1 in FIG. 10A is preferably connected to a network computer 2 and to the Internet or WWW or present or future equivalent or successor 3, like the MetaInternet.

Other typical PC hardware components such as hard drive 61, floppy diskette 62, compact disk-read only memory (CD-ROM) 63, digital video disk (DVD) 64, Flash memory 65, random access memory (RAM) 66, video or other display 67, graphics card 68, and sound card 69, as well as digital signal processor or processors, together with the software and/or firmware stored on or for them, can be located on either side of the preferred firewall 50, but such devices as the display 67, graphics card 68 and sound card 69 and those devices that both read and write and have non-volatile memory (retain data without power and generally have to written over to erase), such as hard drive 62, Flash memory 65, floppy drive 62, read/write CD-ROM 63 or DVD 64 are preferred to be located on the PC user side of the firewall 50, where the master microprocessor is also located, as shown in FIG. 10A, for security reasons primarily; their location can be flexible, with that capability controlled such as by password-authorized access.

Alternately, any or these devices that are duplicative (or for other exceptional needs) like a second hard drive 61' can be located on the network side of the firewall 50. RAM 66 or equivalent or successor memory, which typically is volatile (data is lost when power is interrupted), should generally be located on the network side of the firewall 50, however some can be located with the master microprocessor to facilitate its independent use.

However, read-only memory (ROM) devices including most current CD drives (CD-ROM's) 63' or DVD's (DVD- ROM) 64' or can be safely located on the network side of the firewall 50, since the data on those drives cannot be altered by network users; preemptive control of use preferably remains with the PC user.

However, at least a portion of RAM is can be kept on the Master 30 microprocessor side of the firewall 50, so that the PC user can use retain the ability to use a core of user PC 1 processing capability entirely separate from any network processing. If this capability is not desired, then the master 30 microprocessor can be moved to the network side of the firewall 50 and replaced with a simpler controller on the PC 1 user side, like the master remote controller 31 discussed below and shown in FIG. 10I.

And the master microprocessor 30 might also control the use of several or all other processors 60 owned or leased by the PC user, such as home entertainment digital signal processors 70, especially if the design standards of such microprocessors in the future conforms to the requirements of network parallel processing as described above. In this general approach, the PC master processor uses the slave microprocessors or, if idle (or working on low priority, deferable processing), make them available to the network provider or others to use. Preferably, wireless connections 100 are expected to be extensively used in home or business network systems, including use of a master remote controller 31 without (or with) microprocessing capability, with preferably broad bandwidth connections such as fiber optic cable connecting directly to at least one component such as a PC 1, shown in a slave configuration, of the home or business personal network system; that preferred connection links the home system to the network 2 such as the Internet 3, as shown in FIG. 10I. A business system includes preferably fiber optic links to most or all personal computers PC 1 and other devices with microprocessors, such as printers, copiers, scanners, fax machines, telephone and video conferencing equipment; wireless links can be used also.

A PC 1 user can remotely access his networked PC 1 by using another networked master microprocessor 30 on another PC 1 and using a password or other access control means for entry to his own PC 1 master microprocessor 30 and files, as is common now in Internet and other access. Alternately, a remote user can simply carry his own files and his own master microprocessor or use another networked master microprocessor temporarily has his own.

Figure 10B:
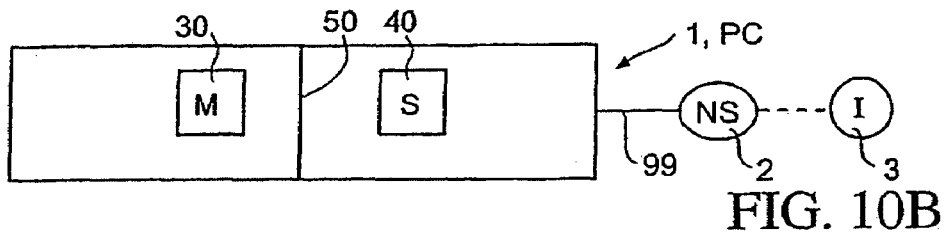

In the simplest configuration, as shown in FIG. 10B, the PC 1 has a single master microprocessor 30 and a single slave microprocessor 40, preferably separated by a firewall 50, with both processors used in parallel or multitasking processing or with only the slave 40 so used, and preferably connected to a network computer 2 and Internet 3 (and successors like the MetaInternet). Virtually any number of slave microprocessors 40 is possible. The other non-microprocessor components shown in FIG. 10A above might also be included in this simple FIG. 10B configuration.

Figure 10C:
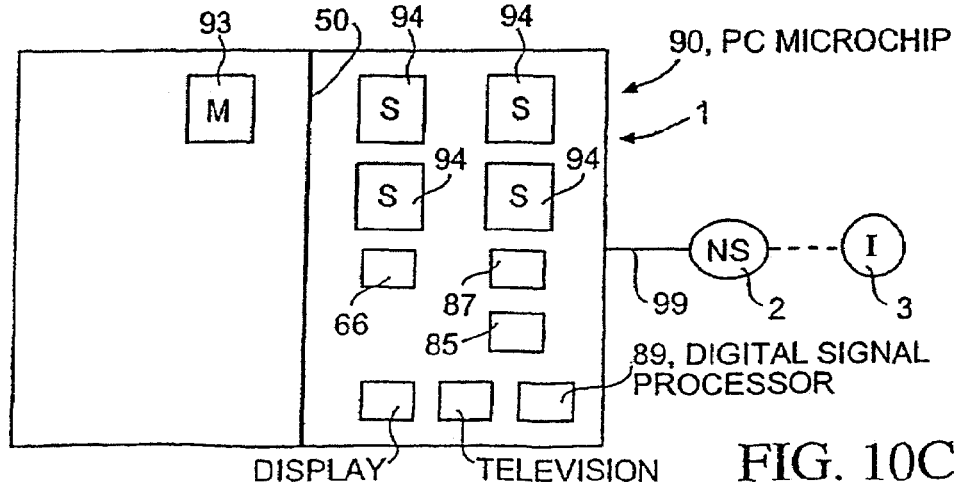

Preferably, as shown in FIG. 10C, microprocessors 90 are expected to integrate most or all of the other necessary computer components (or their present or future equivalents or successors), like a PC's memory (RAM 66, graphics 82, sound 83, power management 84, network communications 85, and video processing 86, possibly including modem 87, flash bios 88, digital signal processor or processors 89, and other components or present or future equivalents or successors) and internal bus, on a single chip 90 (silicon, plastic, or other), known in the industry as "system on a chip". Such a PC micro chip 90 preferably has the same architecture as that of the PC 1 shown above in FIG. 10A: namely, a master control and/or processing unit 93 and one or more slave processing units 94 (for parallel or multitasking processing by either the PC 1 or the Network 2), preferably separated by a firewall 50 and preferably connected to a network computer 3 and the Internet 3 and successors like the MetaInternet.

Existing PC components with mechanical components like hard drive 61, floppy or other removable diskette 62, CD-ROM 63 and DVD 64, which are mass storage devices with mechanical features that will likely not become an integral part of a PC "system of a chip" would preferably, of course, still be capable of connection to a single PC micro chip 90 and control by a single PC master unit 93.

Figure 10D:
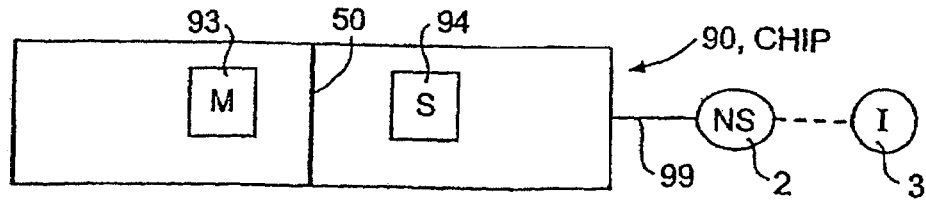

In the simplest multi-processor case, as shown in FIG. 10D, the chip 90 has a single master unit 93 and at least one slave unit 94 (with the master having a controlling function only or a processing function also), preferably separated by a firewall 50 and preferably connected to a network computer 3 and the Internet 3 (and successors like the MetaInternet). The other non-microprocessor components shown in FIG. 10A above might also be included in this simple FIG. 10D configuration.

Figure 10E:
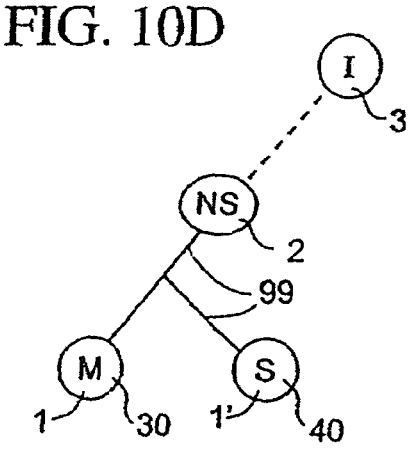
Figure 10F:
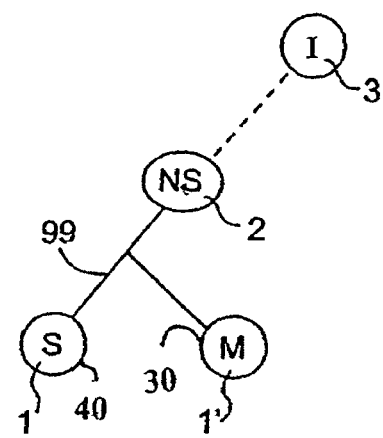

As noted in the second paragraph of the introduction to the background of the invention, in the preferred network invention, any computer can potentially be both a user and provider, alternatively—a dual mode operating capability. Consequently, any PC 1 within the network 2, preferably connected to the Internet 3 (and successors like the MetaInternet), can be temporarily a master PC 30 at one time initiating a parallel or multitasking processing request to the network 2 for execution by at least one slave PC 40, as shown in FIG. 10E. At another time the same PC 1 can become a slave PC 40 that executes a parallel or multitasking processing request by another PC 1' that has temporarily assumed the function of master 30, as shown in FIG. 10F. The simplest approach to achieving this alternation is for both master and slave versions of the parallel processing software to be loaded in each or every PC 1 that is to share in the parallel processing, so each PC 1 has the necessary software means, together with minor operational modifications, such as adding a switching means by which a signaled request for parallel processing initiated by one PC 1 user using master software is transmitted to at least a second PC 1, triggering its slave software to respond by initiating parallel processing.

Figure 10G:
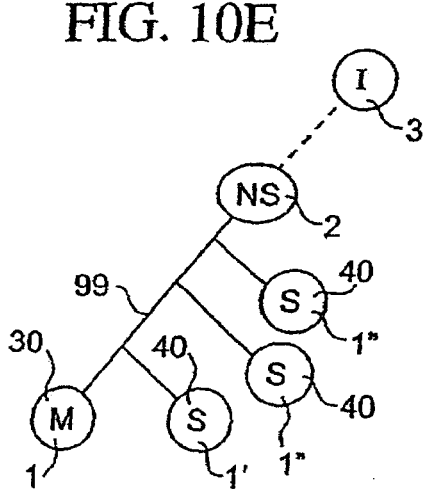
Figure 10H:
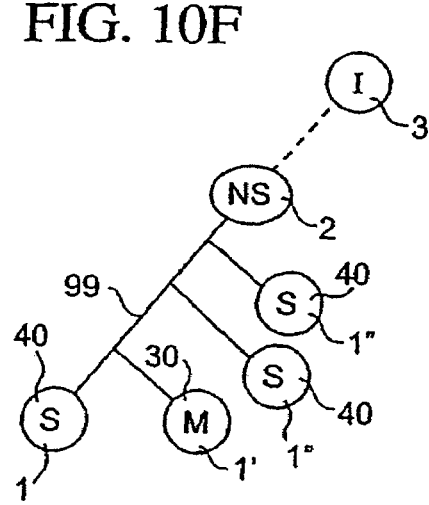
Figure 10I:
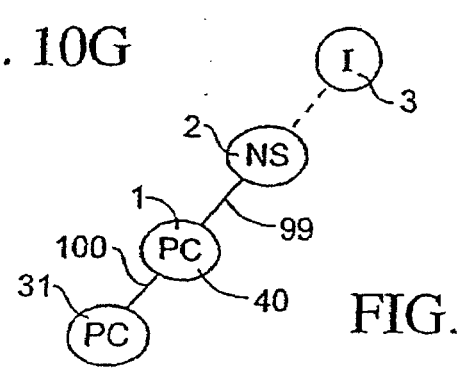

As shown in FIGS. 10G and 10H, which are parallel to FIGS. 10E and 10F, the number of PC slave processors 40 can be increased to any virtually other number, such as at least about 4; as shown, the processing system is completely scalar, so that further increases can occur to about eight, about 16, about 32, about 64, about 128, about 256, about 512, about 1024, and so on (these multiples indicated are preferred as conventional in the art, but not mandatory); the PC master microprocessors 30 can also be increased.

Figure 10J:
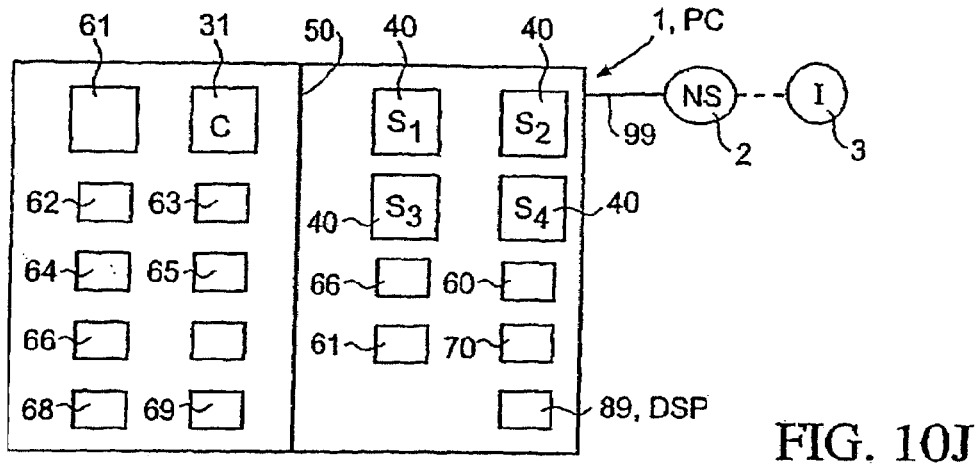
Figure 10K:
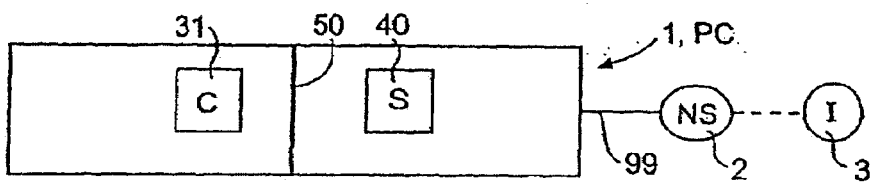
Figure 10L:
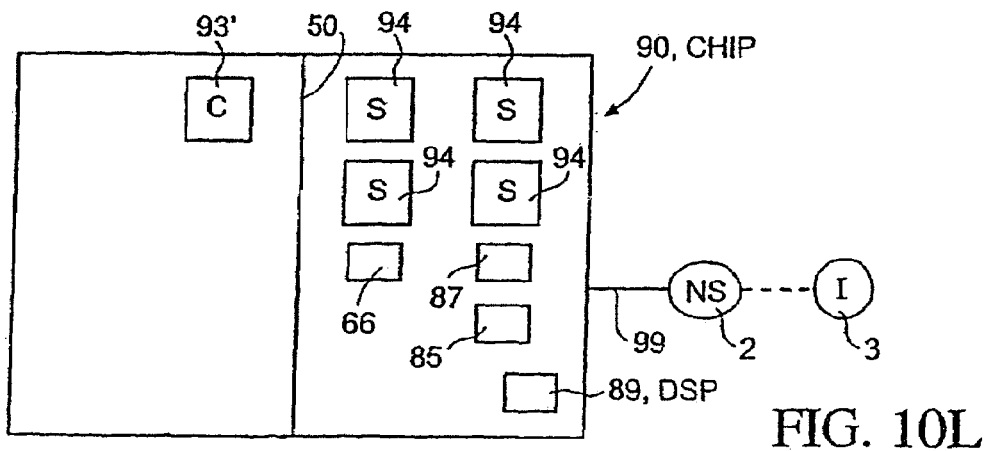
Figure 10M:
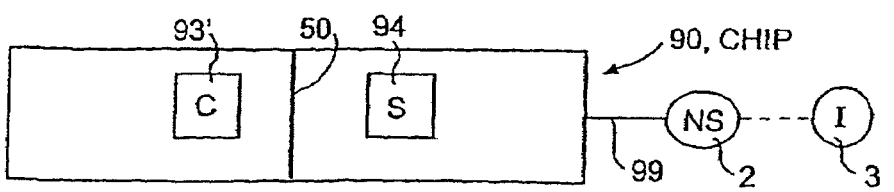

In summary, as noted above relative to FIG. 10I, a PC 1 can function as a slave PC 40 and be controlled by a master controller 31, which can be remote and which preferably can have limited or no microprocessing capability, but can as well have similar or greater capability. As shown in FIGS. 10J and 10K, such a master controller 31 is located on the PC user side of the firewall 50, under the control of the PC user, while the microprocessors 40 reside on the network side of the firewall 50. The master controller 31 preferably receives input from the PC user by local means such as keyboard, microphone, videocam or future hardware and/or software and/or firmware or other equivalent or successor interface means (as does a master processor 40) that provides input to a PC 1 or microprocessor 30 originating from a user's hand, voice, eye, nerve or nerves, or other body part; in addition, remote access by telephone, cable, wireless or other connection might also be enabled by a hardware and/or software and/or firmware and/or other means with suitable security such as password controlled access. Similarly, as shown in FIGS. 10L and 10M, relative to a PC "system on a chip" a master controller unit 93' (which could be capable of being accessed by the PC user through a remote controller 31) with only a controlling capability is be located on the PC user side of the firewall 50, under the control of the PC user, while the slave processor units 94 would reside on the network side of the firewall 50.

Figure 10N:
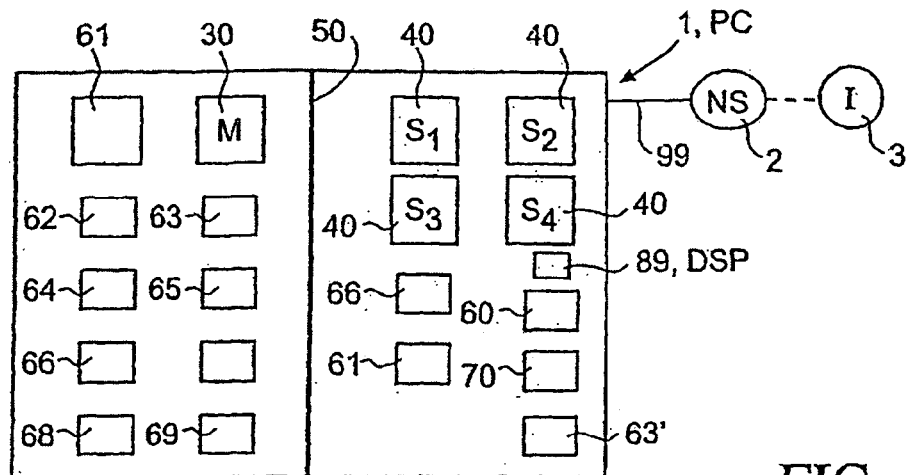
Figure 10O:
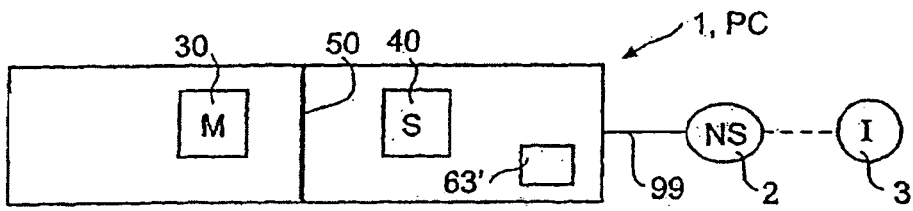

FIGS. 10N and 10O show PC 1 with a firewall 50 that is configurable through either hardware and/or software and/or firmware and/or other means; software configuration are easiest and most typical, but active motherboard hardware configuration is possible and may present some security advantages, including as use of manual or electromechanical or other switches or locks. FIG. 10N shows a CD-ROM 63' that has been placed by a PC user on the network side of a firewall 50 from a previous position on the PC user side of a firewall 50, which was shown in FIG. 10A. Preferably, the settings of a firewall 50 can default to those that safely protect the PC 1 from uncontrolled access by network users, but with capability for the relatively sophisticated PC user to override such default settings and yet with proper safeguards to protect the unsophisticated user from inadvertently doing so; configuration of a firewall 50 might also be actively controlled by a network administrator in a local network like that of a business, where a PC user may not be owner or leaser of the PC being used, either by remote access on the network or with a remote controller 31.

Figure 10P:
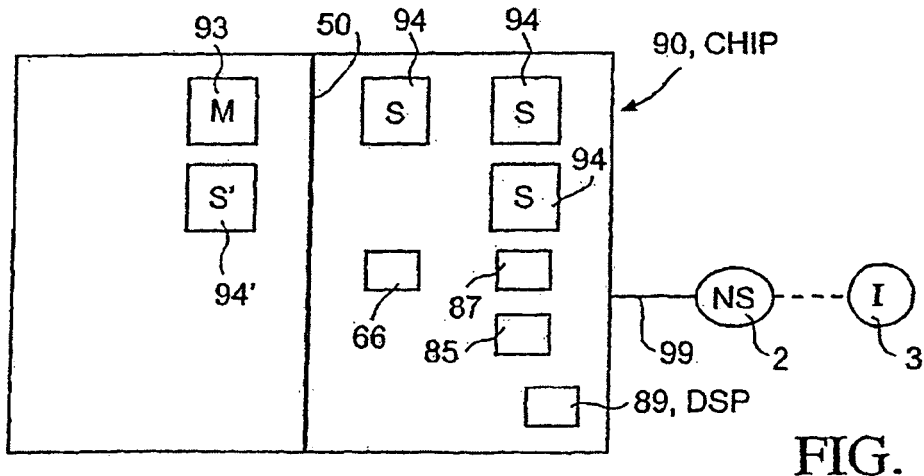
Figure 10Q:
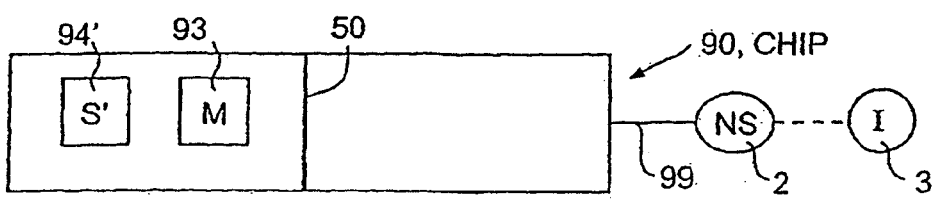

Similarly, FIGS. 10P and 10Q show a PC "system of a chip" 90 with a firewall 50 that is configurable through either hardware and/or software and/or firmware and/or other means; software configuration is easiest and most typical. Active configuration of the integrated circuits of the PC microchip 90 is also possible and may present some speed and security advantages. Such direct configuration of the circuits of the microchip 90 to establish or change in its firewall 50 could be provided by the use of field-programmable gate arrays (or FPGA's) or their future equivalents or successors; microcircuit electromechanical or other switches or locks can also be used potentially. In FIG. 10P, for example, slave processing unit 94' has been moved to the PC user side of a firewall 50 from a network side position shown in FIGS. 10C and 10L. Similarly, FIG. 10Q shows the same active configuration of chip circuit using FPGA's for the simplest form of multiprocessing microchip 90 with a single slave unit 94', transferring its position to the PC user's side of a firewall 50 from a network side shown in FIGS. 10M and 10D.

In summary, relative to the use of master/slave computers, FIGS. 10A-10I show embodiments of a system for a network of computers, including personal computers, comprising: at least two personal computers; means for at least one personal computer, when directed by its personal user, to function temporarily as a master personal computer to initiate and control the execution of a computer processing operation shared with at least one other personal computer in the network; means for at least one other personal computer, when idled by its personal user, to be made available to function temporarily as at least one slave personal computer to participate in the execution of a shared computer processing operation controlled by the master personal computer; and means for the personal computers to alternate as directed between functioning as a master and functioning as a slave in the shared computer processing operations. In addition, FIGS. 10A-10H show embodiments including wherein the system is scalar in that the system imposes no limit to the number of personal computers; for example, the system can include at least 256 said personal computers; the system is scalar in that the system imposes no limit to the number of personal computers participating in a single shared computer processing operation, including at least 256 said personal computers, for example; the network is connected to the Internet and its equivalents and successors, so that personal computers include at least a million personal computers, for example; the shared computer processing is parallel processing; the network is connected to the World Wide Web and its successors; a means for network services, including browsing and broadcast functions, as well as shared computer processing such as parallel processing, are provided to said personal computers within said network; the network includes at least one network server that participates in the shared computer processing; the personal computers include a transponder or equivalent or successor means so that a master personal computer can determine the closest available slave personal computers; the closest available slave personal computer is compatible with the master personal computer to execute said shared computer processing operation; the personal computers having at least one microprocessor and communicating with the network through a connection means having a speed of data transmission that is at least greater than a peak data processing speed of the microprocessor; and a local network PC 1 being controlled remotely by a microprocessor controller 31.

The preferred use of the firewall 50, as described above in FIGS. 10A-10I, provides a solution to an important security problem by preferably completely isolating host PC's 1 that are providing slave microprocessors to the network for parallel or other shared processing functions from any capability to access or retain information about any element about that shared processing. In addition, of course, the firewall 50 provides security for the host PC against intrusion by outside hackers; by reducing the need for encryption and authentication, the use of firewalls 50 can provide a relative increase in computing speed and efficiency. In addition to computers such as personal computers, the firewall 50 described above could be used in any computing device included in this application's above definition of personal computers, including those with "appliance"-type microprocessors, such as telephones, televisions or cars, as discussed above.

In summary, regarding the use of firewalls, FIGS. 10A-10I show embodiments of a system architecture for computers, including personal computers, to function within a network of computers, comprising: a computer with at least two microprocessors and having a connection means with a network of computers; the architecture for the computers including a firewall means for personal computers to limit access by the network to only a portion of the hardware, software, firmware, and other components of the personal computers; the firewall means will not permit access by the network to at least a one microprocessor having a means to function as a master microprocessor to initiate and control the execution of a computer processing operation shared with at least one other microprocessor having a means to function as a slave microprocessor; and the firewall means permitting access by the network to the slave microprocessor. In addition, the system architecture explicitly includes embodiments of, for example, the computer is a personal computer; the personal computer is a microchip; the computer have a control means by which to permit and to deny access to the computer by the network for shared computer processing; the system is scalar in that the system imposes no limit to the number of personal computers, including at least 256 said personal computers, for example; the network is connected to the Internet and its equivalents and successors, so that the personal computers include at least a million personal computers, for example; the system is scalar in that the system imposes no limit to the number of personal computers participating in a single shared computer processing operation, including at least 256 said personal computers, for example; the personal computers having at least one microprocessor and communicating with the network through a connection means having a speed of data transmission that is at least greater than a peak data processing speed of the microprocessor.

In summary, regarding the use of controllers with firewalls, FIGS. 10J-10M show embodiments of a system architecture for computers, including personal computers, to function within a network of computers, comprising for example: a computer with at least a controller and a microprocessor and having a connection means with a network of computers; the architecture for the computers including a firewall means for personal computers to limit access by the network to only a portion of the hardware, software, firmware, and other components of the personal computers; the firewall means will not permit access by the network to at least a one controller having a means to initiate and control the execution of a computer processing operation shared with at least one microprocessor having a means to function as a slave microprocessor; and the firewall means permitting access by the network to the slave microprocessor. In addition, the system architecture explicitly includes embodiments of, for example, the computer is a personal computer; the personal computer is a microchip; the computer have a control means by which to permit and to deny access to the computer by the network for shared computer processing; the system is scalar in that the system imposes no limit to the number of personal computers, including at least 256 said personal computers, for example; the network is connected to the Internet and its equivalents and successors, so that the personal computers include at least a million personal computers, for example; the system is scalar in that the system imposes no limit to the number of personal computers participating in a single shared computer processing operation, including at least 256 said personal computers, for example; the personal computers having at least one microprocessor and communicating with the network through a connection means having a speed of data transmission that is at least greater than a peak data processing speed of the microprocessor; and the controller being capable of remote use.

In summary, regarding the use of firewalls that can be actively configured, FIGS. 10N-10Q show embodiments of a system architecture for computers, including personal computers, to function within a network of computers, comprising for example: a computer with at least two microprocessors and having a connection means with a network of computers; the architecture for the computers including a firewall means for personal computers to limit access by the network to only a portion of the hardware, software, firmware, and other components of the personal computers; the firewall means will not permit access by the network to at least a one microprocessor having a means to function as a master microprocessor to initiate and control the execution of a computer processing operation shared with at least one other microprocessor having a means to function as a slave microprocessor; the firewall means permitting access by the network to the slave microprocessor; the configuration of the firewall being capable of change by a user or authorized local network administrator; the change in firewall configuration of a microchip PC is made at least in part using field-programmable gate arrays or equivalents or successors. In addition, the system architecture explicitly includes embodiments of, for example, the computer is a personal computer; the personal computer is a microchip; the computer have a control means by which to permit and to deny access to the computer by the network for shared computer processing; the system is scalar in that the system imposes no limit to the number of personal computers, including at least 256 said personal computers; the network is connected to the Internet and its equivalents and successors, so that the personal computers include at least a million personal computers; the system is scalar in that the system imposes no limit to the number of personal computers participating in a single shared computer processing operation, including at least 256 said personal computers; the personal computers having at least one microprocessor and communicating with the network through a connection means having a speed of data transmission that is preferably at least greater than a peak data processing speed of the microprocessor.

It is presently contemplated that PC 1 microprocessors noted above be designed to the same basic consensus industry standard as parallel microprocessors for PC's (or equivalents or successors) as in FIGS. 10A-10B or for PC "systems on a chip" discussed in FIGS. 10C-10D. Although the cost per microprocessor might rise somewhat initially, the net cost of computing for all users is expected to fall drastically almost instantly due to the significant general performance increase created by the new capability to use of heretofore idle "appliance" microprocessors. The high potential for very substantial benefit to all users should provide a powerful force to reach consensus on important industry hardware, software, and other standards on a continuing basis for such basic parallel network processing designs utilizing the Internet 3 and successor. It is preferred but not required that such basic industry standards be adopted at the outset of system design and for use of only the least number of shared microprocessors initially. If such basic industry standards are adopted at the outset and for the least number of shared microprocessors initially, and if design improvements incorporating greater complexity and more shared microprocessors are phased in gradually overtime on a step by step basis, then conversion to a MetaInternet architecture at all component levels should be relatively easy and inexpensive (whereas an attempt at sudden, massive conversion is hugely difficult and prohibitively expensive). The scalability of the MetaInternet system architecture (both vertically and horizontally) as described herein makes this sensible approach possible.

By 1998, manufacturing technology improvements allow 20 million transistors to fit on a single chip (with circuits as thin as 0.25 microns) and, in the next cycle, 50 million transistors using 0.18 micron circuits. Preferably, that entire computer on a chip is linked, preferably directly, by fiber optic or other broad bandwidth connection means to the network so that the limiting factor on data throughput in the network system, or any part, is only the speed of the linked microprocessors themselves, not the transmission speed of the linkage. Such direct fiber optic linkage will obviate the need for an increasingly unweldy number of microchip connection prongs, which is currently in the one to two hundred range in the Intel Pentium series and will reach over a thousand prongs in the 1998 IBM Power3 microprocessor. One or more digital signal processors 89 and one or more all optical switches 92 located on a microprocessor 90 (or 30 or 40), together with numerous channels and/or signal multiplexing (such as wave division) of the fiber optic signal can substitute for a vast multitude of microchip connection prongs.

For computers that are not reduced to a single chip, it is also preferred that the internal system bus or buses of any such PC's have a transmission speed that is at least high enough that the all processing operations of the PC microprocessor or microprocessors is unrestricted (and other PC components like RAM) and that the microprocessor chip or chips are directly linked by fiber optic or other broad bandwidth connection, as with the system chip described above, so that the limiting factor on data throughput in the network system, or any part, is only the speed of the linked microprocessors themselves, not the transmission speed of the linkage.

The individual user PC's can be connected to the Internet (via an Intranet)/Internet II/WWW or successor, like the MetaInternet (or other) network by any electromagnetic means, with the very high transmission speed provided by the broad bandwidth of fiber optic cable being preferred, but hybrid systems using fiber optic cable for trunk lines and coaxial cable to individual users may be more cost effective initially, but less preferred unless cable can be made (through hardware and/or software and/or firmware and/or other component means) to provide sufficiently broad bandwidth connections to provide unrestricted throughput by connected microprocessors. Given the speed and bandwidth of transmission of fiber optic or equivalent or successor connections, conventional network architecture and structures should be acceptable for good system performance, making possible a virtual complete interconnection network between users.

However, the best speed for any parallel processing operation should be obtained, all other things being equal, by utilizing the available microprocessors that are physically the closest together. Consequently, as shown previously in FIG. 8, the network needs have the means (through hardware and/or software and/or firmware and/or other component) to provide on a continually ongoing basis the capability for each PC to know the addresses of the nearest available PC's, perhaps sequentially, from closest to farthest, for the area or cell immediately proximate to that PC and then those cells of adjacent areas.

Figure 11:
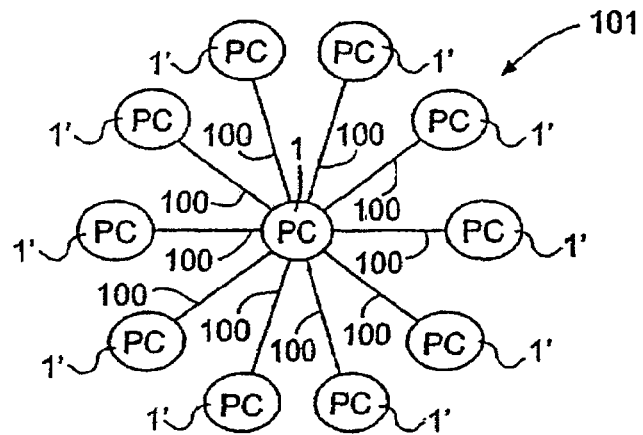
FIG. 11 is a simplified diagram of a section of a computer network, such as the Internet, showing an embodiment of a system architecture for connecting clusters of PC's to each other by wireless means, to create the closest possible (and therefore fastest) connections.

Network architecture that clusters PC's together should therefore be preferred, but not mandatory for substantial benefit, and can be constructed by wired means. However, as shown in FIG. 11, it would probably be very beneficial to construct local network clusters 101 (or cells) of personal computers 1' by wireless 100 means, since physical proximity of any PC 1 to its closest other PC 1' should be easier to access directly that way, as discussed further below. Besides, it is economically preferable for at least several network providers to serve any given geographic area to provide competitive service and prices.

It would be advantageous, then, for those wireless PC connections to be PC resident and capable of communicating by wireless or wired (or mixed) means with all available PC's in the cluster or cell geographic area, both proximal and potentially out to the practical limits of the wireless transmission.

Figure 12:
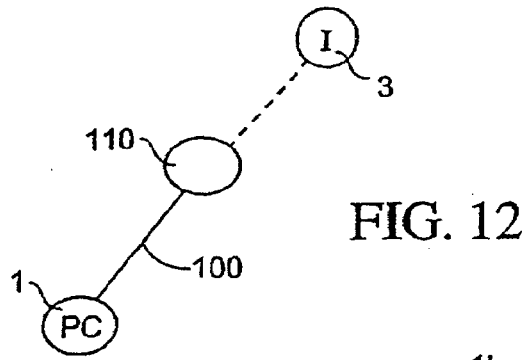
FIG. 12 is a simplified diagram of a section of a computer network, such as the Internet, showing an embodiment of a system architecture for connecting PC's to a satellite by wireless means.

As shown in FIG. 12, wireless PC connections 100 can be made to existing non-PC network components, such as one or more satellites 110, or present or future equivalent or successor components and the wireless transmissions can be conventional radio waves, such as infrared or microwave, or can utilize any other part of the electromagnetic wave spectrum.

Figure 13:
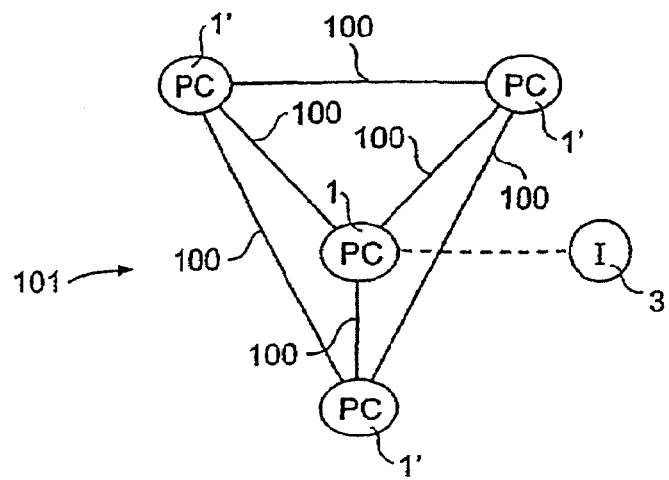
FIG. 13 is a simplified diagram of a section of a computer network, such as the Internet, showing an embodiment of a system architecture providing a cluster of networked PC's with complete interconnectivity by wireless means.

Moreover, as shown in FIG. 13, such a wireless or wired approach also make it easily possible in the future to develop network clusters 101 of available PC's 1' with complete interconnectivity; i.e., each available PC 1 in the cluster 101 is connected (preferably wirelessly 100) to every other available PC 1 in the cluster 101, constantly adjusting to individual PC's becoming available or unavailable. Given the speed of some wired broad bandwidth connections, like fiber optic cable, such clusters 101 with complete interconnectivity is certainly a possible embodiment.

Figure 14A:
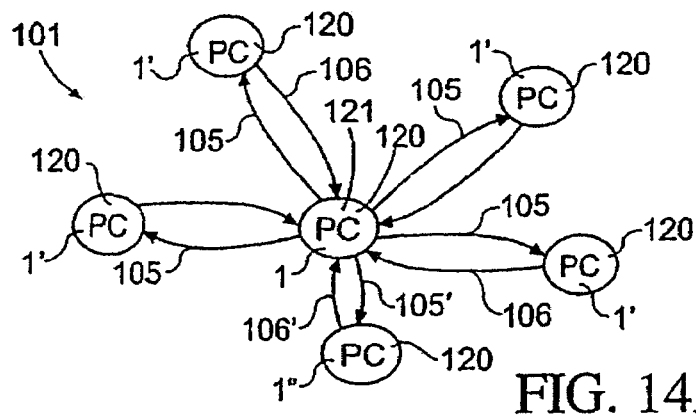
FIG. 14A is a simplified diagram of a section of a computer network, such as the Internet, showing an embodiment of a transponder means whereby a PC can identify one or more of the closest available PC's in a network cluster to designate for shared processing by wireless means.
Figure 14B:
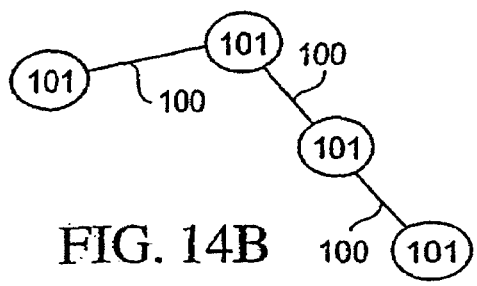
FIG. 14B shows clusters connected wirelessly.

As shown in FIGS. 14A-14D, it would be advantageous for such wireless systems to include a wireless device 120 comprised of hardware and/or software and/or firmware and/or other component, like the PC 1 availability device described above preferably resident in the PC, but also with a network-like capability of measuring the distance from each PC 1 in its cluster 101 by that PC's signal transmission by transponder or its functional equivalent and/or other means to the nearest other PC's 1' in the cluster 101. As shown in FIG. 14A, this distance measurement could be accomplished in a conventional manner between transponder devices 120 connected to each PC in the cluster 101; for example, by measuring in effect the time delay from wireless transmission by the transponder device 120 of an interrogating signal 105 to request initiation of shared processing by a master PC 1 to the reception of a wireless transmission response 106 signaling availability to function as a slave PC from each of the idle PC's 1' in the cluster 101 that has received the interrogation signal 105. The first response signal 106' received by the master PC 1 is from the closest available slave PC 1" (assuming the simplest shared processing case of one slave PC and one master PC), which is selected for the shared processing operation by the requesting master PC 1, since the closer the shared microprocessor, the faster the speed of the wireless connections 100 is between sharing PC's (assuming equivalence of the connection means and other components among each of the PC's 1'). The interrogation signal 105 might specify other selection criteria also, for example, for the closest compatible (initially perhaps defined by a functional requirement of the system to be an identical microprocessor) slave PC 1", with the first response signal 106' being selected as above.

This same transponder approach also can be used between PC's 1" connected by a wired 99 (or mixed wired/wireless) means, despite the fact that connection distances would generally be greater (since not line of sight, as is wireless), as shown in FIG. 14A, since the speed of transmission by the preferred broad bandwidth transmission means such as fiber optic cable is so high as to offset that greater distance. From a cost basis, this wired approach might be preferable for such PC's already connected by broad bandwidth transmission means, since additional wireless components like hardware and software are not necessary. In that case, a functionally equivalent transponder device 120 can be operated in wired clusters 101 in generally the same manner as described above for PC's connected in wireless clusters 101. Networks incorporating PC's 1 connected by both wireless and wired (or mixed) means are anticipated, like the home or business network mentioned in FIG. 10I, with mobile PC's or other computing devices preferably using wireless connections. Depending on distances between PC's and other factors, a local cluster 101 of a network 2 might connect wirelessly between PC's and with the network 2 through transponding means linked to wired broad bandwidth transmission means, as shown in FIG. 14C.

Figure 14D:
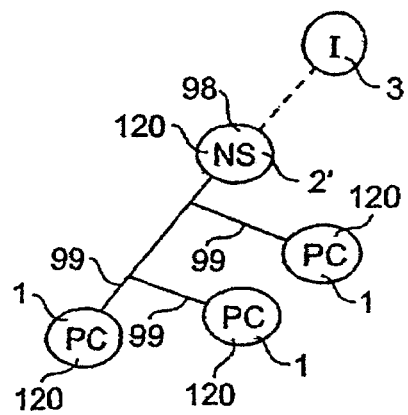
FIG. 14D shows a network client/server wired system with transponders.
Figure 14C:
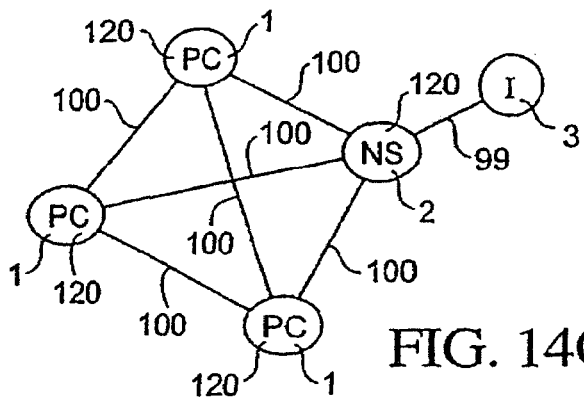
FIG. 14C shows a wireless cluster with transponders and with a network wired connection to Internet.

As shown in FIG. 14D, the same general transponder device means 120 can also be used in a wired 100 network system 2 employing network servers 98 operated, for example, by an ISP, or in any other network system architectures (including client/server or peer to peer) or any other topologies (including ring, bus, and star) either well known now in the art or their future equivalents or successors.

The FIG. 14 approach to establishing local PC clusters 101 for parallel or other shared processing has major advantage in that it avoids using network computers such as servers (and, if wireless, other network components including even connection means), so that the entire local system of PC's within a cluster 101 operates independently of network servers, routers, etc. Moreover, particularly if connected by wireless means, the size of the cluster 101 could be quite large, being limited generally by PC wireless transmission power, PC wireless reception sensitivity, and local and/or other conditions affecting transmission and reception. Additionally, one cluster 101 could communicate by wireless 100 means with an adjacent or other clusters 101, as shown in FIG. 14B, which could thereby include those beyond its own direct transmission range.

To improve response speed in shared processing involving a significant number of slave PC's 1, a virtual potential parallel processing network for PC's 1 in a cluster 101 preferably is established before a processing request begins. This is accomplished by the transponder device 120 in each idle PC 1, a potential slave, broadcasting by transponder 120 its available state when it becomes idle and/or periodically afterwards, so that each potential master PC 1 in the local cluster 101 is able to maintain relatively constantly its own directory 121 of the idle PC's 1 closest to it that are available to function as slaves. The directory 121 contains, for example, a list of about the standard use number of slave PC's 1 for the master PC (which initially probably is just one other PC 1'') or a higher number, preferably listed sequentially from the closest available PC to the farthest. The directory of available slave PC's 1 is preferably updated on a relatively up to date basis, either when a change occurs in the idle state of a potential slave PC in the directory 121 or periodically.

Such ad hoc clusters 101 should be more effective by being less arbitrary geographically, since each individual PC is effectively in the center of its own ad hoc cluster. Scaling up or down the number of microprocessors required by each PC at any given time is also more seamless.

The complete interconnection potentially provided optimally by such ad hoc wireless clusters is also remarkable because such clusters mimics the neural network structure of the animal brain, wherein each nerve cell, called a neuron, interconnects in a very complicated way with the neurons around it. By way of comparison, the global network computer described above that is expected in a decade can have at least about 10 times as many PC's as a human brain has neurons and they can be connected by electromagnetic waves traveling at close to the speed of light, which is about 300,000 times faster than the transmission speed of human neurons (which, however, are much closer together).

An added note: as individual PC's continue becoming much more sophisticated and more network oriented, compatibility issues may decrease in importance, since all major types of PC's will be able to emulate each other and most software, particularly relative to parallel processing, may no longer be hardware specific. However, to achieve maximum speed and efficiency, it is beneficial to set compatible hardware, software, firmware, and other component standards to realize potential performance advantages attainable with homogeneous parallel processing components of the global network computer.

Until that compatibility or homogeneity is designed into the essential components of network system, the existing incompatibility or heterogeneity of current components increase the difficulty involved in parallel processing across large networks. Even so, the use of message passing interfaces, for example, has made massively parallel processing between heterogeneous personal computers fairly easy for uncoupled operations, as shown for example in the Beowulf system. Programming languages like Java is one approach that will provide a partial means for dealing with the heterogeneity problem, whereas Linux provides greater speed and efficiency. In addition, using similar configurations of existing standards, like using PC's available on the Internet (with its vast resources) with a specific Intel Pentium chip with other identical or nearly identical PC components is probably the best way in the current technology to eliminate many of the serious existing problems that can easily be designed around using available technologies by adopting reasonable consensus standards for specification of all system components. The potential gains to all parties with an interest far outweigh the potential costs.

The above described global network computer system has an added benefit of reducing the serious and growing problem of the nearly immediate obsolescence of computer hardware, software, firmware, and other components. Since the preferred system above is the sum of its constituent parts used in parallel processing, each specific PC component becomes less critical. As long as access to the network utilizing sufficient bandwidth is possible, then all other technical inadequacies of the user's own PC can be completely compensated for by the network's access to a multitude of technically able PC's of which the user will have temporary use.

Although the global network computer will clearly cross the geographical boundaries of nations, its operation is not likely to be unduly bounded by inconsistent or arbitrary laws within those individual states. There will be considerable pressure on all nations to conform to reasonable system architecture and operational standards generally agreed upon, since the penalty of not participating in the global network computer is potentially so high as to not be politically possible anywhere.

Figure 15:
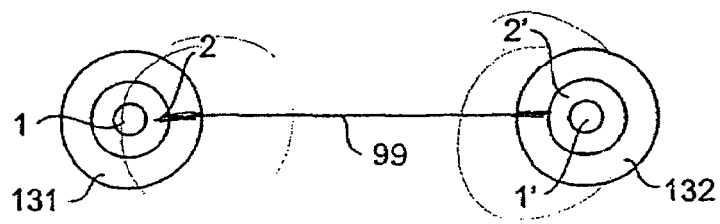
FIG. 15 is a simplified diagram of a section of a computer network, such as the Internet, showing an embodiment of a routing means whereby a PC request for shared processing is routed within a network using preferably broad bandwidth connection means to another area in a network with one or more idle PC's available.

As shown in FIG. 15, because the largest number of user PC's are completely idle, or nearly so, during the night, it can be useful for the most complicated large scale parallel processing, involving the largest numbers of processors with uninterrupted availability as close together as possible, to be routed by the network to geographic areas of the globe undergoing night and to keep them there even as the Earth rotates by shifting computing resources as the world turns. As shown in the simplest case in FIG. 15, during the day, at least one parallel processing request by at least one PC 1 in a network 2 in the Earth's western hemisphere 131 are transmitted by very broad bandwidth connection wired 99 means such as fiber optic cable to the Earth's eastern hemisphere 132 for execution by at least one PC 1' of a network 2', which is idle during the night and the results are transmitted back by the same means to network 2 and the requesting at least one PC 1.

Any number of individual PC's within local networks like that operated by an ISP can be grouped into clusters or cells, as is typical in the practice of the network industry. As is common in operating electrical power grids and telecommunications and computer networks, many such processing requests from many PC's and many networks could be so routed for remote processing, with the complexity of the system growing substantially over time in a natural progression.

Alternatively, for greater security or simplicity, nighttime parallel processing can remain within a relatively local area and emphasize relatively massively parallel processing by larger entities such as business, government, or universities for relatively complicated applications that benefit from comparatively long nightly periods of largely uninterrupted use of significant numbers of slave personal computers PC 1.

Figure 16A:
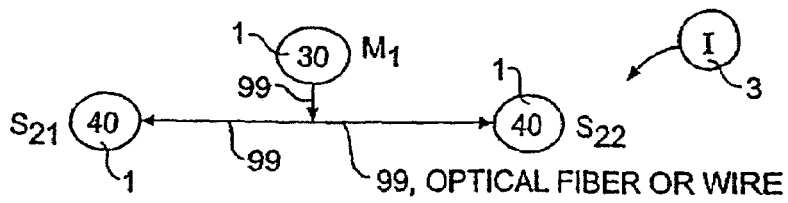
FIGS. 16A-16Z and 16AA show a new hierarchical network architecture for personal computers and/or microprocessors based on subdivision of parallel processing or multi-tasking operations through a number of levels down to a processing level.
Figure 16B:
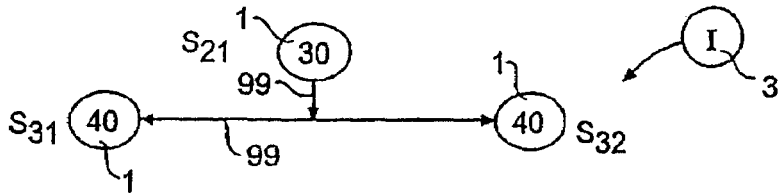
Figure 16C:
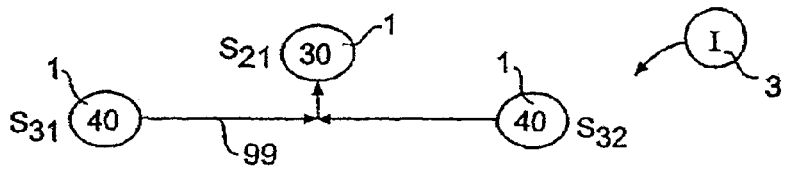
Figure 16D:
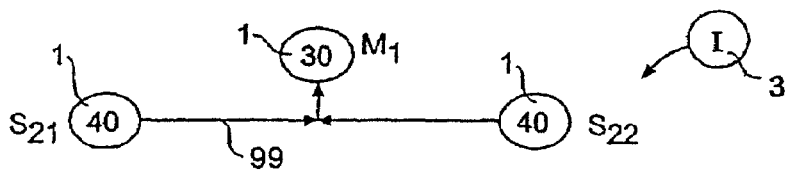
Figure 16E:
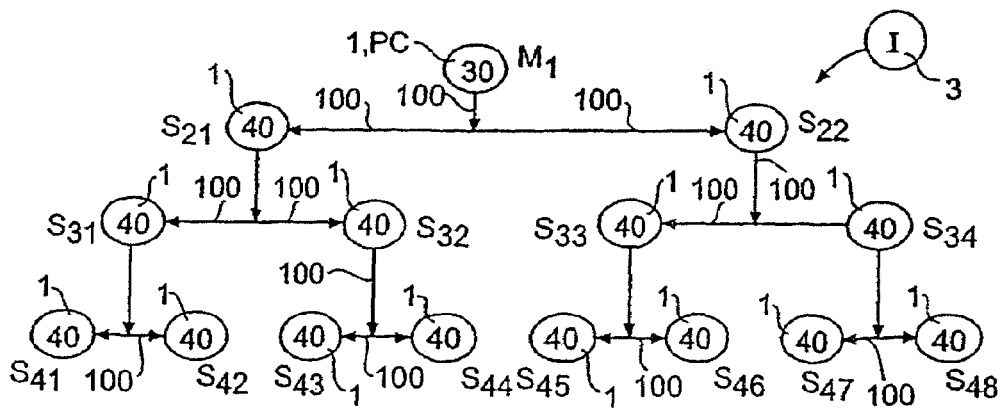
Figure 16F:
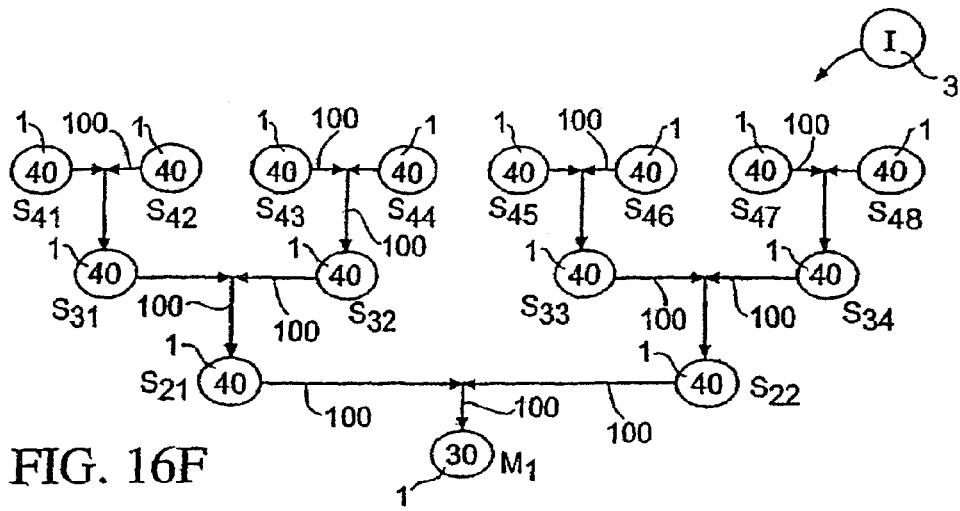
Figure 16G:
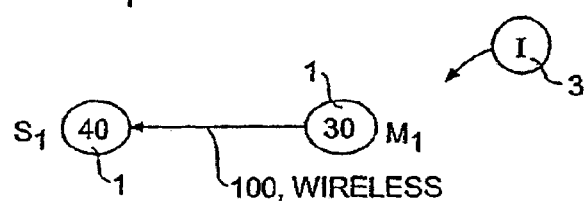
Figure 16H:
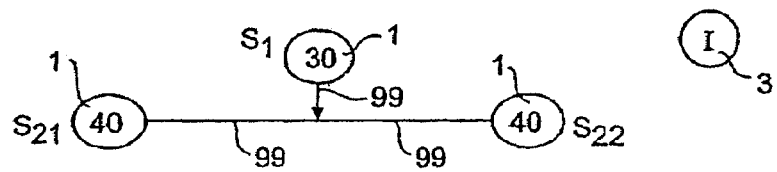
Figure 16I:
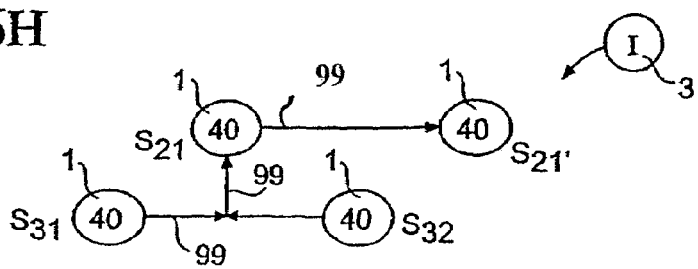
Figure 16J:
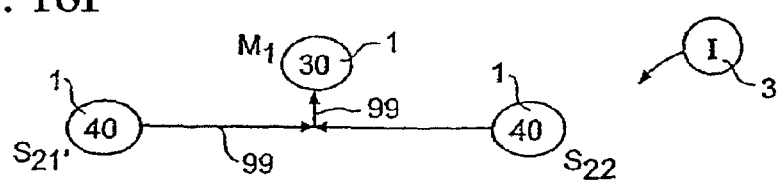
Figure 16K:
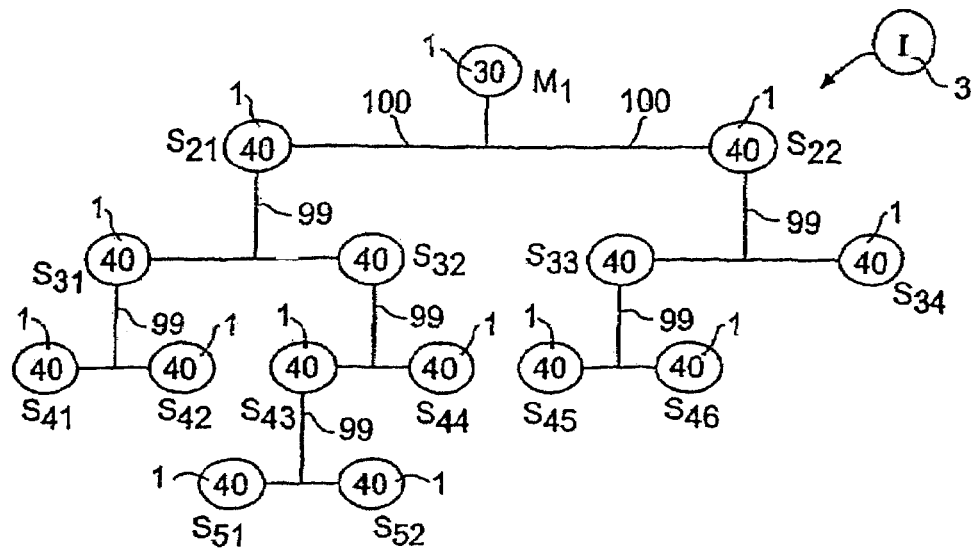
Figure 16L:
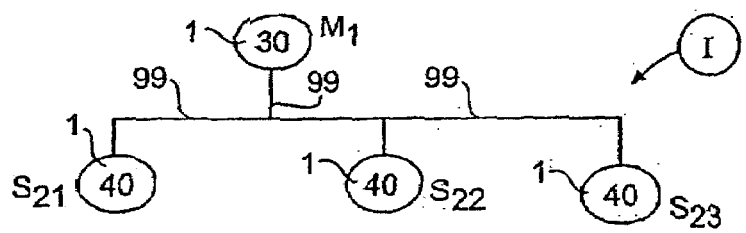
Figure 16M:
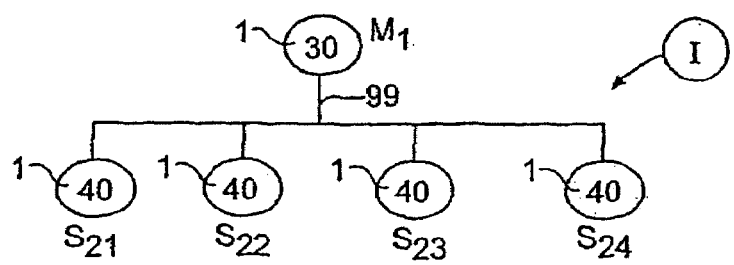
Figure 16N:
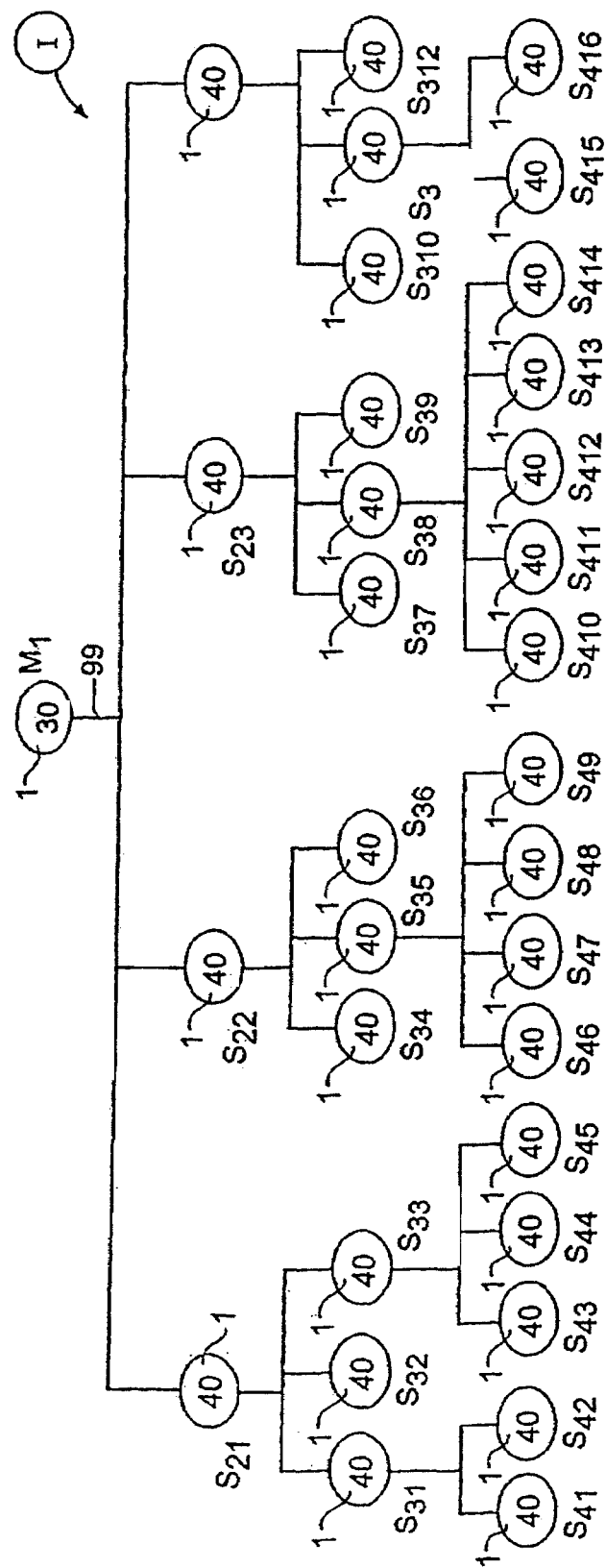
Figure 16O:
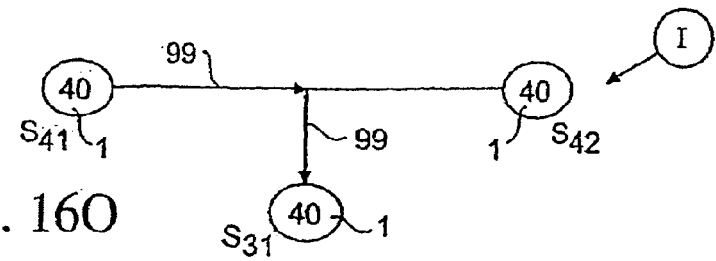
Figure 16P:
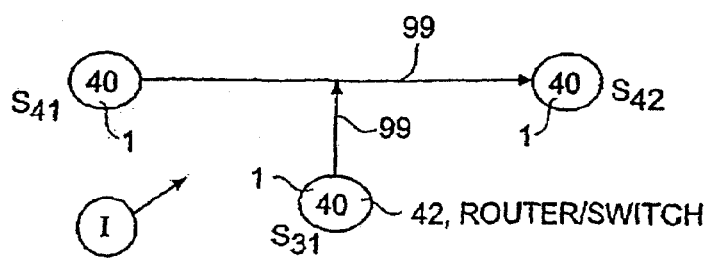
Figure 16Q:
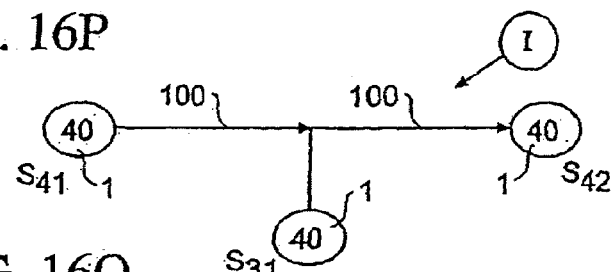
Figure 16R:
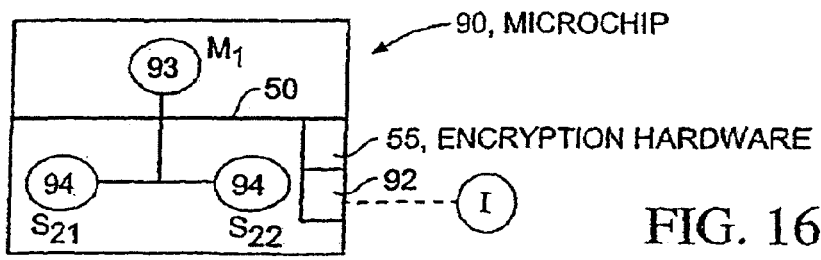
Figure 16S:
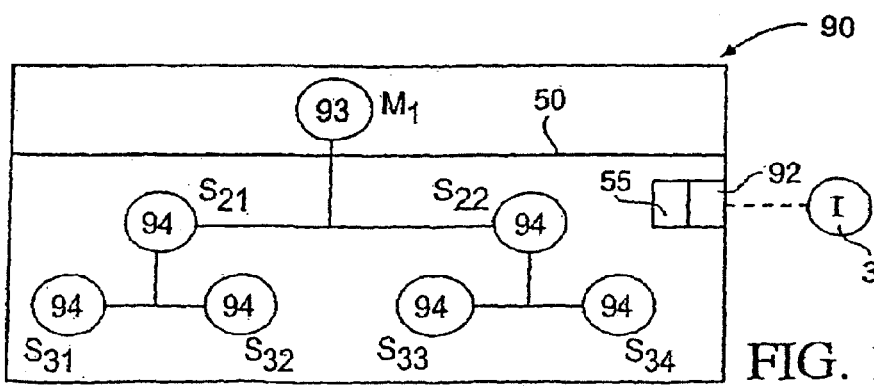
Figure 16T:
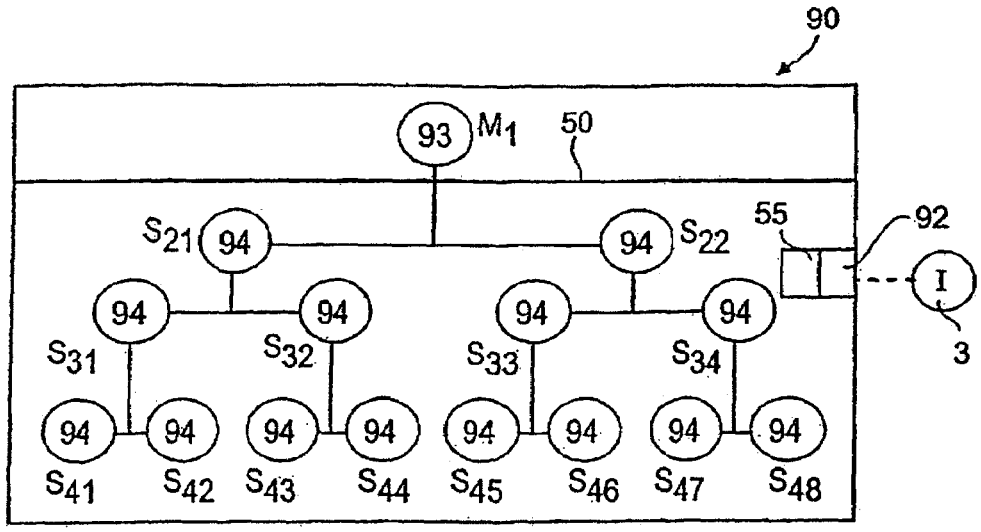
Figure 16U:
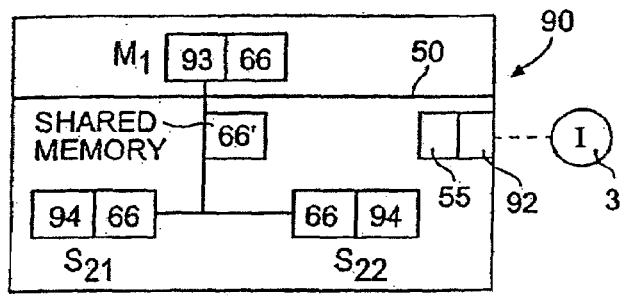
Figure 16V:
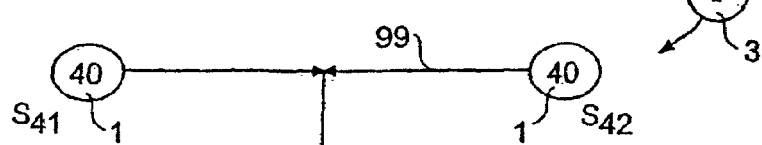
Figure 16W:
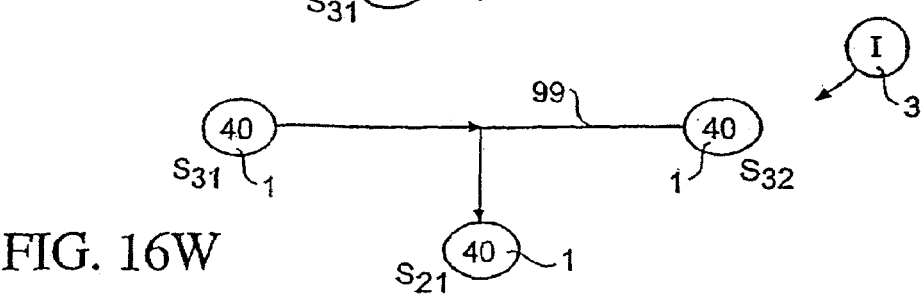
Figure 16X:
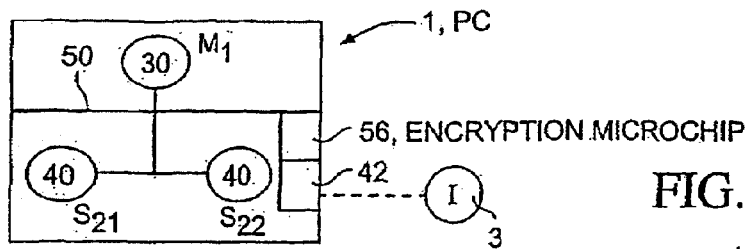
Figure 16Y:
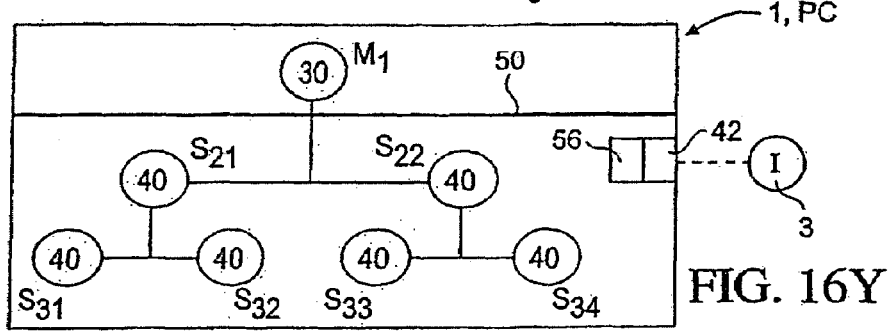
Figure 16Z:
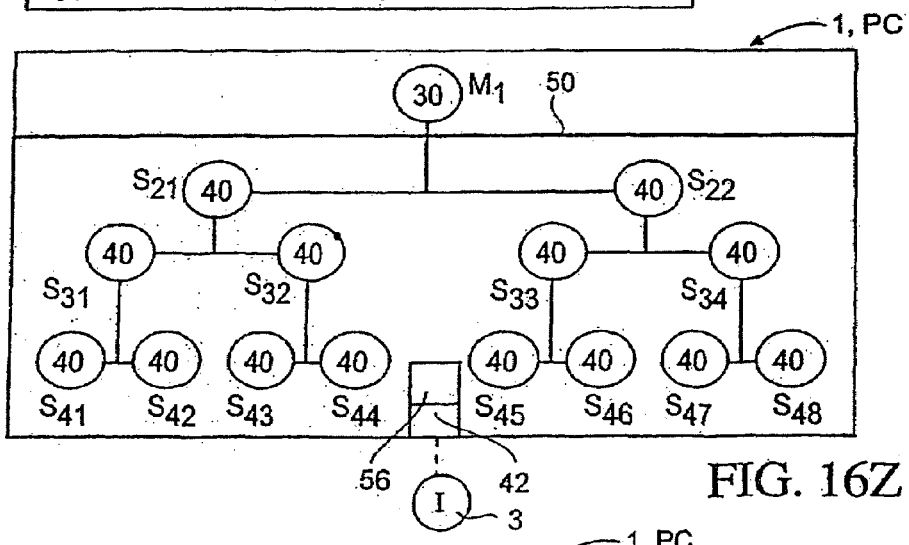
Figure 16A:
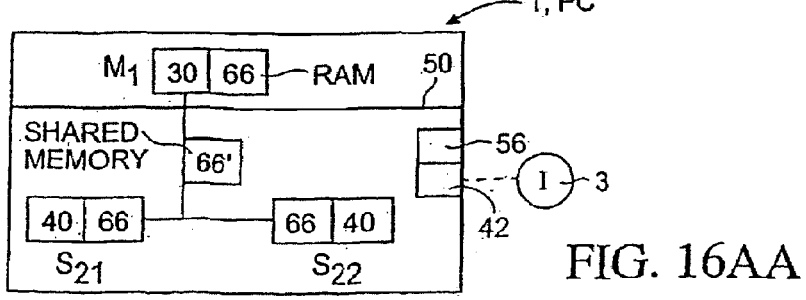
Figure 16A:
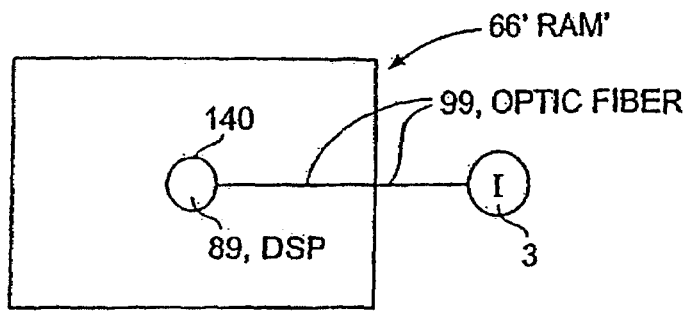

While the conventional approach to configuring a network of personal computers PC 1 for parallel processing is simply to string them together in a simple bus-type architecture, as shown previously in FIG. 9, new FIGS. 16A-16Z and 16AA show a new hierarchial network topology.

Although the FIG. 9 network structure is simple and produces reasonable results in loosely coupled problems like geographic searches described earlier, as a general approach it has at least three important problems.

First, as the number of personal computers PC 1 being used in the network grows, an increasingly greater deal of complex pre-operation planning and custom tailoring-type programming at the master PC 1 level is required to establish a means for allocating portions of the operation among the large number of available personal computers PC 1'.

Second, operations results coming back to PC 1 from personal computers PC 1' are not synchronized, so that PC 1 frequently alternates between being idle and being overwhelmed. When the number of personal computers PC 1' is very large, both problems can be significant; when the number is massive, the problems can be overwhelming and seriously degrade the operation of the network.

Third, generally there is no means established for personal computers PC 1' to communicate or cooperate with each other during such network operations, so sharing operational results during processing between personal computers PC 1' is usually not feasible, especially when large numbers of PC 1 are involved. Consequently, closely coupled problems are generally not amenable to solution by conventional parallel processing by computers using a simple bus-type network like FIG. 9.

The new hierarchical network topology shown in FIG. 16A is a simple subdivision step thereby a personal computer PC 1 (or equivalent PC on a microprocessor chip 90) or microprocessor 30 acting as a master $M_1$ divides a given operation into two parts (for example, two halves), then sends by an optical or electrical connection such as optical fiber or wire 99 the one half parts to each to two connected available slave personal computers PC 1 (or PC microprocessor 90) or microprocessor 30, as shown one processing level down as $S_{21}$ and $S_{22}$. The FIG. 16A (and subsequent FIGS. 16) can be connected to the Internet 3 and World Wide Web, as preferred, or may not be so connected but still with benefit.

FIG. 16B shows that slave personal computer PC 1 (or PC microprocessor 90) or microprocessor 40 located at $S_{21}$ has temporarily adopted the same functional role as a master to repeat the same subdivision of the given operation. Therefore, having already been divided in half once in FIG. 16A, the given operation is again subdivided in FIG. 16B, this time in half into quarters of the original operation (for example) by $S_{21}$, which then sends one quarter to each of two additional available slave personal computers PC 1 (or PC microprocessors 90) or microprocessors 40 located at $S_{31}$ and $S_{32}$.

FIG. 16C shows personal computers PC 1 (or PC microprocessor 90) or microprocessors 40 at $S_{31}$ and $S_{32}$ sending operation results back to $S_{21}$ after performing the processing required by the given operation, instead of repeating again the subdivision process. That processing action by $S_{31}$ and $S_{32}$ can be dictated by pre-established program criteria, for example by automatically defaulting to operational processing at the $S_3$ level after two subdivision processes as shown above, so that the operation can be processed in parallel by four available slave personal computers PC 1 (or PC microprocessors 90) or microprocessors 40. Alternately, as another example, the criteria can be a user preference command overriding an otherwise automatic default to level three processing in order to specify some other level of processing involving more or less slave PC 1 (or PC microprocessors 90) or microprocessors 40.

Similarly, in FIG. 16A above, the personal computer PC 1 (or PC microprocessor 90) or microprocessor 40 acting as master $M_1$ also can initiate the parallel processing operation (or, alternatively, a multi-tasking operation) on the basis of a preset program parameters through software, hardware, or firmware or other means; parameter examples again being pre-set automatic default or user preference over-ride.

Like FIG. 16C, FIG. 16D shows operation results being passed back to the next higher level, this time from slave personal computers PC 1 (or PC microprocessors 90) or microprocessors 40, $S_{21}$ and $S_{22}$, to master personal computer PC 1 (or PC microprocessor 90) or microprocessor 30, $M_1$, where the operation is completed after the $S_{21}$ and $S_{22}$ results are consolidated.

FIG. 16G shows master personal computer PC 1 (or PC microprocessor 90) or microprocessor 30, $M_1$, offloading by wireless connection 100, for example, the entire parallel processing operation to an available slave personal computer PC 1 (or PC microprocessor 90) or microprocessor 40 that temporarily functions as $S_1$ in the place of $M_1$ on the first processing level for the duration of the given parallel processing (or multi-tasking) operation, the first step of which operation is shown in FIG. 16H, which is like FIG. 16A except as shown.

FIG. 16I shows a personal computer PC 1 (or PC microprocessor 90) or microprocessor 40 that is executing a command to function in the slave role of $S_{21}$ for a given operation but has become unavailable, or was unavailable initially, (due, for example, to interruption for other higher priority command by its user or to malfunction) when results of the given operation from a lower parallel processing level are passed to $S_{21}$. In that situation, $S_{21}$ (or $S_{31}$ or $S_{32}$) can simply offload those results to another personal computer PC 1 (or PC microprocessor 90) or microprocessor 30 (or 40) that is then available and it can become $S_{21}$ and take over the role of $S_{21}$ in the given operation for the duration of that operation. Similarly, the role of any unavailable or malfunctioning master or slave PC 1 or microprocessor 90, 30, or 40 can be transferred to an available functioning one.

As shown in FIG. 16J, $S_{21}$ then completes the parallel processing operation and passes its portion of the operation results to $M_1$.

The offloading capability of functional roles of master and slave personal computers PC 1 (and PC microprocessors 90) and microprocessors 30 (and 40) from unavailable to available PC 1, 30 and 40 as shown in FIGS. 16G-16J can also be used in previous figures in this application. In the simplest case initially, all processing roles of personal computers PC1 (and PC microprocessors 90) and microprocessors (30 or 40), like $S_{21}$, above can be determined at the beginning of an operation based on availability (based on non-use and lack of malfunctioning component) and remain unaltered until the end of the operation. But, with more sophisticated system software and hardware and firmware, during an operation any number of the processing roles can be offloaded from personal computers PC 1 (or PC microprocessors 90) or microprocessors 30 (or 40) to others as required, even multiple times and many simultaneously.

FIG. 16E shows the multi-processing network topology of FIGS. 16A-16J in a larger scale embodiment, including all personal computers PC 1 (or PC microprocessors 90) or microprocessors 30 (or 40) that are participating in a typical operation, including in this example one personal computer PC 1 (or PC microprocessor 90) or microprocessor 30 (or 40) at level one; two at level two; four at level three; and eight at level four. The network topology is completely scalar in that any practical number of additional processing levels or personal computers PC 1 (or PC microprocessors 90) or microprocessors 30 (or 40) can be added to those shown (and topologies limited to just two (or three) levels are also possible, which is the simplest case of operation processing subdivision that distinguishes over the conventional FIG. 9 single level "string-together" architecture).

Note that the number of processing personal computers PC 1 (or PC microprocessors 90) or microprocessors 40 doubles at each additional processing level and therefore can be represented by $2^N$, where N is the last or final processing level, for the simplest case, as shown above, which is splitting one given operation into two parts such as halfs between each level.

Note also that instead of subdividing one operation as above, two separate parallel processing operations can be multi-tasked on separate branches, such as $S_{21}$ and $S_{22}$ as shown, using the same network architecture described above. As is clear from this example, any practical mix of multi-tasking and/or parallel processing is possible using the above network architecture.

FIG. 16E shows the distribution of a given parallel processing (or multi-tasking) operation as routed through a four level virtual network, beginning at $M_1$. "Virtual" as used here means temporary, since in the next parallel operation originating at $M_1$ it might be the case that many of the personal computers PC 1 (or microprocessors 90) or microprocessors 30 (or 40) that had been available for a previous operation would not still be available for the next operation.

As FIG. 16E shows a binary tree network architecture for the initial distribution of an operation from $M_1$ down through four slave processing levels, while FIG. 16F shows the subsequent processing and accumulation of results back from there to $M_1$. FIG. 16F shows an inverted view of FIG. 16E to show the sequence of the operation, from operation distribution in FIG. 16E to result accumulation in FIG. 16F.

More specifically, FIG. 16F shows the processing slave personal computers PC 1 (or PC microprocessors 90) or microprocessors 40 at the fourth level, $S_{41}$, through $S_{48}$, where they process the operation to produce results which are then routed back through two other levels of the virtual network to $M_1$.

In the routing of operation results shown in FIG. 16F, each slave personal computer PC 1 (or PC microprocessor 90) or microprocessor 40) has the capability to either simply pass through those results operation only as a direct communication link or connection; or, alternatively, for example, to consolidate those results sent from the personal computers PC 1 (or PC microprocessor 90) or microprocessors 40) at a lower level; or, to provide additional other processing based on those lower processing level results.

Such consolidation or additional processing can reduce or eliminate duplicative data from a search or other operation producing duplicative results and can also serve to buffer the originating master $M_1$ from overloading caused by many sets of results arriving at $M_1$ in the FIG. 9 single processing level architecture in an uncoordinated fashion from what might be a large number of slave personal computers PC 1 (or PC microprocessor 90) or microprocessors 40. Such a consolidation role for personal computers PC 1 (or PC microprocessor 90) microprocessors 40 substantially reduces or eliminates the excessive custom pre-planning and synchronization problems of the conventional FIG. 9 network topology discussed above.

FIG. 16K shows a simple example indicative of the extremely complicated network structure that can result from subdividing a given operation in which the complexity of the operation involved is not uniform, due to, for example, variations in the data. In this example, pre-set program splitting criteria can be employed that balances the processing load of each slave personal computer PC 1 (or PC microprocessor 90) or microprocessor 40. With this approach, the complex portions of a given operation can automatically draw greater resources in the form of additional splitting of that more difficult portion of the problem, so that additional levels of parallel processing slave personal computers PC 1 (or PC microprocessors 90) or microprocessors 40 can be brought into the virtual network to process the operation, as shown in the left branch of FIG. 16K.

FIG. 16K is a fairly simple example, but when the same kind of dynamic network structure is applied to a virtual network using many more personal computers PC 1 (or PC microprocessor 90) or microprocessors 30 or 40 and many processing levels, involving both micro levels in PC microprocessor chips 90 and macro levels in personal computers PC 1 networks (such as shown later in FIG. 20B) then the potential complexity of the virtual network increases significantly. For example, each PC microprocessor chip 90 might have 64 slave microprocessors 94 on the final processing level; each personal computer PC 1 might have 64 slave PC microprocessor chips 90 at the final processing level, and the virtual network might include 64 personal computers PC 1 at the final processing level. With this large number of physical resources available (which can of course be very substantially greater) to the virtual network created by processing a given operation or operations, like that shown in FIG. 16K, it is clear that the operation itself can sculpt an incredibly complex virtual network that is custom tailored to the specific operation. All that is required is a operation subdivision process as described earlier that can be resident in each PC 1 (or PC microprocessor 90) or microprocessor 30 or 40, or that can be passed along with data (as can be operation application software) as the operation is executed.

Thus, FIG. 16K shows an example of a highly flexible virtual network architecture that is capable of being dynamically configured in real time by the processing requirements imposed on the components of the network by a specific given operation and its associated data, as allowed by the network hardware/software/firmware architecture.

FIGS. 16L and 16M show examples of other possible subdivision parallel processing methods, such as subdivision routing to three slave personal computers PC 1 (or PC microprocessors 90) or microprocessors 40 at the next level down, as shown in FIG. 16L, or subdivision routing to four slave personal computers PC 1 (or PC microprocessors 90) or microprocessors 40, as shown in FIG. 16M. Subdivision routing to any practical number of slave personal computers PC 1 (or PC microprocessors 90) or microprocessors 40 between processing levels can be done.

Such routing subdivision can also vary between processing levels or even within the same processing level, as shown in FIG. 16N; these variations examples can result from pre-set program criteria such as those that balance operation loads, like those shown previously in FIG. 16K. The means for subdividing problems for parallel or multi-tasking processing can also vary, within at least a range of methods known in the computer and mathematical arts.

FIG. 16O shows slave personal computer PC 1 (or PC microprocessor 90) or microprocessor 40, $S_{41}$, sending operation results to a higher processing level, $S_{31}$, which can then function as a router or as one or more high speed switch 42 (which can be located as 92 on a PC microprocessor 90 also, including as an all optical switch), passing through unaltered the results back down to the original level to personal computer PC 1 (or PC microprocessor 90) or microprocessor 40, $S_{42}$, as shown in FIG. 16P. FIG. 16Q demonstrates the capability for any two pair of slave personal computers PC 1 (or PC microprocessors 90) or microprocessors 40 like $S_{41}$ and $S_{42}$ to communicate directly between each other, including wired or wirelessly 100 as shown. FIGS. 16O-16Q shown the same subsection of the network topology shown in FIG. 16F (the left uppermost portion), as are the next FIGS. 16V-16W below.

A personal computer PC 1 (or PC microprocessor 90) or microprocessor 30 (or 40) located on a higher processing level in the network architecture such as $S_{31}$ can process results as well as route them, as shown in FIG. 16V, in which $S_{31}$ receives results from $S_{41}$ and $S_{42}$ at a lower processing level and then processes that data before sending its processing results to a higher level to $S_{21}$, as shown in FIG. 16W.

Together, FIGS. 16V-16W and 16O-16Q show the capability of any personal computer PC 1 (or PC microprocessor 90) or microprocessor 30 (or 40) of the FIG. 16F (and 16E) network structural and functional invention to communicate with any other personal computer PC 1 (or PC microprocessor 90) or microprocessor 30 (or 40) participating in a given parallel processing (or multi-tasking) operation. That communication can take the form of simple pass-through of unmodified results or of modification of those results by processing at any level.

FIGS. 16X-16Z show the applicant's new hierarchical network structure and function applied to the design of a personal computer PC 1, as discussed previously in FIGS. 10A and 10B. FIG. 16X shows the simplest general design, with a master $M_1$ microprocessor 30 and two slave $S_{21}$ and $S_{22}$ microprocessors 40. FIG. 16Y shows the same network structure with an additional level of slave microprocessors 40, $S_{31}$ through $S_{34}$, while FIG. 16Z shows the same network structure as FIG. 16Y with an additional level of slave microprocessors 40, $S_{41}$ through $S_{48}$. As shown in these examples, this network structure is completely scalar, including any practical number of slave microprocessors 40 on any practical number of processing levels.

FIG. 16AA shows a useful embodiment in which each microprocessor 30 and 40 has, in addition to internal cache memory, its own random access memory (RAM) 66 or equivalent memory (volatile or non-volatile, like Flash or magnetic memory), integrated on chip or separate off chip. A significant amount of such RAM or other memory, significantly greater than "cache" memory and other on chip memory used on microprocessor chips today, can be beneficial in improving the efficient operation of the microprocessor; if located off microprocessor chip, the size of such memory can substantially exceed the size of the associated microprocessor, but on microprocessor chip location like cache memory offers the best potential for improving microprocessor speed and efficiency. The design can also incorporate (or substitute) conventional shared memory or RAM 66' (i.e. memory used by all, or some, of the microprocessors 30 or 40 (or 90) of the personal computer PC 1).

FIG. 16AB shows a direct connection of optical fiber 99 from Internet 3 (or another network) to random access memory (RAM) microchip 66'. The connection is preferably at a central portion 140 of RAM chip 66' to provide equal access to stored data on RAM chip 66'. The direct connection can be anywhere on RAM chip 66'. Digital signal processor (DSP) 89 is on RAM chip 66' for connection with optical fiber 99. RAM chip 66' is for shared memory use among PC's 1 and for broadcast use. RAM chip 66' can include volatile or non-volatile (flash-type) memory. RAM chip 66' can have more than one DSP 89, such as shown in FIG. 20B.

FIGS. 16R-16T are parallel to FIGS. 16X-16Z above, but show PC microprocessor 90 architecture rather than macro PC 1 architecture; a PC microprocessor 90 is, of course, as earlier described in FIG. 10C, a personal computer on a microchip.

FIG. 16U is like FIG. 16AA, also except for showing PC microprocessor 90 architecture instead of PC 1 architecture. FIG. 16U shows a useful embodiment in which each PC microprocessor 93 or 94 has its own integrated on chip (or separate off chip) random access memory (RAM) 66 or equivalent memory (volatile or non-volatile, like Flash or magnetic memory). A significant amount of such RAM or other memory, significantly greater than "cache" memory or other on chip memory used on microprocessor chips today, can be beneficial in improving the efficient operation of the microprocessor; if located off microprocessor chip, the size of such memory can substantially exceed the size of the associated microprocessor, but on microprocessor chip location like cache memory offers the best potential for improving microprocessor speed and efficiency. The microchip design can also incorporate (or substitute) conventional shared memory or RAM 66' (i.e. memory used by all, or some, of the PC microprocessors 93 or 94 of the personal computer PC microprocessor 90).

FIGS. 16R-16U show a different and improved basic chip architecture which can exclude or reduce the currently used superscalar approach in microprocessors to execute multiple instructions during each clock cycle. The FIGS. 16R-16U architecture is much simpler and, by integrating memory with microprocessor, reduces memory bottlenecks. The simplicity of the FIGS. 16R-16U microchip design, which might have little or no superscalar components, compared to conventional superscalar designs (the inherent extreme complexity of which creates a very substantial memory overhead) can result in the use of a much greater proportion of independent, non-superscalar processors per microchip, exclusive of integrating memory or RAM 66 onto the microprocessor chip 90, as discussed in FIG. 16U.

FIGS. 16X-16Z and 16AA, by using the same architecture for PC 1 networks as FIGS. 16R-16U, import the same advantage of microchip parallel processing performance to parallel processing in PC 1 networks.

All FIGS. 16A-16Z and 16AA, like the preceding figures of this application, show sections of a network of personal computers PC 1 (or PC microprocessors 90) or microprocessors 30 or 40 which can be parts of the WWW or Internet or Internet II or the Next Generation Internet (meaning connected to it) or Intranets or Extranets or other networks.

Also, except for FIGS. 16R-16T and 16X-16Z, all of the FIG. 16 series show personal computers PC 1 and microprocessors 30 or 40 as occupying the same location. This dual representation was done for economy of presentation and to show the parallel functionality and interchangability in conceptual terms of personal computer PC 1 and microprocessors 30 or 40 in the structure of the new network. So, taking FIG. 16A as an example, $M_1$, $S_{21}$ and $S_{22}$ show three personal computers PC 1 or, alternatively, one microprocessor 30 and two microprocessors 40.

And, as noted initially in FIG. 10C, a personal computer PC 1 can be reduced in size to a PC microprocessor chip 90, so preceding Figures showing personal computer PC 1 also generally represent PC microprocessor chip 90.

Finally, the FIGS. 16A-16Z and 16AA show a mix of electrical and optical connections, including wired 99, especially connections such as optical glass fiber and wireless 100 (and mixtures of both in a single figure). Generally, either 99 or 100 or a mix can be used relatively interchangeably in the network inventions shown (as well as in prior figures), though in some embodiments either highest transmission speed (ie broadest bandwidth) or mobility (or some other factor) may dictate a preferred use of wired or wireless. Generally, fiber optic wire 99 provides the most advantageous transmission means because it has the greatest bandwidth or data transmission speed, so it is generally preferred for connections between personal computers and microchips, including direct connections, whereas wireless 100 is generally preferred where mobility is a paramount design criteria.

Any of the embodiments shown in FIGS. 16A-16Z and 16AA can be combined with any one or more of the preceding or subsequent figures of this application.

The parallel processing network architecture shown in the preceding FIGS. 16A-16Z and 16AA and in earlier figures has several features unique to its basic design that provide for the security of personal computers PC 1 (or PC microprocessor 90) or microprocessor 40 that share other computers for parallel and multi-tasking processing. First, the slave personal computers PC 1 (or microprocessors 40) each have only part of the operation (for large operations, only a very small part) and therefore unauthorized surveillance of a single PC 1 can provide only very limited knowledge of the entire operation, especially in only a relatively local area switching or routing was employed. Second, the addresses of the slave personal computers PC 1 (or microprocessors 40) are known or traceable, therefore not protected by anonymity (like hackers usually are) in case of unauthorized intervention. In addition, cryptography can be employed, with on microprocessor chip 30, 40, or 90 hardware 55 preferred due to efficiency, although software and firmware can also be used, or a separate PC 1 hardware-based component 56 like an encryption microchip can be used; with either encryption component 55 or 56, micro mechanical locks can be used to prevent access other than the direct physical user. Nonetheless, these inherent strengths can be substantially reinforced, as indicated in FIGS. 17B-17D.

Figure 17A:
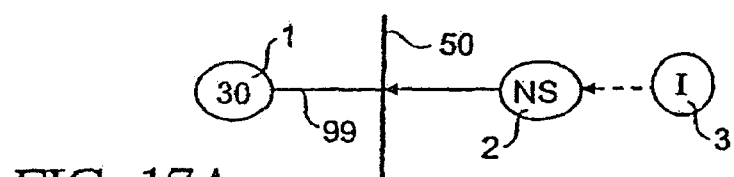
FIGS. 17A-17D show a firewall 50 with a dual function, including that of protecting Internet users (and/or other network users sharing use) of one or more slave personal computers PC 1 or microprocessors 40 from unauthorized surveillance or intervention by an owner/operator of those slave processors.

FIG. 17A shows at least one firewall 50 performing its conventional function of keeping out intruders such as hackers from the Internet 3 from unauthorized access for either surveillance or intervention of a user's personal computer PC 1 (or PC microprocessor 90) or master microprocessor 30.

Figure 17B:
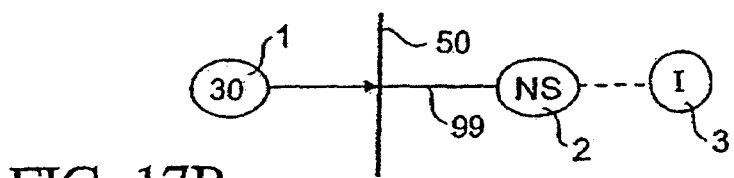

FIG. 17B shows that, since Internet users can, as enabled by the applicant's network structure invention, use one or more of the slave microprocessors 40 of another's personal computer PC 1 (or PC microprocessor 90) for parallel (or multi-tasking) processing, the at least one firewall 50 has a dual function in also protecting Internet 3 use (or other shared use on a network) from unauthorized surveillance or intervention by a PC 1 owner/user who is providing the shared resources. To maintain the privacy necessary to operate such a cooperatively shared network arrangement, unauthorized surveillance or intervention must be carefully prevented by hardware/software/firmware or other means.

Figure 17C:
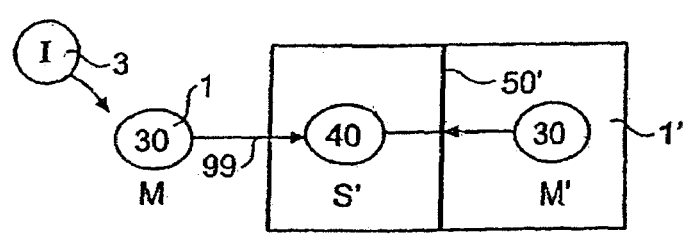
Figure 17D:
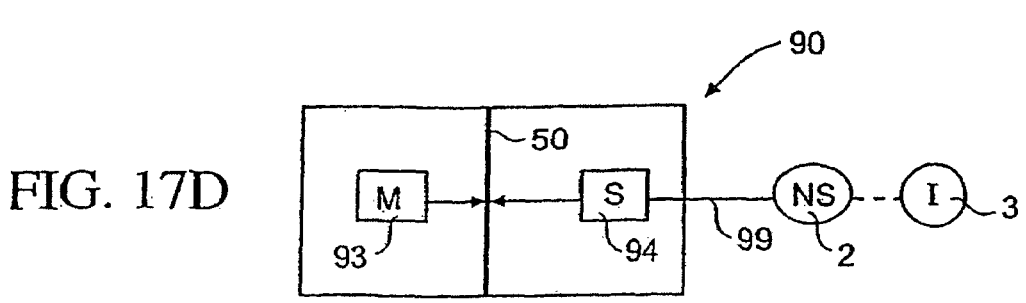

FIG. 17C therefore shows master M personal computer PC 1 (or PC microprocessor 90) using the slave S₂ microprocessor 40 of a different personal computer, PC 1', which is available for Internet 3 (or other net) shared use, while firewall 50' blocks unauthorized access into PC 1' by PC 1 (although PC 1' owner/user can always interrupt a shared operation and take back control and use of slave S' microprocessor 40, which then triggers off-loading action to compensate, as discussed above in FIGS. 16I-16J).

FIG. 17D shows a figure similar to FIG. 17C, but showing a PC microprocessor 90 with a slave microprocessor 94 being used by Internet 3 users (or other net), so that at least one firewall 50 serves both to deny access such as surveillance by master M microprocessor 93 to an Internet 3 parallel processing (or multi-tasking) operation on slave S microprocessor 94 and to deny access to master M microprocessor 93 by Internet 3 (or other net) users of slave S microprocessor 94. It is presently contemplated that at least one firewall 50 is implemented by non-configurable hardware at the microchip level to provide the best protection against tampering with the firewall 50 by a PC 1 user, who has easier access to software or macro hardware such as PC motherboards to alter.

The flexible network architecture shown earlier in FIG. 16K and other FIG. 16 series (and other figures) have many applications, including their use to design improvements and alternatives to the network itself. In addition, the flexible network can be used to simulate and design personal computers PC 1 and particularly PC microprocessor chips 90 (and other microchips), which may be static or configurable (in response to the requirements of a given operation, like the FIG. 16K network architecture) or a mix.

The FIG. 16K network architecture has capabilities that substantially exceed simulating the fairly simple binary circuit structure of a typical PC microprocessor 90 or other microchip, since any personal computer PC 1 or PC microprocessor chip 90 in the FIG. 16K network can simulate much more than a simple binary circuit on/off state or other simple microchip circuit. Any PC 1 or 90 in a FIG. 16K network can represent virtually any number of states or conditions simulating any kind of circuit, however complex it might be, the only limit being the processing time required for what can be a very large number—thousands or millions—of personal computers PC 1 or PC microprocessors 90 to process the simulation; that is to say, there are only practical constraints, not theoretical ones, although increasingly larger numbers of processors are expected to be phased in, as discussed before.

One potential related application of prior described network inventions is to simulating the unique "qubit" component necessary to construct a quantum computer, as well as a virtual quantum computer itself.

Figure 18A:
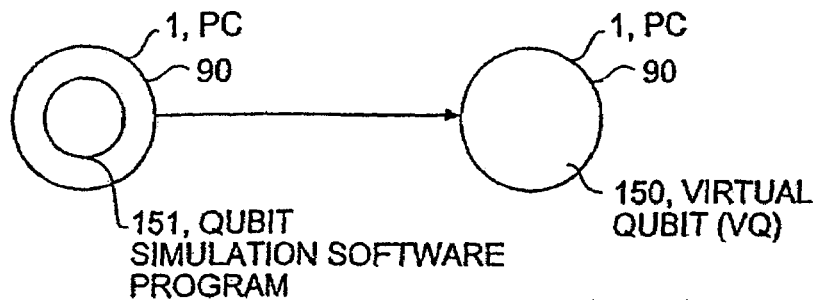
FIGS. 18A-18D show designs for one or more virtual quantum computers integrated into one or more digital computers.
Figure 18B:
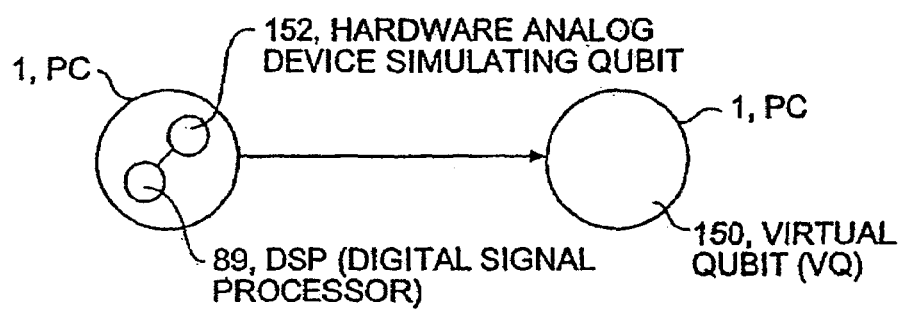

FIGS. 18A-18D show designs for a virtual quantum computer or computers. FIG. 18A shows personal computer PC 1 (or microprocessor 90) with the addition of a software program 151 simulating a "qubit" for a quantum computer or computers and thereby becoming a virtual qubit (VQ) 150, a key component of a quantum computer 153. FIG. 18B shows a personal computer PC 1 (or microprocessor 90) with a digital signal processor (DSP) 89 connected to a hardware analog device 152 simulating a qubit, with the PC 1 monitoring the qubit through the DSP 89, thereby simulating a virtual qubit (VQ) 150 for a quantum computer 153; this arrangement allows the option of simultaneous use of the PC 1 through multi-tasking for both digital and quantum computing.

Figure 18C:
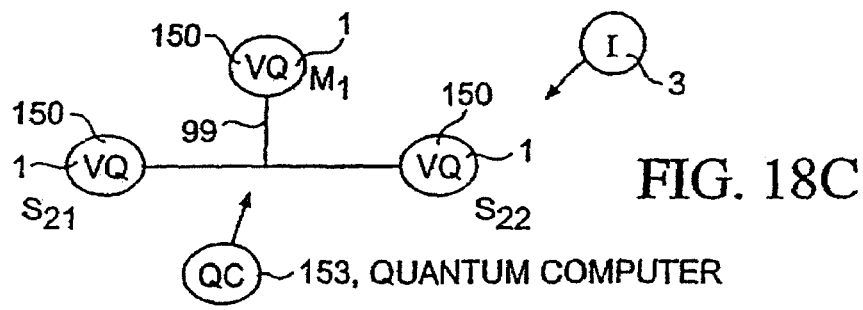

FIG. 18C is like FIG. 16A, but incorporating a virtual qubit in PC 1, so that a virtual quantum computer 153 can have any network architecture like those shown in FIGS. 16A-16Z and 16AA, as well as other figures of this application.

Figure 18D:
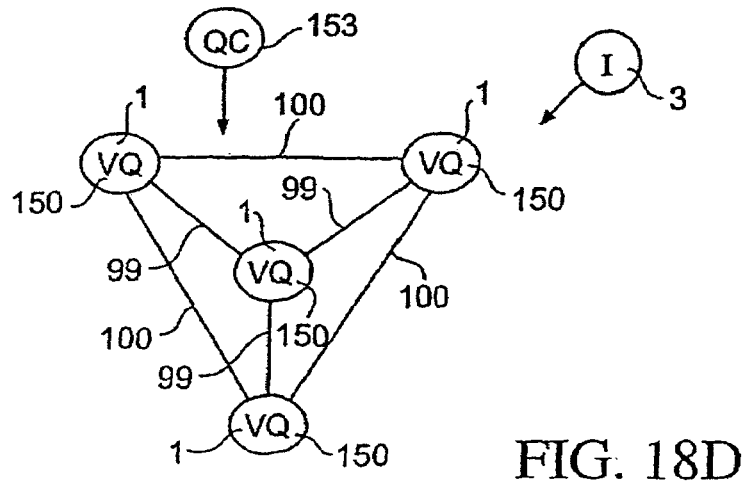

As shown in FIG. 18D, for example, a virtual qubits (VC) 150 network can provide complete interconnectivity, like FIG. 13. Virtual qubits VC 150 like those described in FIGS. 18A & 18B can be added to or substituted for microprocessors 30 and 40 in prior FIGS. 16B-16Q and 16V-16AA of this application, as well as earlier figures. As shown in those prior applications, the number of virtual qubits 150 is limited only to whatever is practical at any given time; in terms of development that means as few as a single qubit 150 in one or more networked personal computers PC 1 to begin, but the number of qubits 150 can become potentially extremely large, as indicated in previous figures. FIG. 18D shows a mix of wired 99 and wireless 100 connections.

Like personal computers located in the home or office, personal computers PC 1 in automobiles 170 (including other transportation vehicles or other conveyances) are in actual use only a very small percentage of the time, with the average dormant period of non-use totaling as much as 90 percent or more. Personal computers PC 1 are now being added to some automobiles and will likely become standard equipment over the next decade or so. In addition, automobiles already have a very large number of microcomputers onboard in the form of specialized microprocessors 35 which are likely to become general parallel processors in future designs, as discussed earlier in this application.

Figure 19:
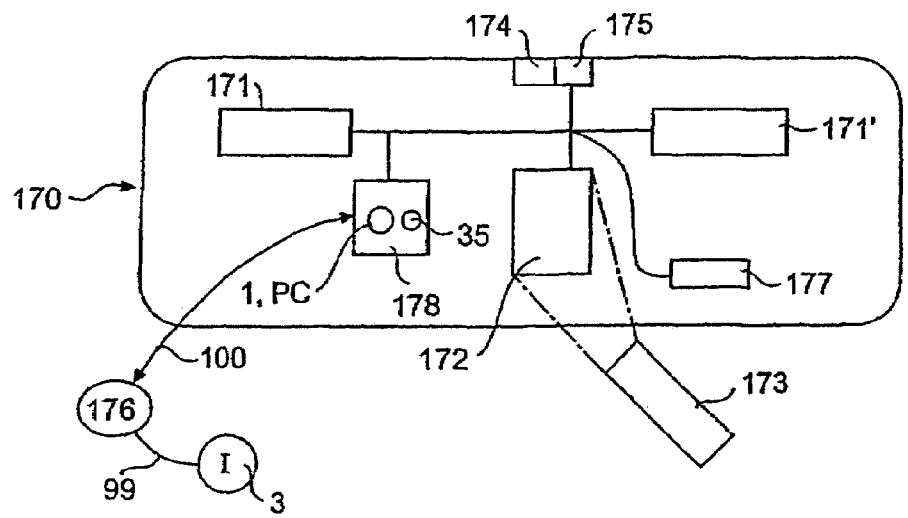
FIG. 19 shows special adaptations to allow the use of idle automobile computers to be powered and connected to the Internet (or other net) for parallel or multi-tasking processing.

Automobiles therefore form a potentially large and otherwise unused resource for massive parallel processing through the Internet 3 and other networks, as described in earlier figures. However, when idle and thus generally available for network use, automobiles lack their usual power source, the engine, which of course is then off, since it is too large to efficiently provide electrical power to onboard computers except occasionally. As shown in FIG. 19, the car engine can have a controller (hardware, software or firmware or combination in the PC 1 (or other microprocessor 35), for example, connected to an automobile computer network 178 to automatically start the automobile engine in order to recharge the car battery 171 when the battery is low (and well before the battery is too low to start the engine), but the engine additionally needs to be controlled as above not to expend all available fuel automatically.

Alternately, the automobile 170 can be fitted with a very small auxiliary engine-power electrical power generator 177 to provide power to the automobile's computer network; the engine of the generator 177 can be fed by the main engine fuel tank and controlled as above.

Two solutions, not mutually exclusive, to alleviate (but not solve) the lack of power problem noted above are, first, adding an additional car battery 171' for network use (at least primarily) or, second, using a single battery but adding a controller in the PC 1, for example, that prevents the existing battery 171 from being discharged to a level near or below that which is needed to start the automobile 170.

In addition, as shown in FIG. 19, one or more solar power generating cells or cell arrays 172 can be incorporated in an automobile's outer surface, with generally the most effective placement being on a portion of the upper horizontal surface, such as a portion of the roof, hood, or trunk. For charging the automobile battery 171 when sunlight is not available, such as at night or in a garage, a focused or focusable light source 173 can provide external power to the solar panel.

Alternately, a connection device 174 such as a plug for an external electrical power source can be installed on or near the outer surface of the automobile. In addition, or independently, a connection device 175 for an optical fiber (or other wired) external connection to the Internet 3 or other net; an intermediate high transmission speed can also exist between the automobile network and a fiber optic connection to the Internet 3. Alternately, a wireless receiver 176 located near where the automobile is parked, such as in a garage, can provide connection from the automobile's personal computer or computers PC 1 directly to the Internet 3 or to a network in a home or business like that shown in FIG. 10I.

Figure 20A:
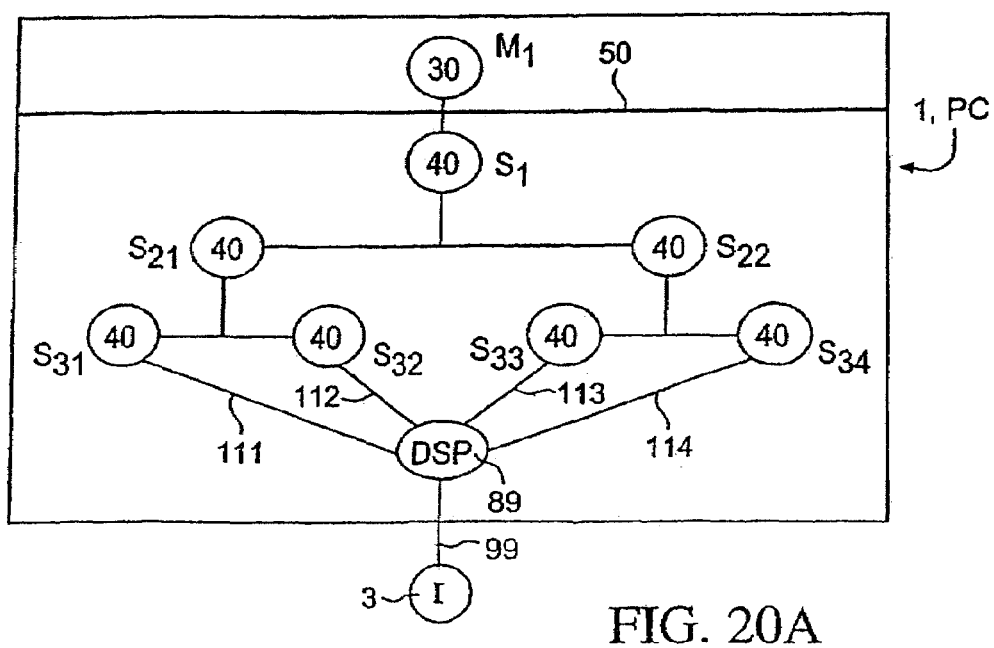
FIGS. 20A and 20B show separate broad bandwidth outputs such as an optical connection like glass fiber from each microprocessor 40 or 94.
Figure 20B:
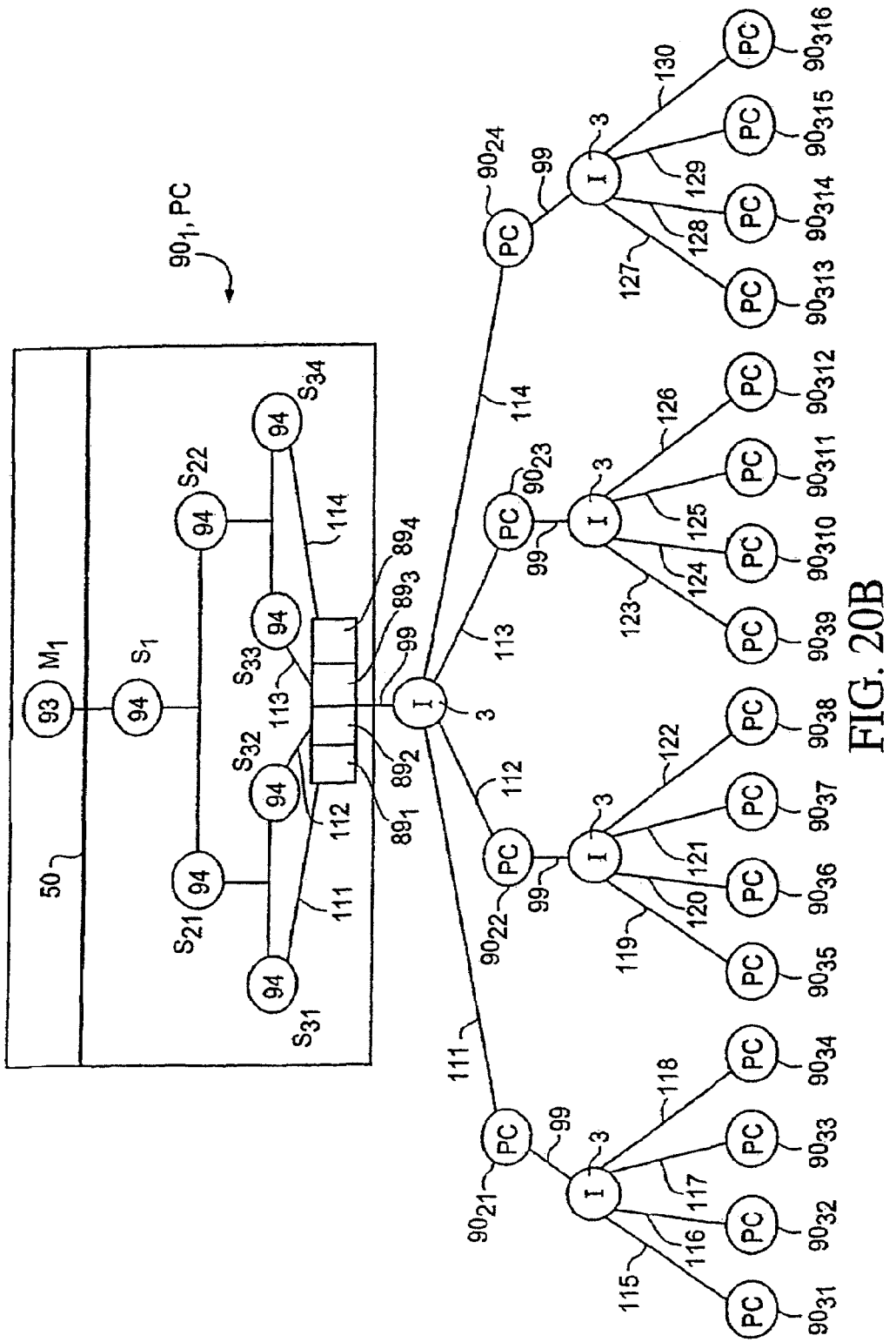

FIG. 20A is like FIG. 16Y, but in addition shows a slave microprocessor 40 functioning as $S_1$, the function of master having been temporarily or permanently offloaded to it by $M_1$ microprocessor 30. Also in addition, FIG. 20A shows the processing level of slave microprocessors 40, $S_{31}$ through $S_{34}$, each with a separate output link to a digital signal processor (DSP) 89 or other transmission component; the transmission linkages are shown as 111, 112, 113, and 114, respectively. The DSP 89 is connected to a wired 99 means such as optical fiber to the Internet (or other net), although non-optical fiber wire can be used (and probably does not require a DSP 89).

FIG. 20B is like FIG. 16S, but with the same new additions described above in FIG. 20A. Like FIG. 16S, FIG. 20B shows a detailed view of personal computer PC microprocessor $90_1$, which is a personal computer on a microchip, including two more levels of parallel processing within the microprocessor 90. In addition, the two new levels of PC microprocessor 90 shown in FIG. 20B are a second processing level consisting of PC microprocessors $90_{21}$ through $90_{24}$ and a third processing level consisting of PC microprocessors $90_{31}$ through $90_{316}$ (a third level total of 16 microprocessors 90). Each of the three processing levels shown in the FIG. 20B example is separated between levels by an intermediate direct connection to the Internet 3 (or other network) and by four output lines from the higher processing level. For example, microprocessors $90_{21}$ through $90_{24}$ are shown receiving respectively from the outputs 111 through 114 from four slave microprocessors 94, $S_{31}$ through $S_{34}$ of PC microprocessor $90_1$.

Note that PC microprocessor $90_1$ is shown in detail including all slave microprocessors 94, while other PC microprocessors 90 at the second and third processing levels do not, for simplicity and conciseness of presentation. Note also that an additional processing level can be present, but is not shown for the sake of simplicity: personal computers PC 1 like FIG. 20A can be used interchangeably with PC microprocessors 90.

FIG. 20B shows that between each processing level the output links from every PC microprocessor 90 can be transmitted from slave microprocessors 94 directly to PC microprocessors 90 at the next processing level below, such as from PC microprocessor $90_{21}$ down to PC microprocessors $90_{31}$ through $90_{34}$, via the Internet 3 or other net. Each of the transmission links from those slave processing microprocessors 94 ($S_{31}$ through $S_{34}$), shown as 111, 112, 113, and 114 for PC microprocessor $90_1$, can be transmitted on a different channel (and can use multiplexing such as wave or dense wave division) on an optical fiber line (because of its huge capacity, one optical fiber line is expected to be sufficient generally, but additional lines can be used) that connects preferably directly to PC microprocessor chip $90_1$, which can incorporate a digital signal processor 89 (of which there can be one or more) for connecting to the wired connection like fiber optic line, as shown, or wireless connection.

Any of the embodiments shown in FIGS. 20A and 20B can be combined with one or more of any of the preceding figures of this application.

This application encompasses all new apparatus and methods required to operate the above described network computer system or systems, including any associated computer or network hardware, software, or firmware (or other component), both apparatus and methods. Specifically included, but not limited to, are (in their present or future forms, equivalents, or successors): all enabling PC and network software, hardware, and firmware operating systems, user interfaces and application programs; all enabling PC and network hardware design and system architecture, including all PC and other computers, network computers such as servers, microprocessors, nodes, gateways, bridges, routers, switches, and all other components; all enabling financial and legal transactions, arrangements and entities for network providers, PC users, and/or others, including purchase and sale of any items or services on the network or any other interactions or transactions between any such buyers and sellers; and all services by third parties, including to select, procure, set up, implement, integrate, operate and perform maintenance, for any or all parts of the foregoing for PC users, network providers, and/or others.

The combinations of the many elements the applicant's invention introduced in the preceding figures are shown because those embodiments are considered to be at least among the most useful possible, but many other useful combination embodiments exist but are not shown simply because of the impossibility of showing them all while maintaining a reasonable brevity in an unavoidably long description caused by the inherently highly interconnected nature of the inventions shown herein, which generally can operate all as part of one system or independently.

Therefore, any combination that is not explicitly described above is definitely implicit in the overall invention of this application and, consequently, any part of any of the preceding Figures and/or associated textual description can be combined with any part of any one or more other of the Figures and/or associated textual description of this application to create new and useful improvements over the existing art.

In addition, any unique new part of any of the preceding Figures and/or associated textual description can be considered by itself alone as an individual improvement over the existing art.

The forgoing embodiments meet the overall objectives of this invention as summarized above. However, it will be clearly understood by those skilled in the art that the foregoing description has been made in terms only of the most preferred specific embodiments. Therefore, many other changes and modifications clearly and easily can be made that are also useful improvements and definitely outside the existing art without departing from the scope of the present invention, indeed which remain within its very broad overall scope, and which invention is to be defined over the existing art by the appended claims.

I claim as my invention:

1. A personal computer, comprising:
   at least one microchip, the at least one microchip comprising:
      at least four microprocessors, exclusive of any digital signal processors (DSPs);
      at least one non-volatile memory component;
      at least one power management component;
   at least one internal firewall with at least one hardware component, the at least one internal firewall being configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
   at least one wireless network connection mechanism configured to connect the personal computer to the at least one network, the at least one network comprising the Internet.

2. The personal computer of claim 1, wherein the at least one wireless network connection mechanism is configured to process at least one wireless signal that comprises multiplexing.

3. The personal computer of claim 1, wherein the at least one wireless network connection mechanism is configured to process at least one wireless signal that is wave division multiplexed (WDM).

4. The personal computer of claim 1, wherein the at least one internal firewall is at least one hardware firewall.

5. The personal computer of claim 4, wherein the at least one wireless network connection mechanism is located on the at least one microchip.

6. The personal computer of claim 4, wherein the at least one network comprises the World Wide Web.

7. The personal computer of claim 4, wherein the personal computer comprises only one microchip.

8. The personal computer of claim 4, wherein the personal computer is configured to function in the shared use with at least one second personal computer connected to the at least one network.

9. The personal computer of claim 8, wherein at least one second personal computer is idled by at least one personal user.

10. The personal computer of claim 4, wherein the at least one internal firewall is non-configurable hardware.

11. The personal computer of claim 4, wherein the shared use comprises shared file resources and/or message passing.

12. The personal computer of claim 4, wherein the shared use includes unauthorized shared use, including intrusion by hackers from outside the personal computer.

13. The personal computer of claim 4, wherein the shared use comprises multi-tasking or parallel processing.

14. The personal computer of claim 4, wherein the at least one microchip comprises at least one digital signal processor (DSP).

15. The personal computer of claim 4, wherein at least one random access memory (RAM) located on the at least one microchip comprises at least one non-cache memory.

16. The personal computer of claim 4, wherein the at least one microchip comprises at least 8 microprocessors, exclusive of any digital signal processors (DSPs).

17. The personal computer of claim 4, wherein the at least one wireless network connection mechanism is configured to process at least one wireless signal that is dense wave division multiplexed (DWDM).

18. The personal computer of claim 4, wherein the at least one network comprises at least one network server computer.

19. The personal computer of claim 4, wherein the at least one network comprises at least one Intranet.

20. The personal computer of claim 4, wherein the at least one internal firewall includes at least one firmware component.

21. The personal computer of claim 4, wherein the at least one internal firewall is configured to deny access to at least one first microchip microprocessor of the personal computer by at least one other computer connected to the at least one network during a shared use involving the personal computer and the at least one network.

22. The personal computer of claim 21, wherein the at least one internal firewall is further configured to allow access to at least one second microchip microprocessor of the at least one personal computer by the at least one other computer of the network during the shared use.

23. The personal computer of claim 22, wherein the at least one internal firewall is configured to deny access to the at least one first microchip microprocessor of the personal computer by the at least one network of computers during a shared use involving the personal computer and the at least one network.

24. The personal computer of claim 22, wherein the at least one internal firewall is configured to allow access to the at least one second microchip microprocessor of the personal computer by the at least one network during the shared use.

25. The personal computer of claim 24, wherein the at least one internal firewall is configured to deny access to the at least one second microchip microprocessor of the personal computer by at least one user of the personal computer during the shared use.

26. The personal computer of claim 4, wherein at least one the personal computer is intended for personal use by at least one individual owner and/or at least one leaser of the personal computer.

27. The personal computer of claim 4, wherein there is a at least one connection from the personal computer to the at least one network, the at least one connection having a speed of data transmission that is greater than a peak data processing speed of the personal computer.

28. The personal computer of claim 4, wherein the personal computer is controlled by at least one user of the personal computer through at least one wireless controller operated by the at least one user.

29. The personal computer of claim 4, wherein the at least one microchip comprises at least 16 microprocessors, exclusive of any digital signal processors (DSPs).

30. The personal computer of claim 4, wherein the at least one microchip provides at least one graphics function.

31. The personal computer of claim 4, wherein the at least one microchip comprises at least one modem component.

32. The personal computer of claim 4, wherein the at least one microchip provides at least one sound function.

33. The personal computer of claim 4, wherein the at least one microchip comprises at least one video function.

34. The personal computer of claim 4, wherein the at least one microchip comprises at least one magnetic memory component.

35. The personal computer of claim 4, wherein the at least one microchip comprises at least one BIOS (basic input/output system) component.

36. The personal computer of claim 35, wherein the at least one BIOS component is located on at least one flash memory component.

37. The personal computer of claim 4, wherein the at least one microchip comprises at least part of at least one system bus component.

38. The personal computer of claim 4, wherein the at least one microchip comprises at least one transponder.

39. The personal computer of claim 4, wherein the personal computer comprises: at least one handheld personal digital assistant, at least one wearable computer, at least one television, at least one digital set-top control box, at least one video game, at least one videocam, at least one compact disc (CD) or at least one digital video disk (DVD) player/recorder, at least one radio, at least one camera, at least one household electronic device, or at least one business electronic device, or any combination thereof.

40. The personal computer of claim 4, wherein the at least one microchip comprises at least 32 microprocessors, exclusive of any digital signal processors (DSPs).

41. The personal computer of claim 4, wherein the at least one microchip comprises at least 64 microprocessors, exclusive of any digital signal processors (DSPs).

42. The personal computer of claim 4, wherein the at least one microchip comprises at least one analog computer.

43. The personal computer of claim 4, wherein at least one system bus of the at least one microchip comprises at least one hierarchical connection architecture between at least some of the at least four microprocessors.

44. The personal computer of claim 43, wherein the at least one system bus comprises at least one binary tree network architecture between at least some of the at least four microprocessors.

45. The personal computer of claim 4, wherein the at least one microchip comprises at least 128 microprocessors, exclusive of any digital signal processors (DSPs).

46. The personal computer of claim 45, wherein at least some of the at least 128 microprocessors have at least one non-superscalar architecture.

47. The personal computer of claim 4, wherein the at least one microchip comprises at least 256 microprocessors, exclusive of the any digital signal processors (DSPs).

48. The personal computer of claim 4, wherein there is at least one direct optical fiber connection to the at least one microchip.

49. The personal computer of claim 4, wherein the at least one microchip is connected to a hard disk drive controlled by the at least one microchip.

50. The personal computer of claim 4, wherein the at least one microchip comprises at least one micro electromechanical (MEMS) component.

51. The personal computer of claim 4, wherein the at least one microchip comprises at least one integrated circuit with active configuration.

52. The personal computer of claim 51, wherein the at least one microchip comprises at least one field-programmable gate array.

53. The personal computer of claim 4, wherein the at least one microchip comprises at least 512 microprocessors, exclusive of any digital signal processors (DSPs).

54. The personal computer of claim 4, wherein the at least one microchip comprises at least one hardware encryption component.

55. The personal computer of claim 4, wherein the personal computer comprises at least one encryption microchip.

56. The personal computer of claim 4, wherein the personal computer comprises at least one telephone.

57. The personal computer of claim 4, wherein the at least one non-volatile memory component comprises at least one flash memory component.

58. The personal computer of claim 4, wherein the at least one microchip comprises at least 1024 microprocessors, exclusive of any digital signal processors (DSPs).

59. The personal computer of claim 58, wherein at least two of the microprocessors are used for parallel processing or multi-tasking.

60. The personal computer of claim 4, wherein the personal computer comprises a pager.

61. The personal computer of claim 4, wherein the personal computer is mobile.

62. The personal computer of claim 4, wherein the at least one microchip comprises a television function.

63. The personal computer of claim 4, wherein the at least one wireless network connection mechanism is configured to make at least one direct wireless connection to the at least one second personal computer, the at least one direct wireless connection being made without at least one network server or router.

64. The personal computer of claim 4, wherein the personal computer is configured for at least one substantially continuous wireless network connection.

65. The personal computer of claim 4, wherein there is also at least one optical fiber network connection being configured to connect the personal computer to the at least one network and to process at least one fiber optic signal that is wave division multiplexed.

66. The personal computer of claim 65, wherein the at least one optical fiber network connection mechanism is configured to process at least one fiber optic signal that is wave division multiplexed.

67. The personal computer of claim 4, wherein the personal computer comprises at least one automobile, at least one transportation device, or at least one robot, or any combination thereof.

68. The personal computer of claim 4, wherein the at least one microchip comprises at least one application-specific integrated circuit (ASIC).

69. The personal computer of claim 4, wherein the internal at least one hardware firewall is configured to deny all network access to at least a portion of the at least one non-volatile memory component.

70. The personal computer of claim 4, wherein the at least one microchip comprises at least two or four digital signal processors (DSPs).

71. The personal computer of claim 4, wherein said at least one internal firewall is configured to permanently deny access to portions of said at least one microchip from said at least one network.

72. A personal computer, comprising:
   at least one microchip, the at least one microchip comprising:
      at least four microprocessors, exclusive of any digital signal processors (DSPs),
      at least one power management component,
      at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall configured to deny access to portions of the at least one microchip from the at least one network; and
   at least one wireless network connection mechanism configured to connect the personal computer to the at least one network, the at least one network comprising the Internet.

73. The personal computer of claim 72, wherein the at least one internal firewall is configured to deny access to at least one first microchip microprocessor of the persona computer by at least one other computer connected to the at least one network during a shared use involving the personal computer and the at least one other computer of the at least one network, and
   the at least one internal firewall is further configured to allow access to at least one second microchip microprocessor of the at least one personal computer by the at least one other computer of the at least one network during the shared use;
   wherein the shared use includes unauthorized shared use, including intrusion by at least one hacker from outside the personal computer.

74. The personal computer of claim 73, wherein the at least one internal firewall is configured to deny access to the at least one first microchip microprocessor of the personal computer by the at least one network of computers during a shared use involving the personal computer and the at least one network; and
   wherein the shared use comprises shared file resources and/or message passing.

75. The personal computer of claim 73, wherein the at least one internal firewall is configured to allow access to the at least one second microchip microprocessor of the personal computer by the at least one other computer of the at least one network during the shared use.

76. The personal computer of claim 75, wherein the at least one internal firewall is configured to deny access to the at least one second microchip microprocessor of the personal computer by at least one user of the personal computer during the shared use.

77. The personal computer of claim 72, wherein said at least one microchip comprises at least 64 microprocessors.

78. The personal computer of claim 72, wherein said at least one microchip comprises at least 1024 microprocessors.

79. The personal computer of claim 72, wherein said at least one internal firewall is configured to permanently deny access to portions of said at least one microchip from said at least one network.

80. A personal computer, comprising:
   at least one microchip, the at least one microchip comprising:
      at least four microprocessors, exclusive of any digital signal processors (DSPs);
      at least one analog communications component;
      at least one power management component; and
      at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
   at least one wireless network connection mechanism configured to connect the personal computer to the at least one network, the at least one network comprising:
      the Internet.

81. The personal computer of claim 80, wherein the at least one internal firewall is configured to deny access to at least one first microchip microprocessor of the personal computer by at least one other computer connected to the at least one network during a shared use involving the personal computer and the at least one other computer of the at least one network, and
   the at least one internal firewall is further configured to allow access to at least one second microchip microprocessor of the at least one personal computer by the at least one other computer of the at least one network during the shared use;
   wherein the shared use includes unauthorized shared use, including intrusion by hackers from outside the personal computer.

82. The personal computer of claim 81, wherein the at least one internal firewall is configured to deny access to the at least one first microchip microprocessor of the personal computer by the at least one network of computers during a shared use involving the personal computer and the at least one network;
   wherein the shared use comprises shared file resources and/or message passing.

83. The personal computer of claim 81, wherein the at least one internal firewall is configured to allow access to the at least one second microchip microprocessor of the personal computer by the other at least one network during the shared use.

84. The personal computer of claim 83, wherein the at least one internal firewall is configured to allow access to the at least one second microchip microprocessor of the personal computer by the at least one network during the shared use.

85. The personal computer of claim 80, wherein said at least one microchip comprises at least 64 microprocessors.

86. The personal computer of claim 80, wherein said at least one microchip comprises at least 1024 microprocessors.

87. The personal computer of claim 80, wherein said at least one internal firewall is configured to permanently deny access to portions of said at least one microchip from said at least one network.

88. A personal computer comprising:
   at least one microchip, the at least one microchip comprising:
      at least four microprocessors, exclusive of any digital signal processors (DSPs);
      at least one digital signal processor (DSP);
      at least one power management component;
      at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
      at least one wireless network connection mechanism configured to connect the personal computer to the at least one network, the at least one network comprising:
         the Internet.

89. The personal computer of claim 88, wherein the at least one internal firewall is configured to deny access to at least one a first microchip microprocessor of the personal computer by at least one other computer connected to the at least one network during a shared use involving the personal computer and the at least one other computer of the at least one network, and
   the at least one internal firewall is further configured to allow access to at least one second microchip microprocessor of the at least one personal computer by the at least one other computer of the at least one network during the shared use;
   wherein the shared use includes unauthorized shared use, including intrusion by hackers from outside the personal computer.

90. The personal computer of claim 89, wherein the at least one internal firewall is configured to deny access to the at least one first microchip microprocessor of the personal computer by the at least one network of computers during a shared use involving the personal computer and the at least one network; and
   wherein the shared use comprises shared file resources and/or message passing.

91. The personal computer of claim 89, wherein the at least one internal firewall is configured to allow access to the at least one second microchip microprocessor of the personal computer by the at least one network during the shared use.

92. The personal computer of claim 91, wherein the at least one internal firewall is configured to allow access to the at least one second microchip microprocessor of the personal computer by the at least one network during the shared use.

93. The personal computer of claim 88, wherein said at least one microchip comprises at least 64 microprocessors.

94. The personal computer of claim 88, wherein said at least one microchip comprises at least 1024 microprocessors.

95. The personal computer of claim 88, wherein said at least one internal firewall is configured to permanently deny access to portions of said at least one microchip from said at least one network.

96. A personal computer, comprising:
   at least one microchip, the at least one microchip comprising:
      at least four microprocessors, exclusive of any digital signal processors (DSPs);
      at least one power management component function of the personal computer; and
      at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
      at least one wireless network connection mechanism configured to connect the personal computer to the at least one network, the at least one network comprising:
         the Internet;
   wherein the at least one microchip is an active configuration of at least one integrated circuit.

97. The personal computer of claim 96, wherein the at least one internal firewall is configured to deny access to at least one first microchip microprocessor of the personal computer by at least one other computer connected to the network during a shared use involving the personal computer and the at least one other computer of the at least one network, and
   the at least one internal firewall is further configured to allow access to at least one second microchip microprocessor of the personal computer by at the at least one other computer of the at least one network during the shared use;
   wherein the shared use includes unauthorized shared use, including intrusion by hackers from outside the personal computer.

98. The personal computer of claim 97, wherein the at least one internal firewall is configured to deny access to the at least one first microchip microprocessor of the personal computer by the at least one network of computers during the shared use involving the personal computer and the at least one network; and
   wherein the shared use comprises shared file resources and/or message passing.

99. The personal computer of claim 97, wherein the at least one internal firewall is configured to allow access to the at least one second microchip microprocessor of the personal computer by the at least one network during the shared use.

100. The personal computer of claim 99, wherein the at least one internal firewall is configured to allow access to the at least one second microchip microprocessor of the personal computer by the at least one network during the shared use.

101. The personal computer of claim 96, wherein said at least one microchip comprises at least 64 microprocessors.

102. The personal computer of claim 96, wherein said at least one microchip comprises at least 1024 microprocessors.

103. The personal computer of claim 96, wherein said at least one internal firewall is configured to permanently deny access to portions of said at least one microchip from said at least one network.

104. A personal computer, comprising:
   at least one microchip, the at least one microchip comprising:
      at least four microprocessors, exclusive of any digital signal processors (DSPs);

at least one field-programmable gate array (FPGA);
at least one power management component; and
at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
at least one wireless network connection mechanism configured to connect the personal computer to the at least one network, the at least one network comprising:
the Internet.

105. The personal computer of claim 104, wherein the at least one internal firewall is configured to deny access to at least one first microchip microprocessor of the personal computer by at least one other computer connected to the at least one network during a shared use involving the personal computer and the at least one other computer of the at least one network, and
the at least one internal firewall is further configured to allow access to at least one second microchip microprocessor of the personal computer by the at least one other computer of the at least one network during the shared use;
wherein the shared use includes unauthorized shared use, including intrusion by hackers from outside the personal computer.

106. The personal computer of claim 105, wherein the at least one internal firewall is configured to deny access to the at least one first microchip microprocessor of the personal computer by the at least one network of computers during a shared use involving the personal computer and the at least one network; and
wherein the shared use comprises shared file resources and/or message passing.

107. The personal computer of claim 105, wherein the at least one internal firewall is configured to allow access to the at least one second microchip microprocessor of the personal computer by the at least one network during the shared use.

108. The personal computer of claim 107, wherein the at least one internal firewall is configured to allow access to the at least one second microchip microprocessor of the personal computer by the at least one network during the shared use.

109. The personal computer of claim 104, wherein said at least one microchip comprises at least 64 microprocessors.

110. The personal computer of claim 104, wherein said at least one microchip comprises at least 1024 microprocessors.

111. The personal computer of claim 104, wherein said at least one internal firewall is configured to permanently deny access to portions of said at least one microchip from said at least one network.

112. A personal computer, comprising:
at least one microchip, the at least one microchip comprising:
at least four microprocessors, exclusive of any digital signal processors (DSPS);
at least one power management component; and
at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
at least one wireless network connection mechanism configured to connect the personal computer to the at least one network, the at least one network comprising:
the Internet,
the at least one wireless network connection mechanism comprising a capability to make at least one wireless connection to at least one second personal computer through at least one wireless link, and
the at least one wireless connection being made without any network servers or routers.

113. The personal computer of claim 112, wherein the at least one internal firewall is configured to deny access to at least one first microchip microprocessor of the personal computer by at least one other computer connected to the network during a shared use involving the personal computer and the at least one-other computer of the at least one network; and
the at least one internal firewall is further configured to allow access to at least one second microchip microprocessor of the personal computer by the at least one other computer of the at least one network during the shared use;
wherein the shared use includes unauthorized shared use, including intrusion by at least one hacker from outside the personal computer.

114. The personal computer of claim 113, wherein the at least one internal firewall is configured to deny access to the at least one first microchip microprocessor of the personal computer by the at least one network of computers during a shared use involving the personal computer and the at least one network; and
wherein the shared use comprises shared file resources and/or message passing.

115. The personal computer of claim 113, wherein the at least one internal firewall is configured to allow access to the at least one second microchip microprocessor of the personal computer by the at least one network during the shared use.

116. The personal computer of claim 115, wherein the at least one internal firewall is configured to allow access to the at least one second microchip microprocessor of the personal computer by the at least one network during the shared use.

117. The personal computer of claim 112, wherein the at least one wireless network connection mechanism makes the at least one wireless connection directly to the at least one second personal computer through only one wireless link.

118. The personal computer of claim 112, wherein the at least one wireless network connection mechanism comprises a capability to make the at least one wireless connection to at least one third personal computer through only one wireless link, such that the at least one third personal computer has a wireless connection to the at least one second personal computer through the personal computer.

119. The personal computer of claim 112, wherein said at least one microchip comprises at least 64 microprocessors.

120. The personal computer of claim 112, wherein said at least one microchip comprises at least 1024 microprocessors.

121. The personal computer of claim 112, wherein said at least one internal firewall is configured to permanently deny access to portions of said at least one microchip from said at least one network.

122. A personal computer, comprising:
at least one microchip, the at least one microchip comprising:
at least four microprocessors, exclusive of any digital signal processors (DSPs);
at least one non-volatile memory component;
at least one power management component; and
at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
at least one wireless network connection mechanism configured to connect the personal computer to the at least one network, the at least one network comprising:
the Internet.

123. The personal computer of claim 122, wherein the at least one internal firewall is configured to deny access to at least one first microchip microprocessor of the personal computer by at least one other computer connected to the at least one network during a shared use involving the personal computer and the at least one other computer of the at least one network, and
the at least one internal firewall is further configured to allow access to at least one second microchip microprocessor of the personal computer by the at least one other computer of the at least one network during the shared use;
wherein the shared use includes unauthorized shared use, including intrusion by at least one hacker from outside the personal computer.

124. The personal computer of claim 123, wherein the at least one internal firewall is configured to deny access to the at least one first microchip microprocessor of the personal computer by the at least one network of computers during a shared use involving the personal computer and the at least one network; and
wherein the shared use comprises shared file resources and/or message passing.

125. The personal computer of claim 123, wherein the at least one internal firewall is configured to allow access to the at least one second microchip microprocessor of the personal computer by the at least one network during the shared use.

126. The personal computer of claim 125, wherein the at least one internal firewall is configured to allow access to the at least one second microchip microprocessor of the personal computer by the at least one network during the shared use.

127. The personal computer of claim 122, wherein said at least one microchip comprises at least 64 microprocessors.

128. The personal computer of claim 122, wherein said at least one microchip comprises at least 1024 microprocessors.

129. The personal computer of claim 122, wherein said at least one internal firewall is configured to permanently deny access to portions of said at least one microchip from said at least one network.

130. A personal computer, comprising:
at least one microchip, the at least one microchip comprising:
at least four microprocessors, exclusive of any digital signal processors (DSPs);
at least one digital signal processor (DSP);
at least one power management component; and
at least one internal firewall, the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
at least one wireless network connection mechanism configured to connect the personal computer to the at least one network, the at least one network comprising:
the Internet; and
the World Wide Web.

131. The personal computer of claim 130, wherein the at least one internal firewall is configured to deny access to at least one first microchip microprocessor of the personal computer by at least one other computer connected to the at least one network during a shared use involving the personal computer and the at least one other computer of the at least one network, and
the at least one internal firewall is further configured to allow access to at least one second microchip microprocessor of the personal computer by the at least one other computer of the at least one network during the shared use;
wherein the shared use includes unauthorized shared use, including intrusion by hackers from outside the personal computer.

132. The personal computer of claim 131, wherein the at least one internal firewall is configured to deny access to the at least one first microchip microprocessor of the personal computer by the at least one network of computers during a shared use involving the personal computer and the at least one network; and
wherein the shared use comprises shared file resources and/or message passing.

133. The personal computer of claim 130, wherein said at least one microchip comprises at least 64 microprocessors.

134. The personal computer of claim 130, wherein said at least one microchip comprises at least 1024 microprocessors.

135. The personal computer of claim 130, wherein said at least one internal firewall is configured to permanently deny access to portions of said at least one microchip from said at least one network.

136. A personal computer, comprising:
at least one microchip, the at least one microchip comprising:
at least four microprocessors, exclusive of any digital signal processors (DSPs);
at least one digital signal processor (DSP);
at least one power management component; and
at least one internal firewall, the at least one internal firewall being at least one hardware firewall configured to allow and/or deny access to portions of the at least one microchip both to at least one at least one user of the personal computer and to at least one user of the at least one microchip from at least one network of computers during a shared use of the at least one microchip, and the at least one internal firewall configured to deny access to portions of the at least one microchip from the at least one network; and at least one wireless network connection mechanism configured to connect the personal computer to the at least one network, the at least one network comprising:
the Internet.

137. The personal computer of claim 136, wherein the at least one internal firewall is configured to deny access to at least one first microchip microprocessor of the personal computer by at least one other computer connected to the at least one network during the shared use involving the personal computer and the at least one-other computer of the at least one network, and
the at least one internal firewall is further configured to allow access to at least one second microchip microprocessor of the at least one at least one personal computer by the at least one other computer of the at least one network during the shared use;
wherein the shared use includes unauthorized shared use, including intrusion by hackers from outside the personal computer.

138. The personal computer of claim 137, wherein the at least one internal firewall is configured to deny access to the at least one first microchip microprocessor of the personal computer by the at least one network of computers during the shared use involving the personal computer and the at least one network; and
wherein the shared use comprises shared file resources and/or message passing.

139. The personal computer of claim 126, wherein the at least one internal firewall is configured to allow access to the at least one second microchip microprocessor of the personal computer by the at least one network during the shared use.

140. The personal computer of claim 139, wherein the at least one internal firewall is configured to allow access to the at least one second microchip microprocessor of the personal computer by the at least one network during the shared use.

141. The personal computer of claim 136, wherein said at least one microchip comprises at least 64 microprocessors.

142. The personal computer of claim 136, wherein said at least one microchip comprises at least 1024 microprocessors.

143. The personal computer of claim 136, wherein said at least one internal firewall is configured to permanently deny access to portions of said at least one microchip from said at least one network.

144. A personal computer, comprising:
at least one microchip, the at least one microchip comprising:
at least four microprocessors, exclusive of any digital signal processors (DSPs);
at least one application-specific integrated circuit (ASIC);
at least one power management component; and
at least one internal firewall;
the at least one internal firewall being at least one hardware firewall configured to allow and/or deny access to portions of the at least one microchip both to at least one user of the personal computer and to at least one user of the at least one microchip from at least one network of computers during a shared use of the at least one microchip, and the at least one internal firewall being configured to deny access to portions of the at least one microchip from the at least one network; and
at least one wireless network connection mechanism configured to connect the personal computer to the at least one network, the at least one network comprising:
the Internet.

145. The personal computer of claim 144, wherein the at least one internal firewall is configured to deny access to at least one first microchip microprocessor of the personal computer by at least one other computer connected to the at least one network during the shared use involving the personal computer and the at least one other computer of the network; and
the at least one internal firewall is further configured to allow access to at least one second microchip microprocessor of the personal computer by the at least one network of computers during the shared use;
wherein the shared use includes unauthorized shared use, including intrusion by at least one hacker from outside the personal computer.

146. The personal computer of claim 145, wherein the at least one internal firewall is configured to deny access to the at least one first microchip microprocessor of the personal computer by the at least one network of computers during shared use involving the personal computer and the at least one network; and
wherein the shared use comprises shared file resources and/or message passing.

147. The personal computer of claim 145, wherein the at least one internal firewall is configured to allow access to the at least one second microchip microprocessor of the personal computer by the at least one network during the shared use.

148. The personal computer of claim 147, wherein the at least one internal firewall is configured to allow access to the at least one second microchip microprocessor of the personal computer by the at least one network during the shared use.

149. The personal computer of claim 144, wherein said at least one microchip comprises at least 64 microprocessors.

150. The personal computer of claim 144, wherein said at least one microchip comprises at least 1024 microprocessors.

151. The personal computer of claim 144, wherein said at least one internal firewall is configured to permanently deny access to portions of said at least one microchip from said at least one network.

* * * * *

UNITED STATES PATENT AND TRADEMARK OFFICE
CERTIFICATE OF CORRECTION

| | | |
|---|---|---|
| PATENT NO. | : 7,606,854 B2 | Page 1 of 1 |
| APPLICATION NO. | : 09/884041 | |
| DATED | : October 20, 2009 | |
| INVENTOR(S) | : Frampton E. Ellis, III | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1856 days.

Signed and Sealed this

Fourteenth Day of December, 2010

David J. Kappos
*Director of the United States Patent and Trademark Office*